(12) United States Patent
Natrajan et al.

(10) Patent No.: US 10,710,962 B2
(45) Date of Patent: *Jul. 14, 2020

(54) ZWITTERIONIC REAGENTS

(71) Applicant: Siemens Healthcare Diagnostics Inc., Tarrytown, NY (US)

(72) Inventors: Anand Natrajan, Manchester, NH (US); David Sharpe, Foxborough, MA (US); David Wen, Northborough, MA (US); Qingping Jiang, East Walpole, MA (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/168,018

(22) Filed: May 28, 2016

(65) Prior Publication Data

US 2016/0274094 A1 Sep. 22, 2016

Related U.S. Application Data

(62) Division of application No. 13/699,435, filed as application No. PCT/US2011/036971 on May 18, 2011, now Pat. No. 9,487,480.

(Continued)

(51) Int. Cl.
*G01N 33/53* (2006.01)
*C07C 309/14* (2006.01)
(Continued)

(52) U.S. Cl.
CPC ........ *C07D 207/452* (2013.01); *A61K 47/545* (2017.08); *A61K 47/643* (2017.08);
(Continued)

(58) Field of Classification Search
CPC .............. C07C 309/14; C07D 207/452; C07D 207/46; C07D 403/12; C07D 493/10; C07D 495/04; C07F 9/091
See application file for complete search history.

(56) References Cited

U.S. PATENT DOCUMENTS 5,418,295 A 5/1995 Bowers et al.
5,760,021 A 6/1998 Ebetino et al.
(Continued)

FOREIGN PATENT DOCUMENTS

EP 0061872 8/1985
JP 41000730 1/1965
(Continued)

OTHER PUBLICATIONS

Gubbens et al., Photocrosslinking and click chemistry enable the specific detention of proteins interacting with . . . , Chemistry & Biology, Jan. 30, 2009, 16(1), pp. 3-14.
(Continued)

*Primary Examiner* — Shafiqul Haq

(57) ABSTRACT

Zwitterion-containing compounds for the modification of hydrophobic molecules to improve their solubility and/or to lower their non-specific binding as provided. The zwitterion-containing compounds may be suitable for modification of detectable labels such as biotin and fluorescein to improve their solubility. The zwitterion-containing compounds may also be useful for the preparation of conjugates of proteins, peptides and other macromolecules or for crosslinking molecules and/or macromolecules.

36 Claims, 5 Drawing Sheets

Related U.S. Application Data

(60) Provisional application No. 61/346,926, filed on May 21, 2010.

(51) Int. Cl.

| | | |
|---|---|---|
| *C07D 207/46* | (2006.01) | |
| *C07D 207/452* | (2006.01) | |
| *C07D 403/12* | (2006.01) | |
| *C07D 493/10* | (2006.01) | |
| *C07D 495/04* | (2006.01) | |
| *C07F 9/09* | (2006.01) | |
| *C09B 11/24* | (2006.01) | |
| *A61K 47/54* | (2017.01) | |
| *A61K 47/64* | (2017.01) | |
| *C07K 1/13* | (2006.01) | |
| *C07K 7/06* | (2006.01) | |
| *C07K 14/765* | (2006.01) | |

(52) U.S. Cl.
CPC .......... *C07C 309/14* (2013.01); *C07D 207/46* (2013.01); *C07D 403/12* (2013.01); *C07D 493/10* (2013.01); *C07D 495/04* (2013.01); *C07F 9/091* (2013.01); *C07K 1/13* (2013.01); *C07K 7/06* (2013.01); *C07K 14/765* (2013.01); *C09B 11/24* (2013.01); *G01N 33/5306* (2013.01)

(56) References Cited

U.S. PATENT DOCUMENTS

| | | | |
|---|---|---|---|
| 6,017,895 | A | 1/2000 | Cook |
| 8,778,624 | B2 * | 7/2014 | Natrajan .............. C07D 219/04 435/7.1 |
| 9,487,480 | B2 * | 11/2016 | Natrajan .......... A61K 47/48061 |
| 2004/0167040 | A1 | 8/2004 | Dahlmann et al. |
| 2005/0123501 | A1 | 6/2005 | Lewis |
| 2006/0068390 | A1 | 3/2006 | Tillett et al. |
| 2006/0183863 | A1 | 8/2006 | Huang et al. |
| 2006/0199955 | A1 | 9/2006 | Lukhtanov et al. |
| 2009/0156460 | A1 | 6/2009 | Jiang et al. |
| 2009/0326275 | A1 | 12/2009 | DiMauro |

FOREIGN PATENT DOCUMENTS

| | | |
|---|---|---|
| JP | 58039651 | 3/1983 |
| JP | 64047389 | 2/1989 |
| JP | 01225494 | 9/1989 |
| JP | 02113899 | 4/1990 |
| JP | 0411073 | 1/1992 |
| JP | 0411075 | 1/1992 |
| JP | 0434078 | 2/1992 |
| JP | 0434079 | 2/1992 |
| JP | 10-158979 | 6/1998 |
| JP | 2002-52714 | 11/1998 |
| JP | 2003105671 | 4/2003 |
| JP | 2001-002965 | 9/2006 |
| JP | 2009513758 | 4/2009 |
| JP | 2009533339 | 9/2009 |
| JP | 2010506857 | 3/2010 |
| JP | 5852578 | 12/2015 |
| WO | 9811906 | 3/1998 |
| WO | 9843676 | 10/1998 |
| WO | 2004038378 | 5/2004 |
| WO | 2004067775 | 8/2004 |
| WO | 2004067776 | 8/2004 |
| WO | 2008141012 | 11/2008 |

OTHER PUBLICATIONS

Nomura, Kohji, Incomplete dialysis of protein samples containing 3-[93-Cholamidopropyl) dimethylammonio]-1-propanesulfonate may lead to erroneous estimation of histidine content on amino acid analysis, Analytical Biochemistry, 2001, 290(1), pp. 98-101.

Kane et al., Kosmotropes Form the Basis of Protein-Resistant Surfaces, Langmuir, 2003, 19 (6), pp. 2388-2391.

Sandbhor, et al., A Modular Synthesis of Alkynyl-Phosphocholine Headgroups for Labeling Sphingomyelin and Phosphatidylcholine, Journal of Organic Chemistry, Aug. 24, 2009, 74(22), pp. 8669-8674.

Gubbens et al., Photocrosslinking and Click Chemistry Enable the Specific Detention of Protein Interacting With . . . , Chemistry & Biology, Jan. 30, 2009, 16(1), pp. 3-14.

Uragami et al., Design and Synthesis of Phosphatidylcholine Mimics and Their Mixing Behavior with Phosphatidylglycerol . . . , Langmuir, 2000, 16(21), pp. 8010-8015.

Enjalbert et al., Preparation de Nouveaux B-aminoacides a longue chaine et leur . . . , Journal of Fluorine Chemistry 93 (1999), pp. 145-152.

The Chemical Society of Japan (Nihon Kagakukaishi), 1984, (3), pp. 463-466.

Wang, Yan-Feng et al; "Studies on syntheses and properties of novel polyamides containing phosphatidylcholine analogous moieties by interfacial polycondensation"; Journal of Polymer Science Part A: Polymer Chemistry; Jan. 10, 1977, pp. 3065-3074; XP055141815.

International Search Report dated Nov. 9, 2011 in corresponding PCT Application No. PCT/US2011/36971.

* cited by examiner

Z2-PFP, 1d

Z3-PFP, 2c

Z4-PFP, 3c

ZPB-PFP, 4c

Z-NH$_2$, 5c

Z-Maleimide-1, 6b

Z-Maleimide-2, 7a

Z-diamine, 8c

Z-Di-NHS, 8d

Z-maleimide-NHS, 9e

Biotin-Z-NH₂, 10a

Biotin-Z-NHS, 10c

Fluorescein-Z-NH₂, 11a

Fluorescein-Z-NHS, 11e

Fluorescein-Z-3-CMO-Progesterone, 11d

Fluorescein-Z-22-CMO-FK506, 11e

| Hydrophobic peptide | Labeled peptide, aqueous solubility |
|---|---|
| Phe-Phe-Phe-Phe-Phe | 12a, ~0.5 mM |
| Phe-Gly-Gly-Phe | 12b, ~3.0 mM |
| Leu-Leu-Leu-Leu-Leu | 12c, > 0.1 mM |
| Ile-Ile-Ile-Ile-Ile | 12d, > 0.1 mM |

12a

12b

12c

12d

ZWITTERIONIC REAGENTS

CROSS REFERENCE TO RELATED APPLICATIONS

This application is a divisional application of U.S. patent application Ser. No. 13/699,435 filed Nov. 21, 2012, which is a national phase entry of PCT International Patent Application No. PCT/US2011/036971 filed May 18, 2011, which claims priority to and the benefit of U.S. Provisional Application No. 61/346,926 filed May 21, 2010, the disclosures of each of which applications are hereby incorporated herein by reference in its entirety.

FIELD OF INVENTION

The present invention relates to hydrophilic, zwitterionic reagents. These reagents, because of their hydrophilic nature, are useful for improving the solubility of hydrophobic molecules and reducing their non-specific binding to solid phases, such as microparticles. The present invention also describes zwitterion-containing linkers for improving the aqueous solubility of detectable labels such as fluorescein and biotin and for synthesizing conjugates of these labels to haptens. The present invention also describes zwitterionic cross-linkers useful for preparing conjugates of peptides, proteins and other macromolecules.

BACKGROUND

Improving the aqueous solubility of reagents, preventing their aggregation, lowering their non-specific binding and reducing their non-specific interactions with sample components in serum or whole blood, remain ongoing challenges in clinical diagnostic assays. Commercial diagnostic immunoassays often use hydrophobic chemiluminescent and fluorescent labels that have limited aqueous solubility and these labels can exacerbate the non-specific binding of proteins, such as antibodies. Increasingly, recombinant proteins and peptides are being used in diagnostics and often these polypeptides exhibit poor aqueous solubility as well as a tendency to form insoluble aggregates because of misfolding or denaturation. Reagents can also interact with sample components in a non-specific manner giving rise to false positives in assays.

Several strategies to address some of the above mentioned issues have been described in the literature. For example, Basu et al. (*Bioconjugate Chem.* 2006, 17, 618-630) and Marsac et al. (*Bioconjugate Chem.* 2006, 17, 1492-1498) have described the use of poly(ethylene)glycol (PEG) to improve the solubility of polypeptides and proteins. Natrajan et al. (U.S. Pat. Nos. 6,664,032 and 7,309,615)) on the other hand have described the use of PEG to improve the aqueous solubility of hydrophobic, chemiluminescent, acridinium ester labels. Goldberg and coworkers (*Biophysical Chem.* 2003, 100, 569-479) synthesized a variety of non-detergent, zwitterionic sulfobetaines (NDSBs) and showed that these compounds are useful additives in assisting refolding of proteins such as BSA as well as enzymes and a monoclonal antibody. Similarly, D'Amico and Feller, (*Anal. Biochem.* 2009, 385, 389-391) have shown that the addition of an NDSB inhibited the thermal denaturation of several proteins. In another approach, Tolbert and coworkers (*Bioconjugate Chem.* 2008, 19, 1113-1118) have recently reported that site-specific modification of two aggregation-prone polypeptides with betaine (trimethylammonium moiety) significantly improved the aqueous solubility of the two polypeptides and inhibited aggregate formation.

Besides protein modification to improve their solubility, PEG has also been used devise inert surfaces that resist protein adsorption. For example, Ostuni et al. in *J. Am. Chem. Soc.* 2000, 17, 5605-5620, evaluated numerous functional groups attached to self-assembled monolayers for resistance to protein adsorption and observed that poly(ethylene)glycol functional groups conferred the best resistance. More recently, Jiang and coworkers in *Biomacromolecules* 2008, 9, 1357-1361; and others have reported that zwitterion-modified hydrophilic surfaces are as inert to protein adsorption as PEG. Structures of some zwitterions such as sulfobetaines, carboxybetaines, phosphobetaines and amine oxides are shown in the exemplary structures below. Like PEG, these zwitterions are normally electrically neutral, because of the balance of positive and negative charges within a given structure ($R_1$-$R_4$ are typically alkyl groups).

Examples of Zwitterions

Sulfobetaines

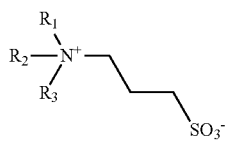

zwitterionic at both
low and high pH

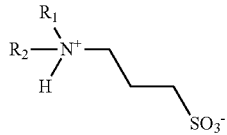

anionic at pH >7

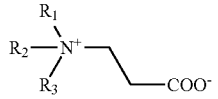

Carboxybetaine
cationic at low pH

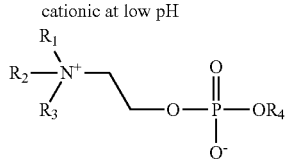

Phosphobetaine

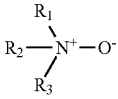

Tertiary Amine Oxide

Sulfobetaines where the nitrogen atom is quarternary, maintain their electrical neutrality over a wide pH range. On the other hand sulfobetaines with a tri-substituted nitrogen can acquire a negative charge at higher pH (pH>7) because they can be deprotonated at the nitrogen thereby neutralizing its positive charge. Similarly, carboxybetaines are electrically neutral at higher pH but can be protonated at the carboxylate group and acquire a net positive charge at low pH (pH<5).

Zwitterionic dye molecules for labeling in proteomic and other biological analyses are reported in U.S. Patent Application No. 2007/0259333 A1 to Dratz et al. In these zwitterionic dye molecules, the cationic and anionic moieties forming the zwitterionic portion of the dye molecules are not directly attached to each other by a hydrocarbon moiety.

The zwitterion-containing compounds of the current invention, are useful for introducing zwitterions onto hydrophobic molecules to improve their solubility and to lower their non-specific binding, have not been described in the prior art. Zwitterion containing cross-linking reagents and zwitterion-containing linkers of the present invention, which may also be useful for synthesizing conjugates with increased aqueous solubility, have also not been disclosed in the prior art.

There is a continuing need in the art to improve the aqueous solubility of hydrophobic molecules and for improved reagents for immunoassays and the like. It is therefore an object of the invention to provide zwitterion-containing molecules which can improve the solubility of a molecule or macromolecule, such as an analyte, and exhibit reduced non-specific binding to a solid phase.

SUMMARY OF THE INVENTION

In accordance with the foregoing objectives and others, it has surprisingly been found that the properties of hydrophobic compounds are improved by covalently linking zwitterionic groups with the hydrophobic molecule to increase its hydrophilicity, solubility in aqueous solutions and consequently reduce non-specific binding with solid phases.

In one aspect of the invention, a zwitterion-containing compound for forming a conjugate with a peptide, protein, or macromolecule is provided. The zwitterion-containing compound has the structure of formula (I):

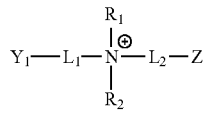

(I)

wherein, $L_1$ is a divalent $C_{1-20}$ alkyl, alkenyl, alkynyl, aryl, or aralkyl group, optionally substituted with up to 20 heteroatoms;

$L_2$ is a bond or a divalent $C_{1-4}$ alkyl, alkenyl, or alkynyl group, optionally substituted with up to 10 heteroatoms;

Z is an anion-containing group selected from the group consisting of carboxylate (—COO⁻), sulfonate (—SO$_3^-$), sulfate (—OSO$_3^-$), phosphate (—OP(O)(OR)(O⁻)), and oxide (—O⁻), where R is a $C_{1-12}$ alkyl, alkenyl, alkynyl, aryl, or aralkyl, optionally substituted with up to 20 heteroatoms;

$Y_1$ is a reactive functional group for forming covalent linkages with a peptide, a protein, or a macromolecule, said functional group comprising a electrophilic group, nucleophilic group, or a photoreactive group; and $R_1$ and $R_2$ are independently selected at each occurrence from $C_{1-20}$ alkyl, alkenyl, alkynyl, aryl, or aralkyl groups, each optionally substituted with up to 20 heteroatoms.

In one embodiment, the zwitterion-containing compound of Formula (I) has the structure:

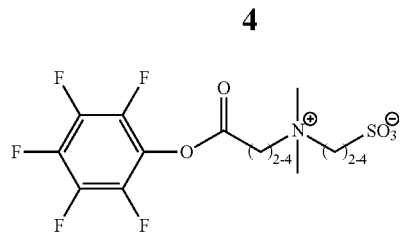

In another embodiment, the zwitterion-containing compound of Formula (I) has the structure:

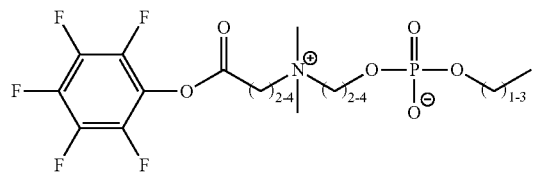

In another embodiment, the zwitterion-containing compound of Formula (I) has the structure:

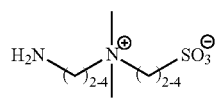

In another embodiment, the zwitterion-containing compound of Formula (I) has the structure:

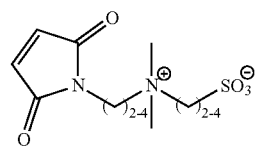

In another embodiment, the zwitterion-containing compound of Formula (I) has the structure:

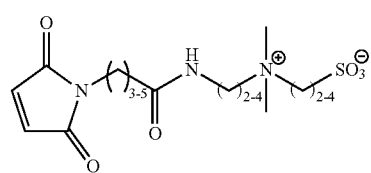

In another aspect of the invention, a zwitterion-containing compound for labeling an analyte, analyte analog, or binding partner for an analyte is provided. The zwitterion-containing compound has the structure of formula (II):

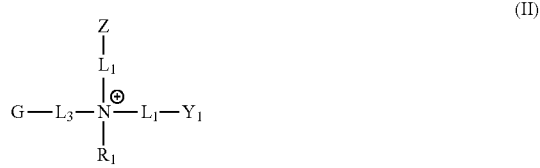

(II)

wherein, $L_1$ and $L_3$, are independently selected at each occurrence from divalent $C_{1-20}$ alkyl, alkenyl, alkynyl, aryl, or aralkyl groups, each optionally substituted with up to 20 heteroatoms;

$L_2$ is a bond or a divalent $C_{1-4}$ alkyl, alkenyl, or alkynyl group, optionally substituted with up to 10 heteroatoms;

Z is an anion-containing group selected from the group consisting of carboxylate (—COO⁻), sulfonate (—SO₃⁻), sulfate (—OSO₃⁻), phosphate (—OP(O)(OR)(O⁻)), and oxide (—O⁻), where R is a $C_{1-12}$ alkyl, alkenyl, alkynyl, aryl, or aralkyl, optionally substituted with up to 20 heteroatoms;

$Y_1$ is a reactive functional group for forming covalent linkages with an analyte, analyte analog, or binding partner for an analyte, said functional group comprising a electrophilic group, nucleophilic group, or a photoreactive group;

G is a detectable label; and $R_1$ is a $C_{1-20}$ alkyl, alkenyl, alkynyl, aryl, or aralkyl, optionally substituted with up to 20 heteroatoms.

In one embodiment, $L_3$ is a group —$X^G$—$R^G$—, where $X^G$ is attached to G, and $X^G$ is selected from a bond, oxygen, sulfur, amine, amide (—C(O)NR$^N$— or —NR$^N$—C(O)—), ester (—C(O)—O— or —O—C(O)—), carbamate (—NR$^N$—C(O)—O— or —O—C(O)—NR$^N$—) or urea (—NR$^N$—C(O)—NR$^N$—), and R$^N$ is hydrogen or a $C_{1-20}$ alkyl, alkenyl, alkynyl, aryl, or aralkyl, optionally substituted with up to 20 heteroatoms; and R$^G$ is a divalent $C_{1-20}$ alkyl, alkenyl, alkynyl, aryl, or aralkyl group, optionally substituted with up to 20 heteroatoms.

In one embodiment, the zwitterion-containing compound of Formula (II) has the structure:

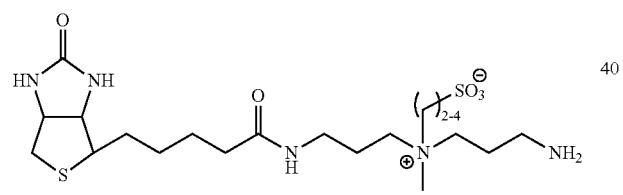

In another embodiment, the zwitterion-containing compound of Formula (II) has the structure:

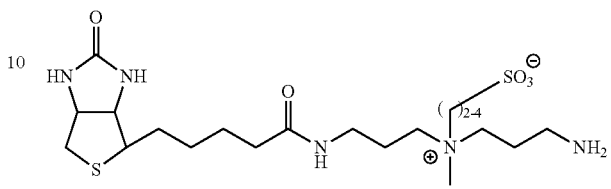

In another embodiment, the zwitterion-containing compound of Formula (II) has the structure:

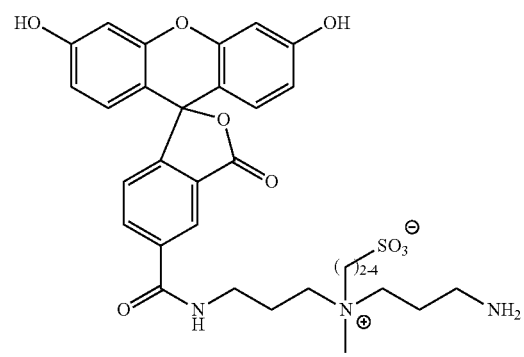

In another embodiment, the zwitterion-containing compound of Formula (II) has the structure:

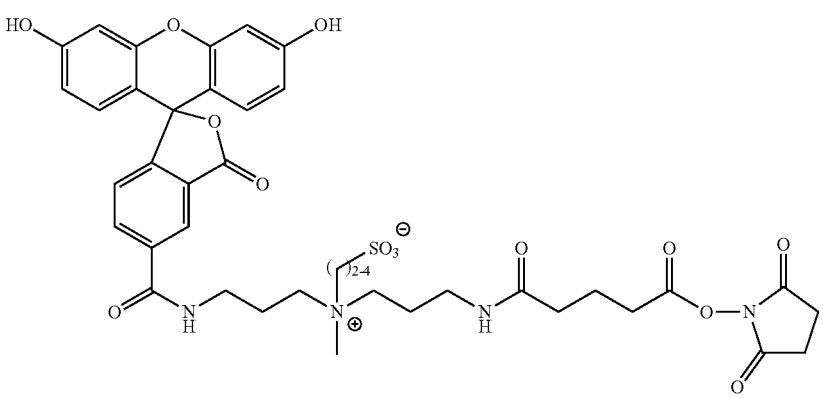

In a further aspect of the invention, a zwitterion-containing compound for cross-linking peptides, proteins, and/or macromolecules is provided. The zwitterion-containing compound has the structure of formula (III):

$$Y_1\text{-}\Omega\text{-}Y_2 \qquad \text{(III)}$$

wherein, $\Omega$ is a zwitterion-containing group of the form

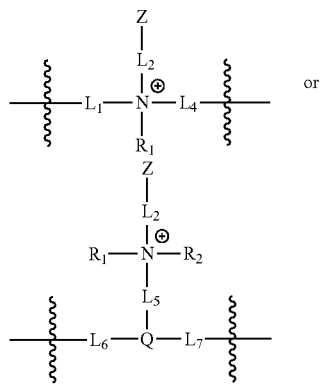 or

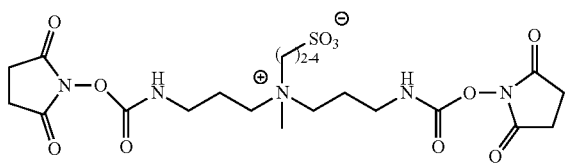

$L_1$ and $L_4$ are independently selected at each occurrence from divalent $C_{1-20}$ alkyl, alkenyl, alkynyl, aryl, or aralkyl groups, each optionally substituted with up to 20 heteroatoms;

$L_2$ is a bond or a divalent $C_{1-4}$ alkyl, alkenyl, or alkynyl group, optionally substituted with up to 10 heteroatoms;

$L_5$, $L_6$, and $L_7$ are independently selected at each occurrence from a bond or divalent $C_{1-20}$ alkyl, alkenyl, alkynyl, aryl, or aralkyl groups, each optionally substituted with up to 20 heteroatoms;

Q is selected from a carbon or nitrogen atom, and with the proviso that when Q is nitrogen, $L_5$, $L_6$, and $L_7$ are each not a bond;

Z is an anion-containing group selected from the group consisting of carboxylate (—COO⁻), sulfonate (—SO₃⁻), sulfate (—OSO₃⁻), phosphate (—OP(O)(OR)(O⁻)), and oxide (—O⁻), where R is a $C_{1-12}$ alkyl, alkenyl, alkynyl, aryl, or aralkyl, optionally substituted with up to 20 heteroatoms;

$Y_1$ and $Y_2$ are independently selected at each occurrence from a reactive functional group for forming covalent linkages with a peptide, a protein, or a macromolecule comprising a electrophilic group, a nucleophilic group, or a photoreactive group; and $R_1$ and $R_2$ are independently selected at each occurrence from $C_{1-20}$ alkyl, alkenyl, alkynyl, aryl, or aralkyl, each optionally substituted with up to 20 heteroatoms.

In one embodiment, the zwitterion-containing compound of Formula (III) has the structure:

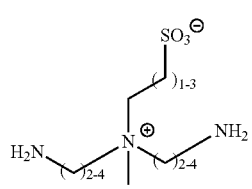

Specifically, the zwitterion-containing compound may have the structure:

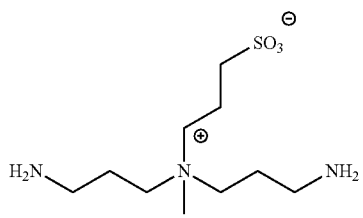

In another embodiment, the zwitterion-containing compound of Formula (III) has the structure:

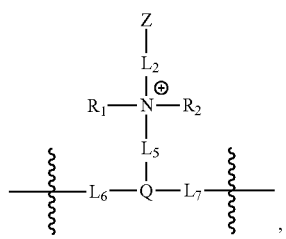

In another embodiment, Q is a zwitterion-containing group of the form

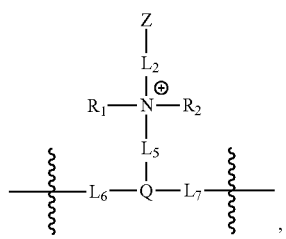

and $L_5$, $L_6$ and $L_7$ are each a group —$X^a$—$R^a$, where $X^a$ is attached to Q and is independently selected at each occurrence from a bond, oxygen, sulfur, amine, amide (—C(O)NR$^N$— or —NR$^N$—C(O)—), ester (—C(O)—O— or —O—C(O)—), carbamate (—NR$^N$—C(O)—O— or —O—C(O)—NR$^N$—) or urea (—NR$^N$—C(O)—NR$^N$—), and R$^N$ is independently selected at each occurrence from hydrogen or $C_{1-20}$ alkyl, alkenyl, alkynyl, aryl, or aralkyl groups, optionally substituted with up to 20 heteroatoms; and $R^a$ is independently selected at each occurrence from a bond or divalent $C_{1-20}$ alkyl, alkenyl, alkynyl, aryl, or aralkyl groups, each optionally substituted with up to 20 heteroatoms, with the proviso that when Q is nitrogen, $R^a$ is not a bond.

In another embodiment, a zwitterion-containing compound for cross-linking peptides, proteins, and/or macromolecules is provided. The zwitterion-containing compound has the structure:

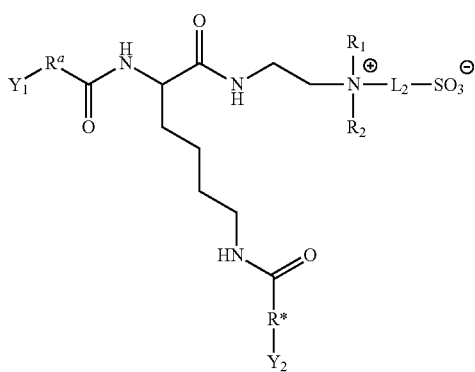

wherein $L_2$ is a divalent radical of the form —$(CH_2)_m$— where m=1 to 4; and $R^a$ and $R^*$ are independently selected at each occurrence from a bond or divalent $C_{1-15}$ alkyl, alkenyl, alkynyl, aryl, or aralkyl groups, each optionally substituted with up to 20 heteroatoms.

Specifically, the zwitterion-containing compound for cross-linking peptides, proteins, and/or macromolecules may have the structure:

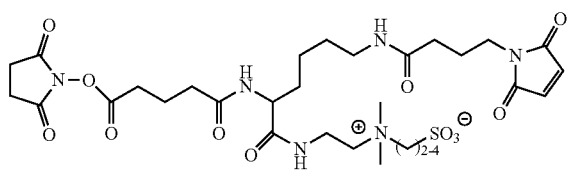

In one embodiment, a method of improving the aqueous solubility of a peptide, protein or macromolecule is provided. The method comprises comprising covalently attaching the zwitterion-containing compound of Formula I to the peptide, protein or macromolecule.

In another embodiment, a method of reducing non-specific binding of an analyte, analyte analog, or binding partner for an analyte in a biologic binding assay is provided. The method comprises covalently attaching the zwitterion-containing compound of Formula I to the analyte, analyte analog, or binding partner for an analyte.

In a further embodiment, a method of labeling an analyte, analyte analog, or binding partner for an analyte in a biologic binding assay is provided. The method comprises covalently attaching the zwitterion-containing compound of Formula II to the analyte, analyte analog, or binding partner for an analyte.

In yet another embodiment, a method for preparing a conjugate of two molecules and/or macromolecules comprising covalently attaching the zwitterion-containing compound of Formula III to a first molecule or macromolecule and a second molecule or macromolecule.

These and other aspect of the invention will be better understood by reference to the following detailed description, including the appended claims.

DETAILED DESCRIPTION

Figure 1:
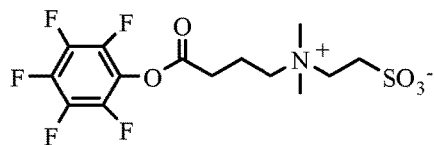
FIG. 1 provides the chemical structures of a plurality of exemplary zwitterion-containing compounds of the present invention.
Figure 1:
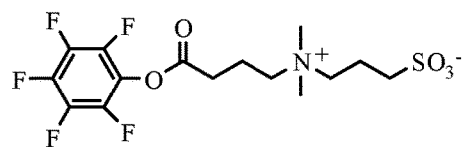
Figure 1:
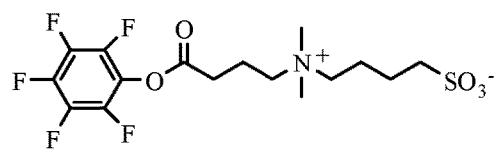
Figure 1:
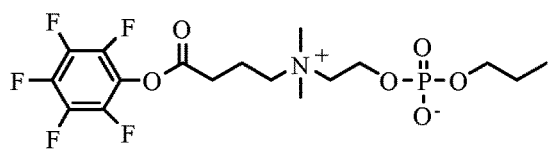
Figure 1:
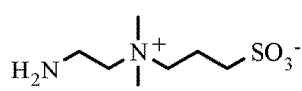
Figure 1:
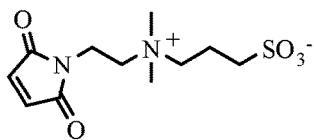
Figure 1:
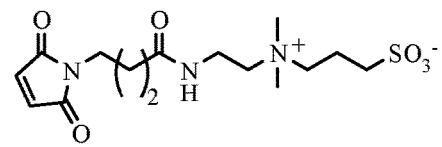
Figure 1:
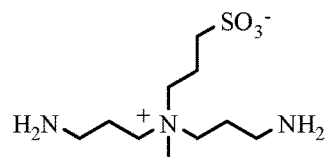
Figure 1:
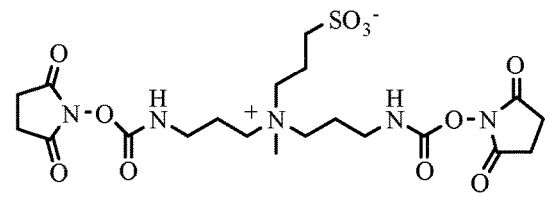
Figure 1:
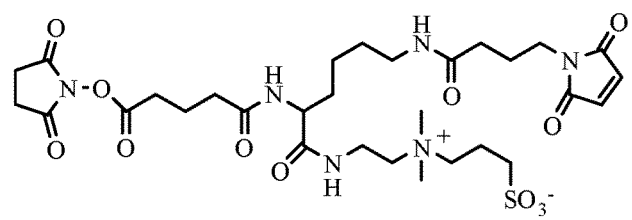

One objective of this invention is to provide structures of zwitterion-containing compounds for the modification of hydrophobic molecules to improve their solubility and/or to lower their non-specific binding. Another objective of this invention is to provide zwitterionic linkers for the modification of detectable labels such as biotin and fluorescein to improve their solubility and for the synthesis of conjugates with increased aqueous solubility. Yet another objective of the current invention is to provide zwitterion-containing cross-linking reagents useful for the preparation of conjugates of proteins, peptides and other macromolecules.

The zwitterion-containing compounds according to the invention may be useful for modification of hydrophobic molecules to improve their solubility in aqueous solvents and/or to lower their non-specific binding in a solid phase as compared to an otherwise hydrophobic molecule not modified by said zwitterion-containing compound. Non-specific binding, in assays using solid phases such as particles or microtiter plates, are undesired binding interactions of these hydrophobic molecules, including, for example, biologic molecules that may be an analyte, analyte analog, or a binding partner for an analyte in a biologic binding assay, to these solid phases. These undesired binding interactions typically increase the background of the assay leading to a net lowering of the signal to background ratio in the assay and thereby decreasing assay sensitivity.

In certain embodiments, the hydrophobic molecule may be selected from a group consisting of peptides, proteins or macromolecules. In one embodiment, the zwitterion-containing compounds may comprise (i) a negatively charged group linked by a bond or a straight or branched hydrocarbon moiety, optionally substituted with up to 20 heteroatoms, to the nitrogen atom of a quaternary ammonium; and (ii) an electrophilic, nucleophilic or photoreactive group linked by a bond or a straight or branched hydrocarbon moiety, optionally substituted with up to 20 heteroatoms, to the nitrogen atom of the quaternary ammonium. In a preferred embodiment, the electrophilic, nucleophilic or photoreactive group is linked by a straight or branched hydrocarbon moiety to the nitrogen atom of the quaternary ammonium to provide a more stable molecule as compared to a molecule where the electrophilic, nucleophilic or photoreactive group is linked to the nitrogen atom of the quaternary ammonium by a bond. The negatively charged group linked to the nitrogen atom may together constitute a zwitterionic group, for example, in the case of a sulfobetaine, there is a positive charge on the quarternary nitrogen and a negative charge on the —$SO_3$ group, which is linked to the quarternary nitrogen by a divalent alkyl moiety. The hydrocarbon moiety linking the electrophilic, nucleophilic or photoreactive group to the nitrogen atom preferably comprises a divalent alkyl, alkenyl, alkynyl, aryl, or aralkyl group. More preferably, the hydrocarbon moiety linking the electrophilic, nucleophilic or photoreactive group to the nitrogen atom comprises a divalent radical from $C_{1-6}$ alkyl, alkenyl, alkynyl, aryl, or aralkyl groups. In other embodiments, the hydrocarbon moiety, may comprise an alkoxy, carboxyl, amine and/or carbonyl groups.

The terms "alkyl," "alkenyl," and "alkynl" as used herein, unless otherwise specified, includes, without limitation, straight, branched, or cyclic (also identified as cycloalkyl), primary, secondary, or tertiary hydrocarbons. Illustrative examples of alkyl groups are methyl, ethyl, propyl, isopropyl, cyclopropyl, butyl, secbutyl, isobutyl, tertbutyl, cyclobutyl, 1-methylbutyl, 1,1-dimethylpropyl, pentyl, cyclopentyl, isopentyl, neopentyl, cyclopentyl, hexyl, isohexyl, and cyclohexyl. Unless otherwise specified, alkyl alkenyl, alkynyl, aryl, or aralkyl groups can be unsubstituted or substituted with one or more heteroatoms or heteroatom-containing moieties.

Suitable heteroatoms or heteroatom-containing moieties include, for example, halogen, hydroxyl, carboxyl, acyl, acyloxy, amino, alkylamino, alkylimino, dialkylamino, arylamino, amido, ester, carboxamide, carbamate, alkoxyl, aryloxyl, alkylthiol, alkylsulfonate, nitro, cyano, oxo, oxa, azo, thio, sulfonyl, ester, phosphonyl, phosphinyl, thiol, thioether, thioester, thioalkoxy, thiocyanate, perfluoro, phosphate, oxime, sulfate, sulfo-alkyl, combinations thereof or any other functional group that does not inhibit the reactivity of this compound for forming a conjugate with a hydrophobic molecule, preferably a peptide, protein or macromolecule. Preferred heteroatoms or heteroatom-containing moieties substitutions include nitrogen, oxygen, carboxyl, amine and/or carbonyl groups.

In another embodiment, the zwitterion-containing compound may be useful for forming a covalent linkage with an analyte, analyte analog, or a binding partner for an analyte in a biologic binding assay for the determination or quantitation of analytes. Analytes that are typically measured in such assays are often substances of some clinical relevance and can span a wide range of molecules from large macromolecules such as proteins, nucleic acids, viruses bacteria, etc. to small molecules such as ethanol, vitamins, steroids, hormones, therapeutic drugs, etc. A 'sandwich' immunoassay typically involves the detection of a large molecule, also referred to as macromolecular analyte, using two binding molecules such as antibodies. One antibody is immobilized or attached to a solid phase such as a particle, bead, membrane, microtiter plate or any other solid surface. For example, an antibody can be covalently attached to a particle containing amines on its surface by using a cross-linking molecule such as glutaraldehyde. The attachment may also be non-covalent and may involve simple adsorption of the binding molecule to the surface of the solid phase, such as polystyrene beads and a microtiter plate. The second antibody can be covalently attached with a chemiluminescent or fluorescent molecule. In an exemplary assay, the two antibodies may bind to different regions of the macromolecular analyte. The macromolecular analyte can be, for example, antibodies, antibody fragments, cells, viruses, receptors, or synthetic polymers. The binding molecules can be antibodies, antibody fragments, nucleic acids, peptides, binding proteins or synthetic binding polymers. For example, the folate binding protein ("FBP") binds the analyte folate. Synthetic binding molecules that can bind a variety of analytes have also been reported by Mossbach et al. *Biotechnology* vol. 14, pp. 163-170 (1995).

In one embodiment, the zwitterion-containing compound has the following structure shown in Formula I:

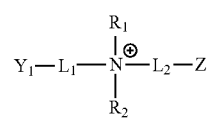

(1)

Z may be any suitable anion-containing group. In some embodiments, the anion-containing group Z together with the quaternary nitrogen of the compound of Formula I, form a zwitterion moiety. Suitable anion-containing groups include, for example, carboxylate (—COO$^-$), sulfonate (—SO$_3^-$), sulfate (—OSO$_3^-$), phosphate (—OP(O)(OR)(O$^-$)), and oxide (—O$^-$), where R is a hydrocarbon moiety. Preferably, R maybe an alkyl, alkenyl, alkynyl, aryl, or aralkyl, optionally substituted with up to 20 heteroatoms. In some embodiments, R may be a $C_{1-20}$, $C_{1-15}$, $C_{1-10}$, $C_{1-5}$ or $C_{1-3}$ alkyl, alkenyl, alkynyl, aryl, or aralkyl, optionally substituted with up to 3, 5, 10, 15 or 20 heteroatoms. In one exemplary embodiment, Z is an anion-containing group selected from the group consisting of carboxylate (—COO$^-$), sulfonate (—SO$_3^-$), sulfate (—OSO$_3^-$), phosphate (—OP(O)(OR)(O$^-$)), and oxide (—O$^-$), where R is a $C_{1-12}$ alkyl, alkenyl, alkynyl, aryl, or aralkyl, optionally substituted with up to 20 heteroatoms.

Particular mention may be made of the case where Z is sulfonate (—SO$_3^-$).

Another particularly suitable negatively charged group is where Z is phosphate (—OP(O)(OR)(O$^-$)) and R is a $C_{1-12}$ alkyl, alkenyl, alkynyl, aryl, or aralkyl, optionally including from 1-20 heteroatoms, such as oxygen, sulfur, and nitrogen atoms; where R is preferably selected from substituted or unsubstituted, branched, straight chain or cyclic, $C_1$-$C_{12}$ alkyl, alkenyl, alkynyl, aryl, benzyl, alkyl-aryl, aryl-alkyl, bicyclic alkyl, or aryl radicals, and combinations thereof, and wherein each of the foregoing radicals may be substituted with 1-6 heteroatoms and/or with any heteroatom-containing moiety, including, for example, halogen, hydroxyl, carboxyl, acyl, acyloxy, amino, alkylamino, alkylimino, dialkylamino, arylamino, amido, ester, carboxamide, carbamate, alkoxyl, aryloxyl, alkylthiol, alkylsulfonate, nitro, cyano, oxo, oxa, azo, thio, sulfonyl, ester, phosphonyl, phosphinyl, thiol, thioether, thioester, thioalkoxy, thiocyanate, perfluoro, phosphate, oxime, sulfate, sulfo-alkyl, and combinations thereof.

$Y_1$ may comprise any suitable reactive functional group for forming covalent linkages with a hydrophobic molecule, such as, for example, a peptide, a protein, or a macromolecule. More particularly, $Y_1$ may comprise any electrophilic, nucleophilic or photoreactive group suitable for forming a conjugate with a hydrophobic molecule. For example, $Y_1$ may comprise a reactive functional group for forming covalently linkages with an analyte, analyte analog, or a binding partner for an analyte in a biologic binding assay for the determination or quantitation of analytes. In certain embodiments, suitable functional groups for $Y_1$ may include, for example, amine-reactive groups, thiol-reactive groups, carboxy-reactive groups, maleimidyl-reactive groups, carbohydrate-reactive groups, or photoreactive-groups. More particularly, suitable functional groups for $Y_1$ may include, for example:

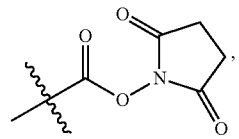

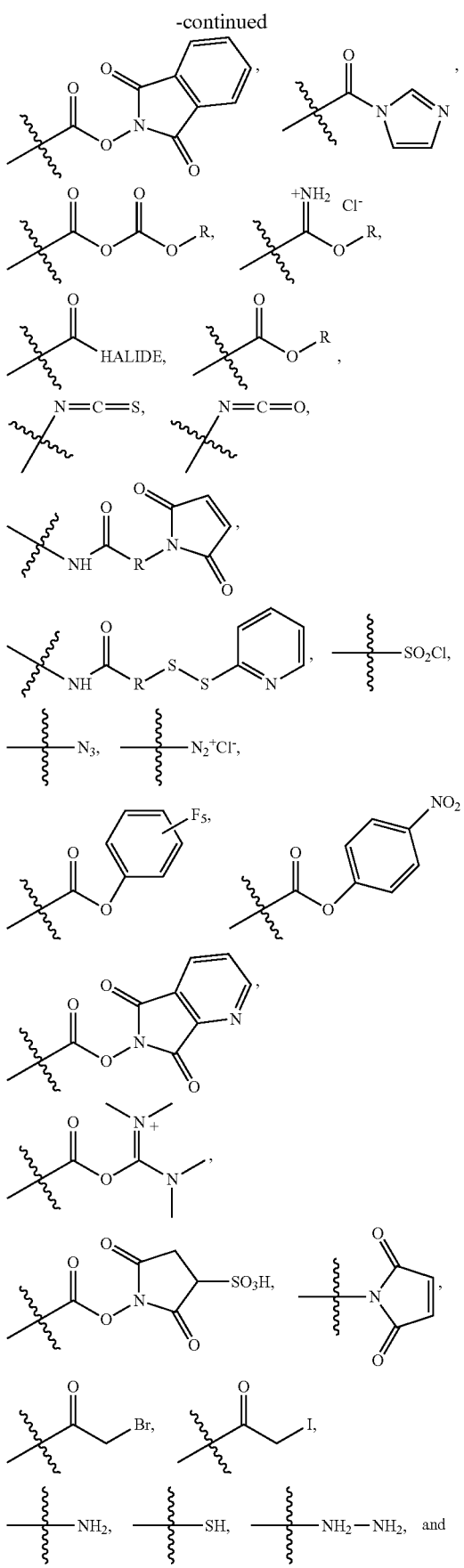

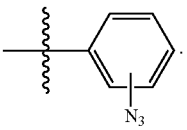

In certain preferred embodiments, $Y_1$ may a pentafluorophenyl (PFP) ester, maleimide, amine, or N-succinimidyloxycarbonyl.

$L_1$ may be any divalent hydrocarbon moiety, optionally substituted with at least one heteroatom or heteroatom-containing moiety. While there is essentially no limitation on the length of the linking group $L_1$, it should be noted that long fatty chains are less desired because they reduce the hydrophilicity of the molecule. Of course, there is essentially no limit in the length of hydrophilic liners, such as polyethylene glycol chains, etc. For example, $L_1$ may be selected from a $C_1$-$C_{30}$ hydrocarbon radical, such as for example, an alkyl, alkenyl, alkynyl, aryl, or alkyl-aryl group, optionally including from 1-20 heteroatoms or heteroatom-containing moieties, such as nitrogen, oxygen, carboxyl, amine and/or carbonyl groups. In some embodiments, $L_1$ may be selected independently at each occurrence from a $C_1$-$C_{20}$, $C_1$-$C_{12}$, $C_1$-$C_6$, $C_1$-$C_4$ or $C_1$-$C_3$ hydrocarbon radical, optionally including from 1-20, 1-10, 1-5, or 1-3 heteroatoms or heteroatom-containing moieties. In other embodiments, $L_1$ may be selected from the group consisting of substituted or unsubstituted branched or straight chain $C_1$-$C_{20}$ alkyl, alkenyl, alkynyl, aryl, or alkyl-aryl groups, each optionally substituted with up to 20 heteroatoms or heteroatom-containing moieties, including without limitation, linear alkyl moieties of the form —$(CH_2)_a$— where "a" is an integer from 1 to 20, including, for example, —$CH_2$—, —$CH_2CH_2$—, —$CH_2CH_2CH_2$—, or —$CH_2CH_2CH_2CH_2$—; linear alkoxy moieties of the general form —$(CH_2)_aO$— or —$O(CH_2)_a$— where "a" is an integer from 1 to 19, including for example,
—$CH_2O$— or —$OCH_2$—, —$CH_2CH_2O$— or —$OCH_2CH_2$—, —$CH_2CH_2CH_2O$— or —$OCH_2CH_2CH_2$—; —$O(CH_2)_aO$— where "a" is as defined above; or a moiety of the form —$(CH_2)_bO(CH_2)_c$—, —$(CH_2)_bS(CH_2)_c$—, or —$(CH_2)_bNR^L(CH_2)_c$— wherein "b" and "c" are independently an integer from 1 to 18 and $R^L$ is an alkyl, alkenyl, alkynyl, aryl, or alkyl-aryl group, each optionally substituted with up to 20 heteroatoms or heteroatom-containing moieties. Preferably, $L_1$ is a divalent $C_{1-20}$ alkyl, alkenyl, alkynyl, aryl, or aralkyl group, optionally substituted with up to 20 heteroatoms or heteroatom-containing moieties.

In other embodiments, $L_1$ may be selected from divalent radicals from $C_{1-10}$ alkyl, each optionally substituted with up to 20 heteroatoms. In another embodiment, $L_1$ is a divalent $C_{1-20}$ alkyl group, more preferably a divalent $C_{1-15}$ alkyl group, even more preferably a divalent $C_{1-10}$ alkyl group, and more preferred still a divalent $C_{1-6}$ alkyl group. In a particular embodiment, $L_1$ is a divalent $C_{1-6}$ alkyl group. In other embodiments, $L_1$ may be a divalent radical of the form —$(CH_2)_n$— where n=1 to 20. Alternatively, n may be 1 to 15, 1 to 12, 1 to 10, 1 to 8, or 1 to 6.

$L_2$ may be present or omitted (in which case it is a bond). The linker $L_2$ is preferably a bond or a short hydrocarbon chain so as to minimize the separation between the anion and cation and thereby preferably maintain substantial charge neutrality, whereas the zwitterions disclosed in U.S. Patent Application No. 2007/0259333 A1 to Dratz et al. have larger charge separations and consequently the anions and cations disclosed in that publication will have more of an isolated charge character. Preferably, $L_2$ is a bond or a divalent $C_{1-6}$ alkyl, alkenyl, alkynyl, aryl, or aralkyl group, optionally substituted with up to 10 heteroatoms, or heteroatom-containing moieties. In one embodiment, $L_2$ is a bond or a divalent $C_1$-$C_6$, $C_1$-$C_5$, $C_1$-$C_4$ or $C_1$-$C_3$ alkyl, alkenyl, alkynyl, aryl, or aralkyl group, optionally substituted with up to 10, 8, 4 or 2 heteroatoms, or heteroatom-containing moieties. In another embodiment, $L_2$ is a bond or a divalent $C_2$ alkyl, alkenyl, or alkynyl group, optionally substituted with up to 4 heteroatoms, or heteroatom-containing moieties. In another embodiment, $L_2$ is a bond or a divalent $C_1$-$C_6$, $C_1$-$C_5$, $C_1$-$C_4$ or $C_1$-$C_3$ alkyl group, optionally substituted with up to 10, 8, 4 or 2 heteroatoms, or heteroatom-containing moieties. In a particular embodiment, $L_2$ is a divalent $C_{1-4}$ alkyl group. In other embodiments, $L_2$ may be a divalent radical of the form —$(CH_2)_m$— where m=1 to 6, preferably 1 to 4, and more preferably 2 to 4.

Alternatively, $L_2$ may be selected from the group consisting of substituted or unsubstituted branched or straight chain $C_1$-$C_{20}$ alkyl, alkenyl, alkynyl, aryl, or alkyl-aryl groups, each optionally substituted with up to 20 heteroatoms or heteroatom-containing moieties.

$R_1$ and $R_2$ may independently represent any hydrocarbon moiety, optionally substituted with at least one heteroatom or heteroatom moiety. For example, $R_1$ and/or $R_2$ may be independently selected at each occurrence from a $C_1$-$C_{30}$ hydrocarbon radical, such as for example, an alkyl, alkenyl, alkynyl, aryl, or alkyl-aryl group, optionally including from 1-20 heteroatoms or heteroatom-containing moieties, such as nitrogen, oxygen, carboxyl, amine and/or carbonyl groups. In some embodiments, $R_1$ and/or $R_2$ may be selected independently at each occurrence from a $C_1$-$C_{20}$, $C_1$-$C_{12}$, $C_1$-$C_6$, or $C_1$-$C_4$ hydrocarbon radical, optionally including from 1-20, 1-10, 1-5, or 1-3 heteroatoms or heteroatom-containing moieties. In one exemplary embodiment, $R_1$ and/or $R_2$ may be substituted or unsubstituted branched or straight chain $C_{1-20}$ hydrocarbon moieties, such as, for example, an alkyl, alkenyl, alkynyl, aryl, or aralkyl groups, each optionally substituted with up to 20 heteroatoms or heteroatom-containing moieties. In other exemplary embodiments, $R_1$ and $R_2$ are independently selected at each occurrence from $C_{1-15}$ alkyl, alkenyl, alkynyl, aryl, or aralkyl groups, each optionally substituted with up to 20 heteroatoms. Preferably, $R_1$ and $R_2$ are independently selected at each occurrence from $C_{1-15}$ alkyl groups, more preferably from $C_{1-10}$ alkyl groups. In certain specific embodiments, $R_1$ and $R_2$ is at one occurrence or at both a $C_{1-6}$ alkyl group. In other embodiment, at least one of $R_1$ and $R_2$ is methyl, ethyl, propyl, isopropyl, cyclopropyl, butyl, secbutyl, isobutyl, tertbutyl, cyclobutyl, 1-methylbutyl, 1,1-dimethylpropyl, pentyl, cyclopentyl, isopentyl, neopentyl, cyclopentyl, hexyl, isohexyl, and cyclohexyl, which may be unsubstituted or substituted with one or more heteroatoms or heteroatom moieties selected from the group consisting of halogen, hydroxyl, carboxyl, acyl, acyloxy, amino, alkylamino, alkylimino, dialkylamino, arylamino, amido, ester, carboxamide, carbamate, alkoxyl, aryloxyl, alkylthiol, alkylsulfonate, nitro, cyano, oxo, oxa, azo, thio, sulfonyl, ester, phosphonyl, phosphinyl, thiol, thioether, thioester, thioalkoxy, thiocyanate, perfluoro, phosphate, oxime, sulfate, sulfo-alkyl, combinations thereof or any other functional group that does not inhibit the reactivity of this compound for forming a conjugate with a hydrophobic molecule, preferably a peptide, protein or macromolecule. Preferred substitutions include nitrogen, oxygen, carboxyl, amine and/or carbonyl groups. In an exemplary embodiment, at least one of $R_1$ and $R_2$ is a methyl group. In another embodiment, both $R_1$ and $R_2$ are methyl groups.

In one embodiment, the zwitterion-containing compound of Formula (I) has the structure:

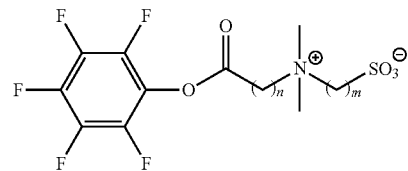

where, n=1 to 6, preferably 1 to 4, and more preferably, 2 to 4; and m=1 to 6, preferably 1 to 4, and more preferably 2 to 4.

In another embodiment, the zwitterion-containing compound of Formula (I) has the structure:

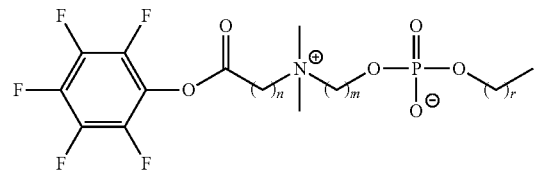

where, n=1 to 6, preferably 1 to 4, and more preferably, 2 to 4;

m=1 to 6, preferably 1 to 4, and more preferably, 2 to 4; and r=1 to 6, preferably 1 to 4, and more preferably, 2 to 4.

In another embodiment, the zwitterion-containing compound of Formula (I) has the structure:

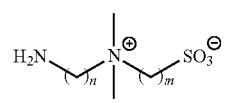

where, n=1 to 6, preferably 1 to 4, and more preferably, 2 to 4; and m=1 to 6, preferably 1 to 4, and more preferably 2 to 4.

In another embodiment, the zwitterion-containing compound of Formula (I) has the structure:

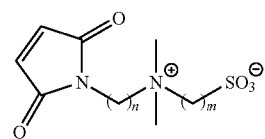

where, n=1 to 6, preferably 1 to 4, and more preferably, 2 to 4; and m=1 to 6, preferably 1 to 4, and more preferably 2 to 4.

In another embodiment, the zwitterion-containing compound of Formula (I) has the structure:

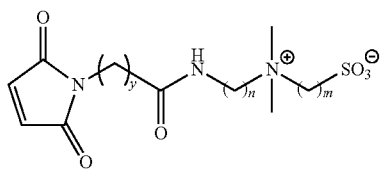

where, n=1 to 6, preferably 1 to 4, and more preferably, 2 to 4;
m=1 to 6, preferably 1 to 4, and more preferably, 2 to 4; and
y=1 to 6, preferably 2 to 5, and more preferably, 3 to 5.

In one particular embodiment, the zwitterion-containing compound of Formula I may be used in a method for improving the aqueous solubility of a peptide, protein or macromolecule. The method may comprise attaching the zwitterion-containing compound to the peptide, protein or macromolecule. In particular, the zwitterion-containing compound may form covalently linkages with the peptide, protein or macromolecule. Specifically, the $Y_1$ moiety may form covalently linkages with reactive groups, such as, for example, an amine group, a thiol group, or a carbohydrate group, within the peptide, protein or macromolecule.

In another embodiment, the zwitterion-containing compound of Formula I may be used in a method of reducing non-specific binding of an analyte, analyte analog, or binding partner for an analyte in a biologic binding assay. The method may comprise attaching the zwitterion-containing compound to the peptide, protein or macromolecule. In particular, the zwitterion-containing compound may form covalently linkages with the analyte, analyte analog, or binding partner for an analyte. Specifically, the $Y_1$ moiety may form covalently linkages with reactive groups, such as, for example, an amine group, a thiol group, or a carbohydrate group, within the analyte, analyte analog, or binding partner for an analyte.

Exemplary embodiments of zwitterion-containing compounds for the modification of hydrophobic molecules, for example, peptides, proteins and other macromolecules are provided in FIG. 1. The compounds Z2-PFP (compound 1d), Z3-PFP (compound 2c), Z4-PFP (compound 3c) and ZPB-PFP (compound 4c, ZPB=Zwitterion Phosphobetaine) are amine-reactive zwitterion compounds with sulfobetaines or a phosphobetaine, as well as a reactive pentafluorophenyl (PFP) ester. The three sulfobetaines Z2-PFP, Z3-PFP and Z4-PFP have increasing charge separation between the quarternary ammonium and the sulfonate moieties that constitute the zwitterion. The syntheses of these amine reactive zwitterion labels are described in detail in Examples 1-4.

FIG. 1 also provides a zwitterion compound with a nucleophilic amine moiety (compound 5c) that is useful for coupling to carboxylic acid moieties as well as two thiol-reactive zwitterion labels Z-maleimide-1 (compound 6b) and Z-maleimide-2 (compound 7a). The thiol-reactive zwitterion labels are useful for capping free thiols in proteins and peptides thereby preventing their oxidation and aggregation while at the same time improving their aqueous solubility.

In another embodiment, the zwitterion-containing compounds according to the invention may serve as zwitterionic linkers for the modification of a detectable label, for example, labels used in a biologic binding assay for labeling an analyte, analyte analog or binding partner for an analyte, such as, for example, a fluorescent label, a chemiluminescent label, biotin, etc., to improve their solubility and for the synthesis of conjugates with increased aqueous solubility. Particular mention for a detectable label is made of a fluorescent label (e.g., fluorescein) and biotin. In one embodiment, the zwitterion-containing compounds may comprise (i) a negatively charged group linked by a bond or a hydrocarbon moiety, optionally substituted with up to 20 heteroatoms, to the nitrogen atom of a quaternary ammonium; (ii) an electrophilic, nucleophilic or photoreactive group linked by a hydrocarbon moiety, optionally substituted with up to 20 heteroatoms, to the nitrogen atom of the quaternary ammonium; and (iii) a fluorescent label or biotin linked by a hydrocarbon moiety, optionally substituted with up to 20 heteroatoms, to the nitrogen atom of a quaternary ammonium. The negatively charged group linked to the nitrogen atom may together constitute a zwitterionic group, for example, in the case of a sulfobetaine, there is a positive charge on the quarternary nitrogen and a negative charge on the $—SO_3$ group, which is linked to the quarternary nitrogen by a divalent alkyl moiety. The hydrocarbon moiety linking the electrophilic, nucleophilic or photoreactive group to the nitrogen atom preferably comprises a divalent alkyl, alkenyl, alkynyl, aryl, or aralkyl group. More preferably, the hydrocarbon moiety linking the electrophilic, nucleophilic or photoreactive group to the nitrogen atom comprises a divalent radical from $C_{1-6}$ alkyl, alkenyl, alkynyl, aryl, or aralkyl group.

In one embodiment, the zwitterion-containing compound for labeling an analyte, analyte analog, or binding partner for an analyte has the following structure shown in Formula II:

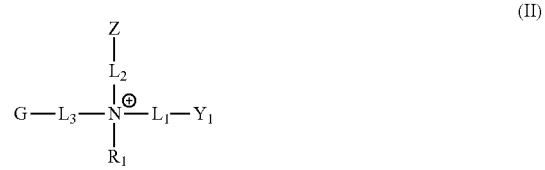

(II)

G may be any detectable label. More particularly, G may be any detectable label suitable for biologic assays. In some embodiments, G is selected from a fluorescent label, a chemiluminescent label or biotin. Preferably, G is a fluorescent label, for example, fluorescein. Particular mention is made where the detectable label is biotin.

$L_3$ may be any divalent hydrocarbon moiety, optionally substituted with at least one heteroatom or heteroatom-containing moiety. While there is essentially no limitation on the length of the linking group $L_3$, it is also subject to the same considerations of hydrophilicity discussed with respect to $L_1$. For example, $L_3$ may be selected from a $C_1$-$C_{30}$ hydrocarbon radical, such as for example, an alkyl, alkenyl, alkynyl, aryl, or alkyl-aryl group, optionally including from 1-20 heteroatoms or heteroatom-containing moieties, such as nitrogen, oxygen, carboxyl, amine and/or carbonyl groups. In some embodiments, $L_3$ may be selected independently at each occurrence from a $C_1$-$C_{20}$, $C_1$-$C_{12}$, $C_1$-$C_6$, $C_1$-$C_4$ or $C_1$-$C_3$ hydrocarbon radical, optionally including from 1-20, 1-10, 1-5, or 1-3 heteroatoms or heteroatom-containing moieties. In other embodiments, $L_3$ may be selected from the group consisting of substituted or unsubstituted branched or straight chain $C_1$-$C_{20}$ alkyl, alkenyl, alkynyl, aryl, or alkyl-aryl groups, each optionally substituted with up to 20 heteroatoms or heteroatom-containing moieties.

In certain embodiments, $L_3$ may be a group —$X^G$—$R^G$—, where $X^G$ is attached to G, and $X^G$ is a bond or a linker moiety, such as for example, oxygen, sulfur, amine, amide (—C(O)NR$^N$— or —NR$^N$—C(O)—), ester (—C(O)—O— or —O—C(O)—), carbamate (—NR$^N$—C(O)—O— or —O—C(O)-NR$^N$—) or urea (—NR$^N$—C(O)—NR$^N$—), and R$^N$ may be hydrogen or any hydrocarbon moiety, for example, a $C_{1-20}$, $C_1$-$C_{12}$, $C_1$-$C_6$, or $C_1$-$C_4$ alkyl, alkenyl, alkynyl, aryl, or aralkyl, optionally substituted with up to 3, 5, 10 or 20 heteroatoms. In some embodiments, R$^N$ may be, for example, hydrogen or a $C_{1-20}$ alkyl, alkenyl, alkynyl, aryl, or aralkyl, optionally substituted with up to 20 heteroatoms, such as oxygen, sulfur, and nitrogen atoms; where R$^N$ is preferably selected from substituted or unsubstituted, branched, straight chain or cyclic, $C_1$-$C_{20}$ alkyl, alkenyl, alkynyl, aryl, benzyl, heteroaryl, alkyl-aryl, aryl-alkyl, alkyl-heteroaryl, heteroaryl-alkyl, heteroaryl-aryl, aryl-heteroaryl, bicyclic alkyl, aryl, or heteroaryl radicals, and combinations thereof, and wherein each of the foregoing radicals may be substituted with 1-20 heteroatoms and/or with any heteroatom-containing moiety, including, for example, acyl, acyloxy, amino, alkoxyl, alkylamino, alkylthiol, alkylimino, alkylsulfonate, amide, azo, carboxyl, carboxamide, carbamide, cyano, dialkylamino, ester, halogen, hydroxyl, nitro, oxo, oxa, oxime, perfluoro, phosphate, phosphonyl, phosphinyl, sulfate, sulfate, sulfo-alkyl, thiol, thioether, thioester, thioalkoxy, thiocyanate, and combinations thereof. Preferably, R$^N$ is a $C_{1-15}$ alkyl, a $C_{1-12}$ alkyl, a $C_{1-10}$ alkyl, a $C_{1-6}$ alkyl, or a $C_{1-4}$ alkyl. In specific embodiments, R$^N$ is a methylene group.

R$^G$ may be any divalent hydrocarbon moiety, optionally substituted with at least one heteroatom or heteroatom-containing moiety. For example, R$^G$ may be selected from a $C_1$-$C_{30}$ hydrocarbon radical, such as for example, an alkyl, alkenyl, alkynyl, aryl, or alkyl-aryl group, optionally including from 1-20 heteroatoms or heteroatom-containing moieties, such as nitrogen, oxygen, carboxyl, amine and/or carbonyl groups. In some embodiments, R$^G$ may be selected independently at each occurrence from a $C_1$-$C_{20}$, $C_1$-$C_{12}$, $C_1$-$C_6$, $C_1$-$C_4$ or $C_1$-$C_3$ hydrocarbon radical, optionally including from 1-20, 1-10, 1-5, or 1-3 heteroatoms or heteroatom-containing moieties. In other embodiments, R$^G$ may be selected from the group consisting of substituted or unsubstituted branched or straight chain $C_1$-$C_{20}$ alkyl, alkenyl, alkynyl, aryl, or alkyl-aryl groups, each optionally substituted with up to 20 heteroatoms or heteroatom-containing moieties, including without limitation, linear alkyl moieties of the form
—(CH$_2$)$_a$— where "a" is an integer from 1 to 20, including, for example, —CH$_2$—, —CH$_2$CH$_2$—, —CH$_2$CH$_2$CH$_2$—, or —CH$_2$CH$_2$CH$_2$CH$_2$—; linear alkoxy moieties of the general form —(CH$_2$)$_a$O— or —O(CH$_2$)$_a$— where "a" is an integer from 1 to 19, including for example,
—CH$_2$O— or —OCH$_2$—, —CH$_2$CH$_2$O— or —OCH$_2$CH$_2$—, —CH$_2$CH$_2$CH$_2$O— or —OCH$_2$CH$_2$CH$_2$—; —O(CH$_2$)$_a$O— where "a" is as defined above; or a moiety of the form —(CH$_2$)$_b$O(CH$_2$)$_c$—, —(CH$_2$)$_b$S(CH$_2$)$_c$—, or —(CH$_2$)$_b$NR$^L$(CH$_2$)$_c$— wherein "b" and "c" are independently an integer from 1 to 18 and R$^L$ is an alkyl, alkenyl, alkynyl, aryl, or alkyl-aryl group, each optionally substituted with up to 20 heteroatoms or heteroatom-containing moieties.

In other embodiments, R$^G$ is a divalent radical from $C_{1-10}$ alkyl, each optionally substituted with up to 20 heteroatoms. In another embodiment, R$^G$ is a divalent $C_{1-15}$ alkyl group, more preferably a divalent $C_{1-10}$ alkyl group, even more preferably a divalent $C_{1-6}$ alkyl group and more preferred still a divalent $C_{1-4}$ alkyl group. In certain embodiments, R$^G$ is a methylene group. In other embodiments, R$^G$ may be a divalent radical of the form —(CH$_2$)$_g$— where g=1 to 15. Alternatively, g may be 1 to 10, 1 to 8, 1 to 6 or 1 to 4.

It will be understood the selection of substituents $L_1$, $L_2$, $R_1$, $Z$, $Y_1$, etc., including the preferences therefore, defined in connection with Formula I, apply equally to the selection of comparable parameters in accordance with Formula II.

In one embodiment, the zwitterion-containing compound of Formula (II) has the structure:

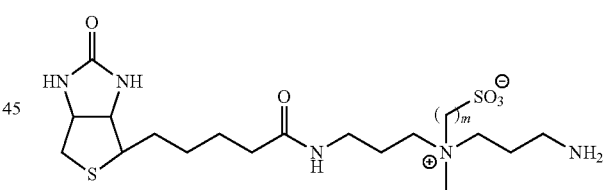

where m=1 to 6, preferably 1 to 4, and more preferably, 2 to 4.

In another embodiment, the zwitterion-containing compound of Formula (II) has the structure:

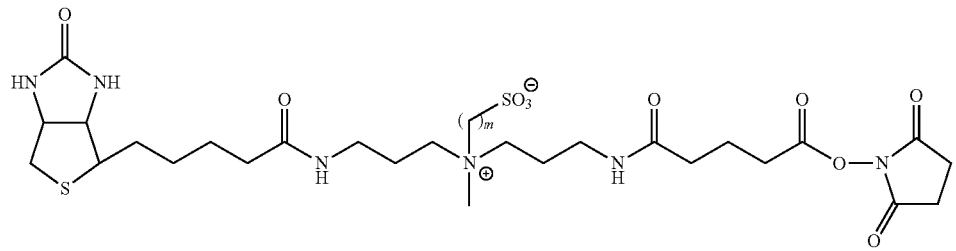

where m=1 to 6, preferably 1 to 4, and more preferably, 2 to 4.

In another embodiment, the zwitterion-containing compound of Formula (II) has the structure:

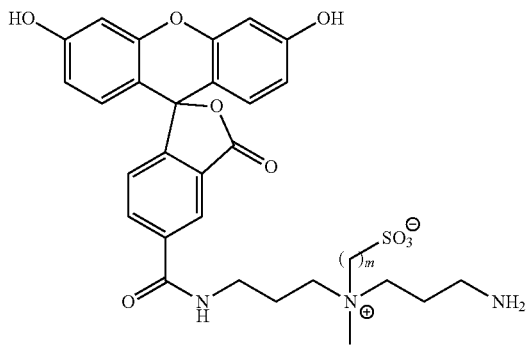

where m=1 to 6, preferably 1 to 4, and more preferably, 2 to 4.

In another embodiment, the zwitterion-containing compound of Formula (II) has the structure:

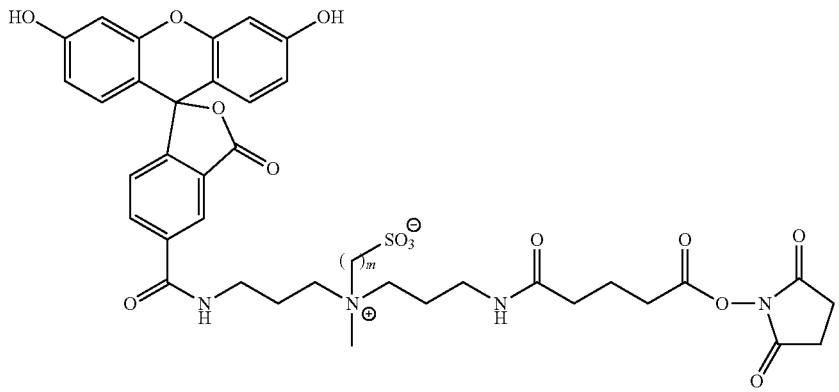

where m=1 to 6, preferably 1 to 4, and more preferably, 2 to 4.

In one particular embodiment, the zwitterion-containing compound of Formula II may be used in a method of labeling an analyte, analyte analog, or binding partner for an analyte in a biologic binding assay. The method may comprise attaching the zwitterion-containing compound to the peptide, protein or macromolecule. In particular, the zwitterion-containing compound may form covalently linkages with the analyte, analyte analog, or binding partner for an analyte. Specifically, the $Y_1$ moiety may form covalently linkages with reactive groups, such as, for example, an amine group, a thiol group, or a carbohydrate group, within the analyte, analyte analog, or binding partner for an analyte.

Exemplary embodiments of zwitterion-containing compounds according to the invention for labeling an analyte, analyte analog, or binding partner for an analyte for a biologic binding assay may improve the solubility of the analyte, analyte analog, or binding partner for an analyte or promote the synthesis of labeled conjugates with increased aqueous solubility. Exemplary embodiments where the moiety comprising the detectable label is either fluorescein or biotin are provided in FIGS. 2a and 2b. The compounds biotin-Z—$NH_2$ (compound 10a) and fluorescein-Z—$NH_2$ (compound 11a) contain zwitterionic sulfobetaine linkers and a nucleophilic amine moiety useful for coupling to carboxylic acids. The compounds biotin-Z-NHS (compound 10c) and fluorescein-Z—NHS (compound 11c) contain the same sulfobetaine zwitterion linker except that both these compounds contain amine-reactive N-hydroxsuccinimide (NHS esters). The biotin-streptavidin and the fluorescein-anti fluorescein antibody binding interactions are may be used to devise immunoassays. For example, streptavidin or an anti-fluorescein antibody can be immobilized on a solid phase such as a microparticle and a biotin-labeled or fluorescein-labeled molecule can be captured onto the solid phase during the course of an immunoassay. If the labeled molecule is hydrophobic then alleviating its aqueous solubility with a zwitterionic, biotin or fluorescein derivative is likely to improve assay performance by lowering non-specific binding. Two examples of such conjugates are illustrated in FIG. 2b which shows the structures of zwitterionic, fluorescein conjugates of progesterone (11d), a steroid and FK506 (11e), an immunosuppressive drug. Both progesterone and FK506 are hydrophobic analytes are exemplary analytes that are suitable for measuring or quantification in immunoassays.

In yet another embodiment, the zwitterion-containing compounds according to the invention may be suitable for cross-linking hydrophobic molecules, particularly in the aqueous solvents. The zwitterion-containing compounds may also lower the non-specific binding of the crosslinked conjugates in a solid phase as compared to otherwise hydrophobic molecules not crosslinked by said zwitterion-containing compound. In certain embodiments, the hydrophobic molecule may be selected from a group consisting of peptides, proteins or macromolecules. In one embodiment, the zwitterion-containing compounds may comprise (i) a negatively charged group linked by a bond or a hydrocarbon moiety, optionally substituted with up to 20 heteroatoms, to the nitrogen atom of a quaternary ammonium; and (ii) two electrophilic, nucleophilic or photoreactive groups, which can be the same or different, linked to the nitrogen atom of the quaternary ammonium. In some embodiments, the electrophilic, nucleophilic or photoreactive groups may be linked to the nitrogen atom by a hydrocarbon moiety, optionally substituted with up to 20 heteroatoms. In other embodiments, the electrophilic, nucleophilic or photoreactive groups may be linked to each other by a hydrocarbon moiety, optionally substituted with up to 20 heteroatoms, which is in turn linked to the nitrogen atom by a bond or a hydrocarbon moiety, optionally substituted with up to 20 heteroatoms. The negatively charged group linked to the nitrogen atom may together constitute a zwitterionic group, for example, in the case of a sulfobetaine, there is a positive charge on the quarternary nitrogen and a negative charge on the —$SO_3$ group, which is linked to the quarternary nitrogen by a divalent alkyl moiety. The hydrocarbon moieties linking the electrophilic, nucleophilic or photoreactive groups to the nitrogen atom preferably comprises divalent alkyl, alkenyl, alkynyl, aryl, or aralkyl groups. More preferably, the hydrocarbon moieties linking the electrophilic, nucleophilic or photoreactive groups to the nitrogen atom comprises divalent radicals from $C_{1-6}$ alkyl, alkenyl, alkynyl, aryl, or aralkyl group.

Most commercial cross-linking reagents tend to be hydrophobic, but may be PEG-modified, having oligo(ethylene) glycol linkers, to provide limited improvements in aqueous solubility. Zwitterionic cross-linking agents of the present invention however are likely to be much more polar with excellent aqueous solubility because of the strongly hydrophilic nature of zwitterions.

In another embodiment, the zwitterion-containing compound may be useful for cross-linking biologic molecules, including but not limited to an analyte, analyte analog, or a binding partner in a biologic binding assay for the determination or quantitation of analytes, as described above. It is contemplated that the zwitterion-containing compound may be suitable for cross-linking any two biologic molecules, which may be the same or different. Biologic molecules for cross-linking by the zwitterion-containing compound of the present invention include, for example: (a) small organic biomolecules, haptens or ligands such as thyroid hormones, steroids, vitamins, antibiotics, enzyme cofactors, therapeutic drugs, metabolites, lipids, neurotransmitters, or controlled chemical substances, (b) macromolecules such as bioactive proteins (including avidin, antibodies, DNA binding proteins, enzymes, histones, and others), polysaccharides, oligosaccharides, glycoproteins, glycosamino glycans, lectins, lipoproteins, lipopolysaccharides, isolated or intact RNA, DNA, oligonucleotides, proteins, peptides, inactivated proteins, hormones, viral antigens, bacterial antigens, eukaryotic antigens, immunoglobulin binding proteins, toxins, cytokines, antibody fragments, or receptor proteins, (c) higher order biological entities such as viruses, bacteria, eukaryotic cells, and subcellular components such as ribosomes, amongst others.

In one embodiment, the zwitterion-containing compound for cross-linking peptides, proteins, and/or macromolecules has the structure of formula (III):

$Y_1$-Ω-$Y_2$         (III)

wherein,

Ω is a zwitterion-containing group of the form

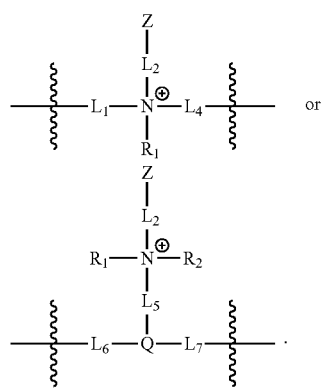

$Y_1$ and $Y_2$ may comprise any suitable reactive functional group for forming covalent linkages with a hydrophobic molecule, such as, for example, a peptide, a protein, or a macromolecule. More particularly, $Y_1$ and/or $Y_2$ may comprise any electrophilic, nucleophilic or photoreactive group suitable for forming a conjugate with a hydrophobic molecule. For example, $Y_1$ and/or $Y_2$ may comprise a reactive functional group for forming covalently linkages with an analyte, analyte analog, or a binding partner for an analyte in a biologic binding assay for the determination or quantitation of analytes. In certain embodiments, wherein $Y_1$ and/or $Y_2$ are independently selected at each occurrence from an amine-reactive group, a thiol-reactive group, a carboxy-reactive group, a maleimidyl-reactive group, a carbohydrate-reactive group, or a photoreactive-group. More particularly, suitable functional groups for $Y_1$ and $Y_2$ may be may include, for example:

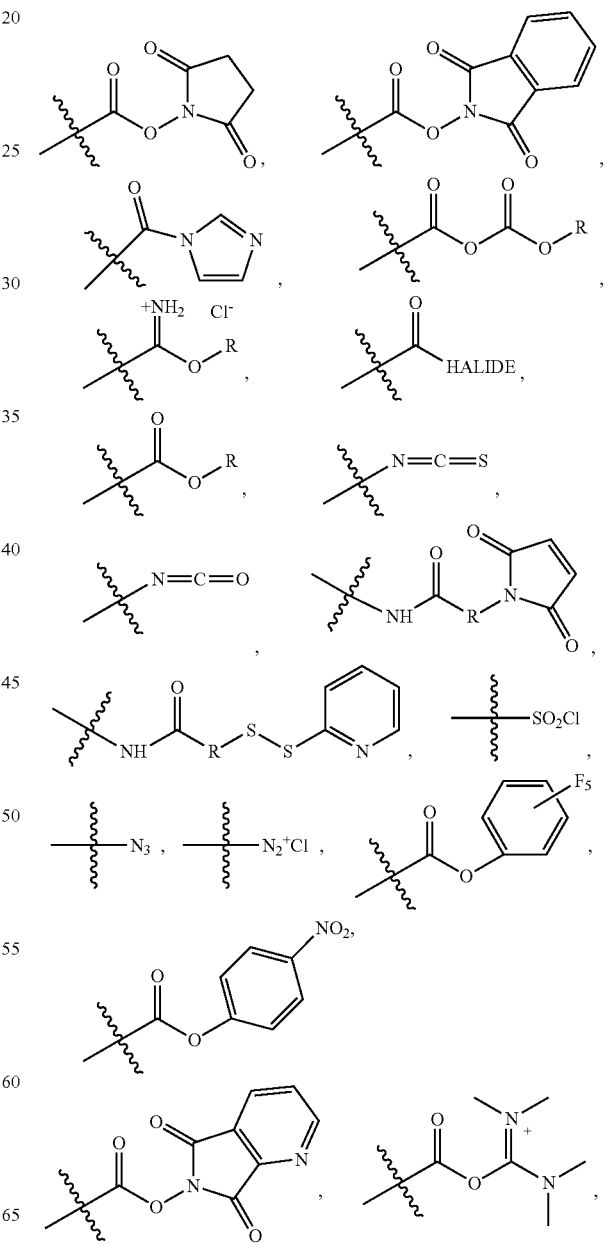

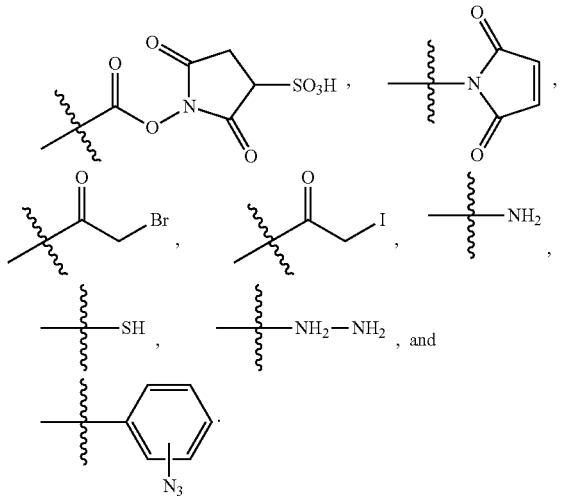

In certain preferred embodiments, $Y_1$ or $Y_2$ is, at one occurrence, a pentafluorophenyl (PFP) ester, maleimide, amine, or N-succinimidyloxycarbonyl.

In some embodiments, if the zwitterion-containing compound comprises two electrophilic groups that are the same, for example, such as both $Y_1$ and $Y_2$ are N-hydroxysuccinimide esters or both $Y_1$ and $Y_2$ are maleimides, the reagents are referred to as homo-bifunctional cross-linkers. Homo-bifunctional cross-linking reagents can also be comprised of two nucleophilic groups or two photoreactive groups. On the other hand, hetero-bifunctional cross-linkers typically contain an amine reactive functional group such an N-hydroxysuccinimide group and a thiol-reactive functional group such as a maleimide or iodoacetamide moiety. They can also contain either an amine-reactive, a thiol-reactive, a carboxy-reactive, a maleimidyl-reactive, or a carbohydrate-reactive moiety and a photoreactive moiety. For example, aryl azides may be used as non-selective, photoreactive functional groups.

$L_4$ may be any divalent hydrocarbon moiety, optionally substituted with at least one heteroatom or heteroatom-containing moiety. While there is essentially no limitation on the length of the linking group $L_4$, it is also subject to the same considerations of hydrophilicity discussed with respect to $L_1$. For example, $L_4$ may be selected from a $C_1$-$C_{30}$ hydrocarbon radical, such as for example, an alkyl, alkenyl, alkynyl, aryl, or alkyl-aryl group, optionally including from 1-20 heteroatoms or heteroatom-containing moieties, such as nitrogen, oxygen, carboxyl, amine and/or carbonyl groups. In some embodiments, $L_4$ may be selected independently at each occurrence from a $C_1$-$C_{20}$, $C_1$-$C_{12}$, $C_1$-$C_6$, $C_1$-$C_4$ or $C_1$-$C_3$ hydrocarbon radical, optionally including from 1-20, 1-10, 1-5, or 1-3 heteroatoms or heteroatom-containing moieties. In other embodiments, $L_4$ may be selected from the group consisting of substituted or unsubstituted branched or straight chain $C_1$-$C_{20}$ alkyl, alkenyl, alkynyl, aryl, or alkyl-aryl groups, each optionally substituted with up to 20 heteroatoms or heteroatom-containing moieties, including without limitation, linear alkyl moieties of the form
—$(CH_2)_a$— where "a" is an integer from 1 to 20, including, for example, —$CH_2$—, —$CH_2CH_2$—, —$CH_2CH_2CH_2$—, or —$CH_2CH_2CH_2CH_2$—; linear alkoxy moieties of the general form —$(CH_2)_aO$— or —$O(CH_2)_a$— where "a" is an integer from 1 to 19, including for example,
—$CH_2O$— or —$OCH_2$—, —$CH_2CH_2O$— or —$OCH_2CH_2$—, —$CH_2CH_2CH_2O$— or —$OCH_2CH_2CH_2$—; —$O(CH_2)_aO$— where "a" is as defined above; or a moiety of the form —$(CH_2)_bO(CH_2)_c$—, —$(CH_2)_bS(CH_2)_c$—, or —$(CH_2)_bNR^L(CH_2)_c$— wherein "b" and "c" are independently an integer from 1 to 18 and $R^L$ is an alkyl, alkenyl, alkynyl, aryl, or alkyl-aryl group, each optionally substituted with up to 20 heteroatoms or heteroatom-containing moieties. Preferably, $L_4$ is a divalent $C_{1-20}$ alkyl, alkenyl, alkynyl, aryl, or aralkyl group, optionally substituted with up to 20 heteroatoms or heteroatom-containing moieties.

In other embodiments, $L_4$ may be selected from divalent radicals from $C_{1-10}$ alkyl, each optionally substituted with up to 20 heteroatoms. In another embodiment, $L_4$ is a divalent $C_{1-20}$ alkyl group, more preferably a divalent $C_{1-15}$ alkyl group, even more preferably a divalent $C_{1-10}$ alkyl group, and more preferred still a divalent $C_{1-6}$ alkyl group. In a particular embodiment, $L_4$ is a divalent $C_{1-6}$ alkyl group. In other embodiments, $L_4$ may be a divalent radical of the form —$(CH_2)_p$— where p=1 to 20. Alternatively, p may be 1 to 15, 1 to 12, 1 to 10, 1 to 8, or 1 to 6.

$L_5$, $L_6$, and/or $L_7$ may be present or omitted (in which case it is a bond). However, as further discussed below, when Q is nitrogen, $L_5$, $L_6$, and $L_7$ are each not a bond. $L_5$, $L_6$, and/or $L_7$, where present may be any divalent hydrocarbon moiety, optionally substituted with at least one heteroatom or heteroatom-containing moiety. While there is essentially no limitation on the lengths of the linking groups $L_5$, $L_6$, and $L_7$, they are also subject to the same considerations of hydrophilicity discussed with respect to $L_1$. For example, $L_5$, $L_6$, and/or $L_7$ may be selected from a $C_1$-$C_{30}$ hydrocarbon radical, such as for example, an alkyl, alkenyl, alkynyl, aryl, or alkyl-aryl group, optionally including from 1-20 heteroatoms or heteroatom-containing moieties, such as nitrogen, oxygen, carboxyl, amine and/or carbonyl groups. In some embodiments, $L_5$, $L_6$, and/or $L_7$ may be selected independently at each occurrence from a $C_1$-$C_{20}$, $C_1$-$C_{12}$, $C_1$-$C_6$, $C_1$-$C_4$ or $C_1$-$C_3$ hydrocarbon radical, optionally including from 1-20, 1-10, 1-5, or 1-3 heteroatoms or heteroatom-containing moieties. In other embodiments, $L_5$, $L_6$, and/or $L_7$ may be selected from the group consisting of substituted or unsubstituted branched or straight chain $C_1$-$C_{20}$ alkyl, alkenyl, alkynyl, aryl, or alkyl-aryl groups, each optionally substituted with up to 20 heteroatoms or heteroatom-containing moieties.

In some embodiments, $L_5$, $L_6$ and/or $L_7$ may be a group —$X_a$—$R^a$—, where $X^a$ is attached to Q and is independently selected at each occurrence from a bond or a linker moiety, such as for example, oxygen, sulfur, amine, amide (—C(O)NR$^N$— or —NR$^N$—C(O)—), ester (—C(O)—O— or —O—C(O)—), carbamate (—NR$^N$—C(O)—O— or —O—C(O)—NR$^N$—) or urea (—NR$^N$—C(O)—NR$^N$—), and $R^N$ may be hydrogen or any hydrocarbon moiety, for example, a $C_{1-20}$, $C_1$-$C_{12}$, $C_1$-$C_6$, or $C_1$-$C_4$ alkyl, alkenyl, alkynyl, aryl, or aralkyl, optionally substituted with up to 3, 5, 10 or 20 heteroatoms. In some embodiments, $R^N$ may be, for example, hydrogen or a $C_{1-20}$ alkyl, alkenyl, alkynyl, aryl, or aralkyl, optionally substituted with up to 20 heteroatoms, such as oxygen, sulfur, and nitrogen atoms; where $R^N$ is preferably selected from substituted or unsubstituted, branched, straight chain or cyclic, $C_1$-$C_{20}$ alkyl, alkenyl, alkynyl, aryl, benzyl, heteroaryl, alkyl-aryl, aryl-alkyl, alkyl-heteroaryl, heteroaryl-alkyl, heteroaryl-aryl, aryl-heteroaryl, bicyclic alkyl, aryl, or heteroaryl radicals, and combinations thereof; and wherein each of the foregoing radicals may be substituted with 1-20 heteroatoms and/or with any heteroatom-containing moiety, including, for example, acyl, acyloxy, amino, alkoxyl, alkylamino, alkylthiol, alkylimino, alkylsulfonate, amide, azo, carboxyl, carboxamide, carbamide, cyano, dialkylamino, ester, halogen, hydroxyl, nitro, oxo, oxa, oxime, perfluoro, phosphate, phosphonyl, phosphinyl, sulfate, sulfate, sulfo-alkyl, thiol, thioether, thioester, thioalkoxy, thiocyanate, and combinations thereof. Preferably, $R^N$ is a $C_{1-15}$ alkyl, a $C_{1-12}$ alkyl, a $C_{1-10}$ alkyl, a $C_{1-6}$ alkyl, or a $C_{1-4}$ alkyl. In specific embodiments, $R^N$ is a methylene group. Particular mention is made where $X^a$ is, at one or more occurrences, an amine or amide (—C(O)NR$^N$— or —NR$^N$—C(O)—) and Q is carbon.

$R^a$ may be any divalent hydrocarbon moiety, optionally substituted with at least one heteroatom or heteroatom-containing moiety. For example, $R^a$ may be selected independently at each occurrence from a $C_1$-$C_{30}$ hydrocarbon radical, such as for example, an alkyl, alkenyl, alkynyl, aryl, or alkyl-aryl group, optionally including from 1-20 heteroatoms or heteroatom-containing moieties, such as nitrogen, oxygen, carboxyl, amine and/or carbonyl groups. In some embodiments, $R^a$ may be selected independently at each occurrence from hydrogen or a $C_1$-$C_{20}$, $C_1$-$C_{12}$, $C_1$-$C_6$, $C_1$-$C_4$, or $C_1$-$C_3$ hydrocarbon radical, optionally including from 1-20, 1-10, 1-5, or 1-3 heteroatoms or heteroatom-containing moieties. Preferably, $R^a$ is selected from a bond or divalent $C_{1-15}$ alkyl, alkenyl, alkynyl, aryl, or aralkyl groups, each optionally substituted with up to 20 heteroatoms. In other embodiments, $R^a$ may be selected from the group consisting of substituted or unsubstituted branched or straight chain $C_1$-$C_{20}$ alkyl, alkenyl, alkynyl, aryl, or alkyl-aryl groups, each optionally substituted with up to 20 heteroatoms, including without limitation, linear alkyl moieties of the form —(CH$_2$)$_a$— where "a" is an integer from 1 to 20, including, for example, —CH$_2$—, —CH$_2$CH$_2$—, —CH$_2$CH$_2$CH$_2$—, or —CH$_2$CH$_2$CH$_2$CH$_2$—; linear alkoxy moieties of the general form —(CH$_2$)$_a$O— or —O(CH$_2$)$_a$— where "a" is an integer from 1 to 19, including for example, —CH$_2$O— or —OCH$_2$—, —CH$_2$CH$_2$O— or —OCH$_2$CH$_2$—, —CH$_2$CH$_2$CH$_2$O— or —OCH$_2$CH$_2$CH$_2$—; —O(CH$_2$)$_a$O— where "a" is as defined above; or a moiety of the form —(CH$_2$)$_b$O(CH$_2$)$_c$—, —(CH$_2$)$_b$S(CH$_2$)$_c$—, or —(CH$_2$)$_b$NR$^L$(CH$_2$)$_c$— wherein "b" and "c" are independently an integer from 1 to 18 and $R^L$ is an alkyl, alkenyl, alkynyl, aryl, or alkyl-aryl group, each optionally substituted with up to 20 heteroatoms.

In other embodiments, $R^a$ is a divalent radical from $C_{1-10}$ alkyl, each optionally substituted with up to 20 heteroatoms. In another embodiment, $R^a$ is a divalent $C_{1-15}$ alkyl group, more preferably a divalent $C_{1-10}$ alkyl group, even more preferably a divalent $C_{1-6}$ alkyl group and more preferred still a divalent $C_{1-4}$ alkyl group. In certain embodiments, $R^a$ is a methylene group. In other embodiments, $R^a$ may be a divalent radical of the form —(CH$_2$)$_q$— where q=1 to 15. Alternatively, q may be 1 to 10, 1 to 8, 1 to 6 or 1 to 4.

Q may be any suitable trivalent radical. In particular, Q may be, for example, a carbon or nitrogen atom. More specifically, when Q is nitrogen, $L_5$, $L_6$, and $L_7$ are each not a bond.

It will be understood the selection of substituents $L_1$, $L_2$, $R_1$, $R_2$, Z, etc., including the preferences therefore, defined in connection with Formulas I and II, apply equally to the selection of comparable parameters in accordance with Formula III.

In one embodiment, the zwitterion-containing compound of Formula (III) has the structure:

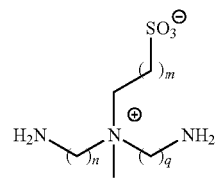

where,
n=1 to 6, preferably 1 to 4, and more preferably, 2 to 4;
m=1 to 6, preferably 1 to 4, and more preferably, 2 to 4; and
q=1 to 6, preferably 1 to 4, and more preferably, 2 to 4.

Specifically, the zwitterion-containing compound may have the structure:

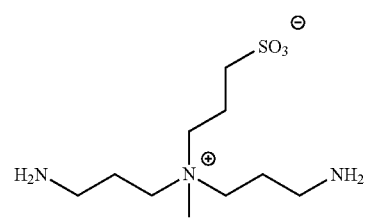

In another embodiment, the zwitterion-containing compound of Formula (III) has the structure:

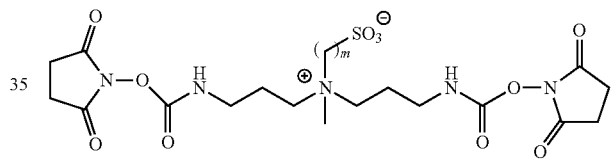

where, m=1 to 6, preferably 1 to 4, and more preferably, 2 to 4.

In another embodiment, a zwitterion-containing compound according to Formula III, has the following structure:

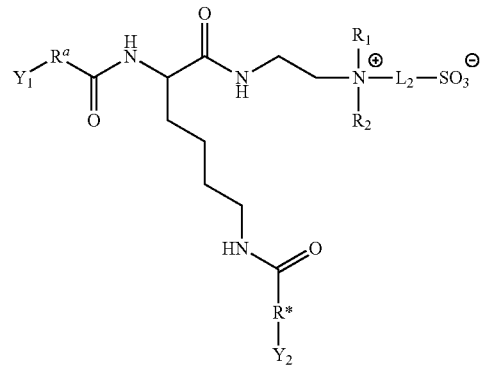

wherein $L_2$ is a divalent radical of the form —(CH$_2$)$_m$— where m=1 to 4.

$R^a$ and R* may be any divalent hydrocarbon moiety, optionally substituted with at least one heteroatom or heteroatom-containing moiety. For example, $R^a$ and/or R* may be selected independently at each occurrence from a $C_1$-$C_{30}$ hydrocarbon radical, such as for example, an alkyl, alkenyl, alkynyl, aryl, or alkyl-aryl group, optionally including from 1-20 heteroatoms or heteroatom-containing moieties, such as nitrogen, oxygen, carboxyl, amine and/or carbonyl groups. In some embodiments, $R^a$ and $R^*$ may be selected independently at each occurrence from hydrogen or a $C_1$-$C_{20}$, $C_1$-$C_{12}$, $C_1$-$C_6$, $C_1$-$C_4$, or $C_1$-$C_3$ hydrocarbon radical, optionally including from 1-20, 1-10, 1-5, or 1-3 heteroatoms or heteroatom-containing moieties. Preferably, $R^a$ and $R^*$ are independently selected at each occurrence from a bond or divalent $C_{1-15}$ alkyl, alkenyl, alkynyl, aryl, or aralkyl groups, each optionally substituted with up to 20 heteroatoms. In other embodiments, $R^a$ and $R^*$ may be selected independently at each occurrence from the group consisting of substituted or unsubstituted branched or straight chain $C_1$-$C_{20}$ alkyl, alkenyl, alkynyl, aryl, or alkyl-aryl groups, each optionally substituted with up to 20 heteroatoms, including without limitation, linear alkyl moieties of the form $-(CH_2)_a-$ where "a" is an integer from 1 to 20, including, for example, $-CH_2-$, $-CH_2CH_2-$, $-CH_2CH_2CH_2-$, or $-CH_2CH_2CH_2CH_2-$; linear alkoxy moieties of the general form $-(CH_2)_aO-$ or $-O(CH_2)_a-$ where "a" is an integer from 1 to 19, including for example, $-CH_2O-$ or $-OCH_2-$, $-CH_2CH_2O-$ or $-OCH_2CH_2-$, $-CH_2CH_2CH_2O-$ or $-OCH_2CH_2CH_2-$; $-O(CH_2)_aO-$ where "a" is as defined above; or a moiety of the form $-(CH_2)_bO(CH_2)_c-$, $-(CH_2)_bS(CH_2)_c-$, or $-(CH_2)_bNR^L(CH_2)_c-$ wherein "b" and "c" are independently an integer from 1 to 18 and $R^L$ is an alkyl, alkenyl, alkynyl, aryl, or alkyl-aryl group, each optionally substituted with up to 20 heteroatoms.

In other embodiments, $R^a$ and $R^*$ are independently selected at each occurrence from divalent radicals from $C_{1-10}$ alkyl, each optionally substituted with up to 20 heteroatoms. In another embodiment, $R^a$ and/or $R^*$ is a divalent $C_{1-15}$ alkyl group, more preferably a divalent $C_{1-10}$ alkyl group, even more preferably a divalent $C_{1-6}$ alkyl group and more preferred still a divalent $C_{1-4}$ alkyl group. In certain embodiments, $R^a$ and/or $R^*$ is a methylene group. In other embodiments, $R^a$ and $R^*$ may be independently selected at each occurrence from a divalent radical of the form $-(CH_2)_q-$ where q=1 to 15. Alternatively, q may be 1 to 10, 1 to 8, 1 to 6 or 1 to 4.

Specifically, the zwitterion-containing compound for cross-linking peptides, proteins, and/or macromolecules may have the structure:

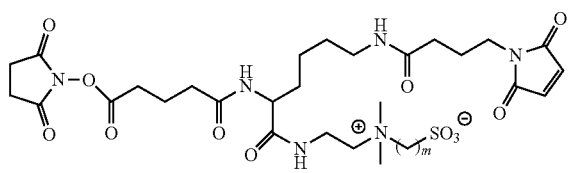

where, m=1 to 6, preferably 1 to 4, and more preferably, 2 to 4.

In one particular embodiment, the zwitterion-containing compound of Formula III may be used in a method for preparing a conjugate of two molecules and/or macromolecules. The method may comprise attaching the zwitterion-containing compound to a first molecule or macromolecule and a second molecule or macromolecule. In particular, the zwitterion-containing compound may form covalently linkages with the first and second molecule(s) or macromolecule(s). Specifically, the $Y_1$ moiety may form covalently linkages with reactive groups, such as, for example, an amine group, a thiol group, or a carbohydrate group, within the first molecule or macromolecule and the $Y_1$ moiety may form covalently linkages with reactive groups, such as, for example, an amine group, a thiol group, or a carbohydrate group, within the second molecule or macromolecule.

Exemplary embodiments of zwitterion-containing compounds for cross-linking peptides, proteins and/or macromolecules are provided by the structures 8c, 8d and 9e in FIG. 1. Other structural variations, combining a strongly hydrophilic zwitterion-containing moiety with two reactive groups for cross-linking, may be devised using various techniques in synthetic organic chemistry.

Figure 3A:
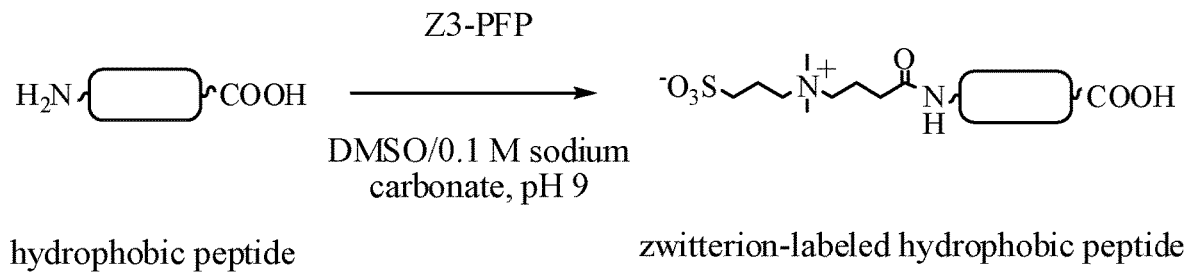
FIG. 3a provides the aqueous solubilities of unmodified hydrophobic molecules and modified hydrophobic molecules, which are conjugated to exemplary zwitterion-containing compounds of the present invention.
Figure 3B:
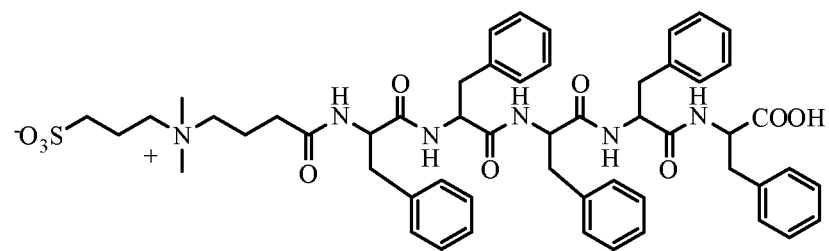
FIG. 3b provides the chemical structures of hydrophobic molecules conjugated to exemplary zwitterion-containing compounds of the present invention.
Figure 3B:
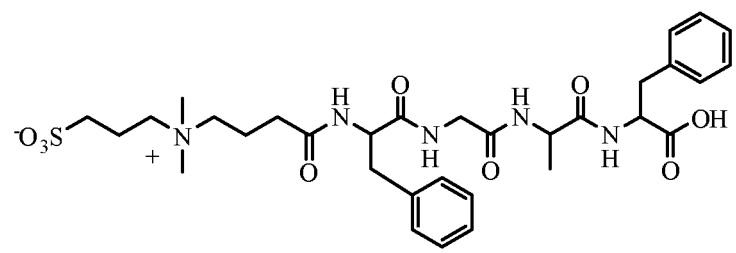
Figure 3B:
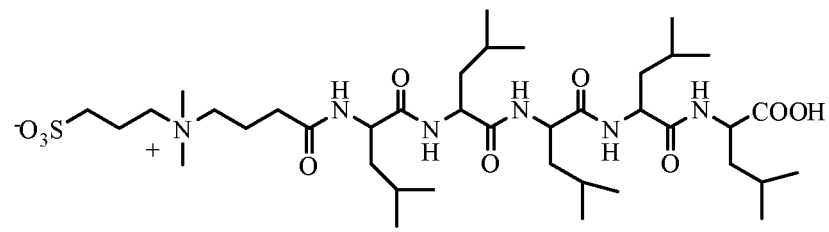
Figure 3B:
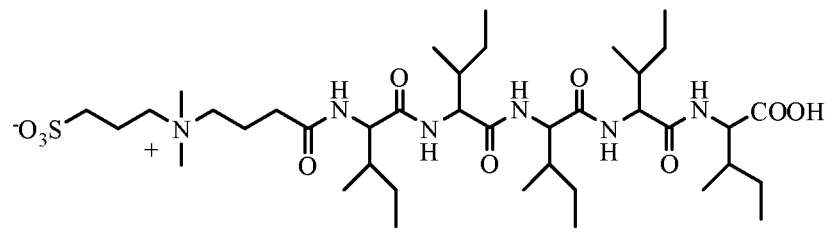

The zwitterion-containing compounds of Formula I may be useful for improving the aqueous solubility of hydrophobic peptides as shown, for example, in FIGS. 3a and 3b. Specifically, four representative hydrophobic peptides, penta (phenylalanine), a tetrapeptide with the sequence Phe-Gly-Gly-Phe, penta(leucine) and penta(isoleucine) were all labeled at the α-amino group with the amine-reactive, zwitterionic reagent Z3-PFP (compound 2c in FIG. 1). One such labeling experiment is illustrated in Example 12. The zwitterion-modified peptides were purified by chromatography and their aqueous solubility was assessed by dissolving them in de-ionized water at concentrations that gave clear homogenous solutions. While the unlabeled peptides exhibited no discernible solubility in water, the zwitterion-modified peptides displayed significantly improved aqueous solubility as shown in FIG. 3a. Penta(phenylalanine) modified by the zwitterion-containing compound Z3-PFP, compound 2c, dissolved in water and provided a clear solution at a concentration of ~0.5 mM. The less hydrophobic tetrapeptide Phe-Gly-Gly-Phe when modified with the zwitterion-containing compound Z3-PFP exhibited aqueous solubility of ~3.0 mM. The very hydrophobic penta(leucine) and penta(isoleucine) peptides, when modified by the zwitterion-containing compound Z3-PFP, also displayed significant aqueous solubility of ~0.1 mM. Accordingly, the zwitterion-containing compounds of the present invention offer the potential to significantly improve the aqueous solubility of hydrophobic polypeptides and other macromolecules.

The zwitterion-containing compounds of the present invention may also be useful for lowering the non-specific binding of hydrophobic and 'sticky' proteins. In one experiment, the chemical competency of certain exemplary amine-reactive zwitterion-containing compounds shown in FIG. 1 were evaluated by treating an acridinium ester (e.g., 2',6'-Dimethyl-4'-(N-succinimidyloxycarbonyl)phenyl 10-Methyl-9-acridinecarboxylate Methylsulfate (NSP-DMAE) or other suitable acridinium esters described by Law et al. in U.S. Pat. No. 5,656,426, which is incorporated herein by reference) labeled bovine serum albumin (BSA) or bovine gamma globulin (BGG) with 10 and 20 equivalents of the zwitterion-containing compound followed by measurement of the zwitterion-containing compound incorporation by mass spectroscopy. The detailed experimental protocol is described in Example 15. As shown in Table 1, all the zwitterion-containing compounds were chemically competent and labeled both BSA and BGG with varying incorporations of the zwitterion-containing compounds. For example, reaction of NSP-DMAE labeled BSA with 10 equivalents of a zwitterion-containing compound, as a zwitterionic label, resulted in the incorporation of 3-5 labels. Reaction of NSP-DMAE labeled BGG with 10 equivalents of a zwitterion-containing compound, as a zwitterionic label, resulted in the incorporation of approximately 4-9 labels. It was observed that an increase in the amount of zwitterion-containing compounds resulted in increased incorporation.

TABLE 1

| Zwitterion-Containing Compounds | Zwitterion-Containing Compound Input (equivalents) | Chemiluminescent-Modified Conjugate | # of Zwitterion-Containing Compounds Incorporated by Conjugate |
|---|---|---|---|
| 1d | Z2-PFP | 10 | BSA-NSP-DMAE | 5 |
| 2c | Z3-PFP | 10 | BSA-NSP-DMAE | 5 |
| 2c | Z3-PFP | 20 | BSA-NSP-DMAE | 8 |
| 3c | Z4-PFP | 10 | BSA-NSP-DMAE | 3.3 |
| 4c | ZPB-PFP | 10 | BSA-NSP-DMAE | 3.4 |
| 4c | ZPB-PFP | 20 | BSA-NSP-DMAE | 7.1 |
| 1d | Z2-PFP | 10 | BGG-NSP-DMAE | 5.3 |
| 2c | Z3-PFP | 10 | BGG-NSP-DMAE | 9 |
| 2c | Z3-PFP | 20 | BGG-NSP-DMAE | 13 |
| 3c | Z4-PFP | 10 | BGG-NSP-DMAE | 3.7 |
| 4c | ZPB-PFP | 10 | BGG-NSP-DMAE | 6 |
| 4c | ZPB-PFP | 20 | BGG-NSP-DMAE | 8.4 |

Zwitterion-containing compounds of the current invention display low non-specific binding when conjugated to proteins. Non-specific binding, as described earlier, in assays using solid phases such as particles or microtiter plates, are undesired binding interactions of conjugates to these solid phases. These undesired binding interactions typically increase the background of the assay leading to a net lowering of the signal to background ratio in the assay and thereby decreasing assay sensitivity. In another experiment, the detailed protocols for which is described in Examples 16 and 17, three 'sticky' proteins, avidin, polyclonal bovine gamma globulin (BGG) and bovine fibrinogen (FBN) were labeled with 10 equivalents of the acridinium ester NSP-DMAE. These three proteins may be used to measure the protein adsorption properties of surfaces with self-assembled monolayers. A portion of each acridinium ester conjugate was further labeled with 25 equivalents of Z3-PFP (compound 2c in FIG. 1) as described in Example 16. The non-specific binding of these conjugates to three different microparticle solid phases was then evaluated and the results are tabulated in Table 2.

Non-specific binding was measured on two different kinds of particles; paramagnetic particles (PMP) and magnetic latex particles (MLP) from a commercial vendor (Dynal™). The two particles differ in their intrinsic composition. PMPs are made mainly of iron oxide particles with a silane coating containing amines. The amines are used to cross-link proteins to the particle surface using reagents such as glutaraldehyde. MLPs on the other hand are made of porous polystyrene with doped-in magnetite to enable magnetic separation.

The PMP used in the current evaluation was coated with an anti-TSH antibody (TSH=Thyroid Stimulating Hormone) on the particle surface using glutaraldehyde coupling chemistry (Solid Phase "PMP" in Table 2). The MLPs used for the current evaluation were Dynal M280-streptavidin particles with bound biotinylated, polyclonal, goat anti-PTH antibody (abbreviated as "M280" in Table 2) and Dynal M270-streptavidin particles with bound biotinylated, monoclonal, mouse anti-cTnI antibody (abbreviated as "M270" in Table 2). These two MLPs had immobilized streptavidin on their surfaces which was then used to further immobilize biotin-labeled antibodies capable of binding the analytes PTH (parathyroid hormone) or cTNI (cardiac troponin I) respectively. The streptavidin-biotin binding interaction is suitable for use in assays. The two types of particles (PMPs and MLPs) were mixed with solutions of the acridinium ester and zwitterion-labeled conjugates for 10 minutes. The particles were then magnetically separated, washed twice with water and then the chemiluminescence associated with the particles was measured. (Experimental details can be found in Example 17.) The ratio of this chemiluminescence value in comparison to the total chemiluminescence input is referred to fractional non-specific binding (fNSB). Lower fNSB means lower non-specific binding. The fNSB values calculated for the various conjugates are tabulated in Table 2. From Table 2, NSP-DMAE labeled avidin on PMP has fNSB=$1.3 \times 10^{-3}$. Further labeling of this conjugate with Z3-PFP lowered the fNSB to $1.7 \times 10^{-4}$. Similarly, whereas the fNSB values of the NSP-DMAE-avidin conjugate on the Dynal-M280 and Dynal-M270 MLP particles were measured to be $1.6 \times 10^{-4}$ and $6.3 \times 10^{-2}$ respectively, the zwitterion labeled conjugate exhibited much lower fNSB values of $8.3 \times 10^{-5}$ and $5.2 \times 10^{-4}$ respectively. As can be seen, zwitterion labeling of NSP-DMAE-avidin conjugate significantly lowers the non-specific binding of this conjugate. The NSP-DMAE-BGG conjugates exhibited similar behavior. This conjugate on PMP, Dynal-M280 and Dynal-M270 MLPs exhibited fNSB values of $1.2 \times 10^{-4}$, $1.3 \times 10^{-4}$ and $1.8 \times 10^{-3}$ respectively whereas further labeling of the conjugate with the zwitterion-containing compound Z3-PFP lowered these fNSB values to $6.8 \times 10^{-5}$, $8.1 \times 10^{-5}$ and $3.9 \times 10^{-4}$ respectively. Similar results were observed for fibrinogen as indicated in Table 1.

TABLE 2

| | Solid Phase | | | | | |
|---|---|---|---|---|---|---|
| | PMP | | M280 | | M270 | |
| Chemiluminescent Conjugates | Unmodified | Z3-PFP Modified | Unmodified | Z3-PFP Modified | Unmodified | Z3-PFP Modified |
| NSP-DMAE-AVD | $1.3 \times 10^{-3}$ | $1.7 \times 10^{-4}$ | $1.6 \times 10^{-4}$ | $8.3 \times 10^{-5}$ | $6.3 \times 10^{-2}$ | $5.2 \times 10^{-4}$ |
| NSP-DMAE-BGG | $1.2 \times 10^{-4}$ | $6.8 \times 10^{-5}$ | $1.3 \times 10^{-4}$ | $8.1 \times 10^{-5}$ | $1.8 \times 10^{-3}$ | $3.9 \times 10^{-4}$ |
| NSP-DMAE-FBN | $9.4 \times 10^{-5}$ | $7.1 \times 10^{-5}$ | $6.2 \times 10^{-5}$ | $6.3 \times 10^{-5}$ | $3.7 \times 10^{-4}$ | $1.2 \times 10^{-4}$ |

PMP = PMP-anti-TSH antibody
M280 = Dynal M280-streptavidin bound biotinylated polyclonal goat anti-PTH antibody
M270 = Dynal M270-streptavidin bound biotinylated monoclonal mouse anti-cTnI antibody In another exemplary embodiment in accordance with the protocols of Examples 16 and 17, the NSP-DMAE-avidin conjugate was labeled with the other amine-reactive zwitterion-containing compounds (Z2-PFP compound 1d, Z4-PFP compound 3c and ZPB-PFP compound 4c) described in FIG. 1 to determine their efficacy to lower the non-specific binding of the avidin conjugates. The results of these measurements are tabulated in Table 3 and they indicate that all the zwitterion labels are effective in lowering the non-specific binding of the avidin conjugates. Using PMP particles as an example, the fNSB value of NSP-DMAE-avidin ($1.3 \times 10^{-3}$) is lowered to $4.1 \times 10^{-4}$ by labeling with 10 equivalents of Z2-PFP; $5.0 \times 10^{-4}$ by labeling with 20 equivalents of Z4-PFP and $5.7 \times 10^{-4}$ by labeling with 10 equivalents of the phosphobetaine label, ZPB-PFP. Similar results were observed on the other particles.

TABLE 3

| Zwitterion-Containing Compounds | | # of Zwitterionic Labels in Input | Solid Phase | | |
|---|---|---|---|---|---|
| | | | PMP | M280 | M270 |
| Control | NSP-DMAE-AVD without zwitterion containing moieties | 0 | $1.1 \times 10^{-3}$ | $1.8 \times 10^{-4}$ | $2.4 \times 10^{-3}$ |
| 1d | Z2-PFP | 10 | $4.1 \times 10^{-4}$ | $8.4 \times 10^{-5}$ | $2.3 \times 10^{-4}$ |
| 2c | Z3-PFP | 10 | $4.8 \times 10^{-4}$ | $8.8 \times 10^{-5}$ | $3.2 \times 10^{-4}$ |
| 2c | Z3-PFP | 20 | $2.6 \times 10^{-4}$ | $6.5 \times 10^{-5}$ | $1.2 \times 10^{-4}$ |
| 3c | Z4-PFP | 20 | $5.0 \times 10^{-4}$ | $8.7 \times 10^{-5}$ | $2.5 \times 10^{-4}$ |
| 4c | ZPB-PFP | 10 | $5.7 \times 10^{-4}$ | $1.0 \times 10^{-4}$ | $4.6 \times 10^{-4}$ |
| 4c | ZPB-PFP | 20 | $3.4 \times 10^{-4}$ | $7.7 \times 10^{-5}$ | $1.6 \times 10^{-4}$ |

PMP = PMP-anti-TSH antibody
M280 = Dynal M280-streptavidin bound biotinylated polyclonal goat anti-PTH antibody
M270 = Dynal M270-streptavidin bound biotinylated monoclonal mouse anti-cTnI antibody In addition to the amine-reactive zwitterion-containing compounds, FIG. 1 also provides structures of thiol-reactive zwitterion labels (compounds 6b and 7a) as well as the structures of zwitterion-containing compounds with nucleophilic amine functional groups (compounds 5c and 8c). These zwittion-containing compounds permit the utilization of different chemistry to introduce these zwitterionic structures for improving the aqueous solubility and lowering the non-specific binding of various molecules. The thiol-reactive compounds, for example, can be used to cap free thiol moieties in peptides, proteins etc to prevent thiol-oxidation mediated aggregation. Compound 5c, with an amino moiety can be used to modify carboxyl groups on peptides, proteins etc to improve their solubility. Compound 8c has two amino groups and can be used a linker to conjugate any two molecules. For example, 8c can be used to make tracers where a fluorescent or chemiluminescent label can be conjugated to a hapten. Two examples of such conjugates are illustrated in FIG. 2b which shows the structures of fluorescein conjugates of progesterone, a steroid and FK506, an immunosuppressive drug. The zwitterionic compound 8c, containing two amines was used to conjugate the fluorescent molecule fluorescein to the two haptens as described in detail in Example 11.

Compound 8d, Di-Z-NHS, in FIG. 1 is illustrative of a zwitterionic, homo-bifunctional, cross-linking reagent with two, amine-reactive, N-hydroxysuccinimide ester functional groups that can be used to conjugate two peptides, proteins or other macromolecules. The synthesis of this compound is described in Example 8. Example 13 illustrates the conjugation of two hydrophobic peptides, penta(phenylalanine) and the tetrapeptide Phe-Gly-Phe-Gly using compound 8d. In this sequence of reactions described in Example 13, the α-amino group in penta(phenylalanine) was first reacted with an excess of compound 8d followed by a purification step and subsequent reaction of the zwitterionic, penta(phenylalanine) conjugate 13a with the α-amino group of the tetrapeptide. The final nonapeptide 13b comprising the two hydrophobic peptides linked by the sulfobetaine containing reagent 8d was formed cleanly.

Compound 9e, Z-maleimide-NHS, in FIG. 1 is a particularly preferred embodiment of a zwitterionic, heterobifunctional, cross-linking reagent with an amine-reactive, N-hydroxysuccinimide ester as well as a thiol-reactive, maleimide group that can be used for conjugation. The synthesis of this compound is described in Example 9. Example 14 illustrates the conjugation of two peptides, penta(phenylalanine) and the dipeptide Cys-Gly using 9e. In the first step of the reaction, described in Example 14, the α-amino group of penta(phenylalanine) was reacted with the N-hydroxysuccinimide ester of 9e to give the sulfobetaine-modified pentapeptide also containing the maleimide group. In the second step, the sulfhydryl moiety of the dipeptide Cys-Gly was reacted with the maleimide group to give the heptapeptide conjugate 14b.

In summary, the present invention provides various zwitterion-containing compounds that are useful for the modification of hydrophobic molecules to improve their aqueous solubility as well as to lower their non-specific binding to solid phases. The present invention also describes zwitterion-containing linkers for improving the aqueous solubility of detectable labels such as fluorescein and biotin as well as zwitterionic cross-linkers useful for preparing conjugates of peptides, proteins and other macromolecules.

Example 1

Synthesis of Z2-PFP, Compound 1d
a) Compound 1a
A mixture of 4-dimethylaminobutyric acid hydrochloride (2 g, 0.012 mole, Aldrich), p-toluenesulfonic acid (1.53 g, 1.05 equivalents) and benzyl alcohol (2.2 g, 0.0204 mole) in anhydrous toluene (50 mL) was refluxed under a nitrogen atmosphere with azeotropic removal of water. After 2 hours, the reaction was cooled to room temperature and diluted with water (75 mL) and ethyl acetate (50 mL). The aqueous solution containing product was extracted three times with ethyl acetate (3×50 mL). The pH of the aqueous solution was then adjusted to pH 9 with 5% KOH and the resulting suspension was extracted with ethyl acetate (2×50 mL). The combined ethyl acetate extracts was dried over anhydrous magnesium sulfate, filtered and concentrated under reduced pressure to give a viscous oil. Yield=0.9 g (34%).

b) Compound 1b
A mixture of compound 1a, (0.1 g, 0.45 mmole), sodium 2-bromoethanesulfonate (0.19 g, 2 equivalents) and 2,6-di-tert-butylpyridine (99 µL, 0.45 mmole) in [BMIM]BF$_4$](1 mL, Aldrich) was heated in an oil bath at 150° C. with vigorous stirring for 16 hours. The reaction was then cooled to room temperature and a small portion of the reaction mixture was withdrawn, diluted with methanol/water and analyzed by analytical HPLC using a Phenomenex, C$_{18}$, 4.6×250 mm column and a 30 minute gradient of 10→70% MeCN/water (with 0.05% TFA) at a flow rate of 1.0 mL/minute and UV detection at 260 nm and 220 nm. Product was observed eluting at Rt=13.3 minutes (~40% conversion). The reaction mixture was prepared by diluting it with water (15 mL) and washing this solution with ethyl acetate (2×25 mL). The aqueous solution was then treated with 3 to 4 drops of ammonia and further extracted with ethyl acetate (2×25 mL). The aqueous solution was then concentrated to about 7 mL by rotary evaporation. The product was then purified by preparative HPLC using an YMC, C$_{18}$, 30×250 mm column and the same gradient as described above at a flow rate of 20 mL/minute. HPLC fractions containing product were combined and concentrated under reduced pressure. Yield=30 mg (20%, white solid); MALDI-TOF MS 330.6 observed.

c) Compound 1c

A solution of compound 1b in 10% aqueous methanol (20 mL) was hydrogenated over 30 mg of 5% palladium on carbon at room temperature for 48 hours. The suspension was then filtered and the catalyst was rinsed with 1:1 aqueous methanol (5 mL). The combined filtrate was concentrated under reduced pressure. Yield=26 mg (quantitative); MALDI-TOF MS 240.5 observed.

d) Compound 1d

A solution of compound 1c (25 mg, 0.104 mmol) and pentafluorophenol (45 mg, 0.25 mmol) in 1:1 0.1 N HCl/MeCN (4 mL) was treated with EDC.HCl (50 mg, 2.5 equivalents). The reaction was stirred at room temperature. After 1.5 hours, HPLC analysis, as described in section (b) indicated product eluting at Rt=17 minutes. The product was purified by preparative HPLC using an YMC, $C_{18}$, 30×250 mm column and a 30 minute gradient of 10→100% MeOH/water (with 0.05% TFA) above at a flow rate of 20 mL/minute. The product fractions eluting at 27 minutes were collected, diluted with an equal volume of water, frozen at −80° C. and lyophilized to dryness. Yield=13.2 mg (31%); MALDI-TOF MS 406.6 observed.

The following reactions describe the synthesis of Z2-PFP, compound 1d.

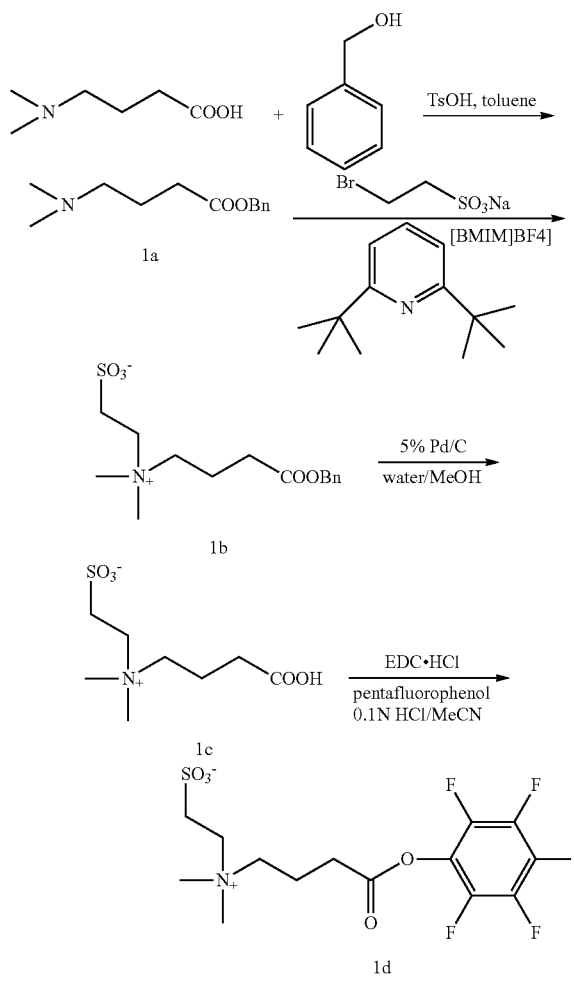

Example 2

Synthesis of Z3-PFP, Compound 2c a) Compound 2a

A solution of compound 1a (0.2 g, 0.905 mmol) in anhydrous dimethylformamide (DMF) (5 mL) was treated with 1,3-propane sultone (0.165 g, 1.5 equivalents) and 2,6-di-tert-butylpyridine (0.24 mL, 1.2 equivalents). The reaction was heated at 150° C. under a nitrogen atmosphere. After 1 hour, HPLC analysis was performed using a Phenomenex, $C_{18}$, 4.6×250 mm column and a 40 minute gradient of 10-40% MeCN/water (with 0.05% TFA) at a flow rate of 1.0 mL/minute and UV detection at 260 nm and 220 nm. Product was observed eluting at Rt=14 minutes with starting material at Rt=13 minutes. The reaction was cooled to room temperature and the solvent was removed under reduced pressure. The residue was partitioned between ethyl acetate (50 mL) and water (50 mL). The aqueous solution was separated and washed with ethyl acetate (2×50 mL). The aqueous solution was treated with 5 drops of ammonia and further extracted with ethyl acetate (2×25 mL). The aqueous solution was then concentrated under reduced pressure to afford a sticky gum. Yield=0.35 g; MALDI-TOF MS 344.3 observed.

b) Compound 2b

A solution of compound 2a (0.42 g, 1.22 mmoles) in methanol (40 mL) was treated with 0.25 g of 10% palladium on carbon. The suspension was hydrogenated in a Parr shaker at 40 psi for 2 hours at room temperature. The reaction was then filtered and the methanol solution was concentrated under reduced pressure to afford a white solid. Yield=0.234 g (quantitative); MALDI-TOF MS 254.3 observed.

c) Compound 2c

A solution of compound 2b (0.114 g, 0.45 mmol) in a 1:1 mixture of 0.1 N HCl/MeCN (6 mL) was treated with pentafluorophenol (0.125 g, 1.5 equivalents) and EDC/HCl (0.230 g, 2.5 equivalents). The reaction was stirred at room temperature. After 1 hour, HPLC analysis was performed using a Phenomenex, $C_{18}$, 4.6×250 mm column and a 40 minute gradient of 10→60% MeCN/water (with 0.05% TFA) at a flow rate of 1.0 mL/minute and UV detection at 260 nm and 220 nm. Product was observed eluting at Rt=18 minutes. The crude reaction mixture was purified by HPLC using an YMC, $C_{18}$, 30×250 mm column and a 40 minute gradient of 10→60% MeCN/water (with 0.05% TFA) above at a flow rate of 20 mL/minute. The HPLC fractions containing product were frozen at −80° C. and lyophilized to dryness. Yield=78 mg (41%); MALDI-TOF MS 420 observed.

The following reactions describe the synthesis of Z3-PFP, compound 2c.

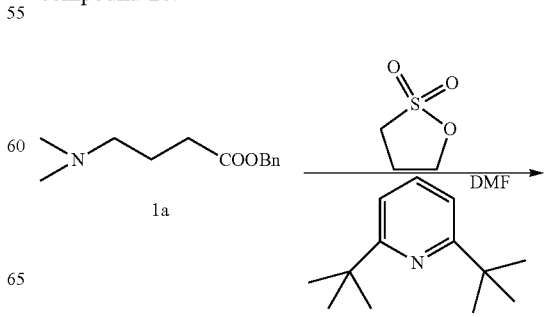

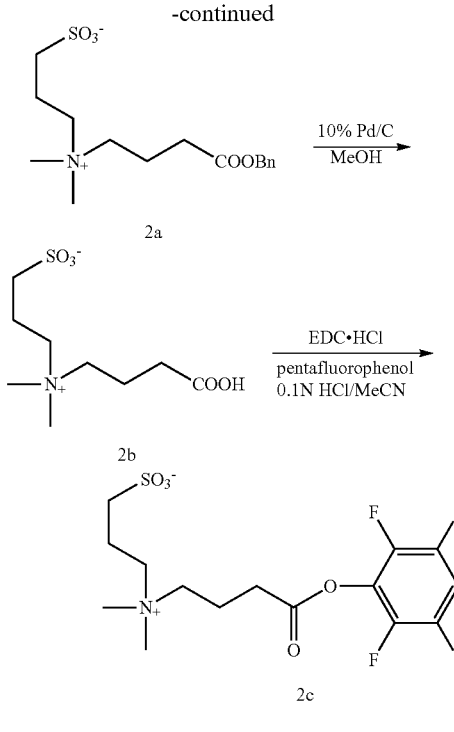

After 1 hour HPLC analysis was performed using a Phenomenex, $C_{18}$, 4.6×250 mm column and a 30 minute gradient of 10→70% MeCN/water (with 0.05% TFA) at a flow rate of 1.0 mL/minute and UV detection at 260 nm. Product was observed eluting at Rt=19 minutes. The crude reaction mixture was purified by HPLC using an YMC, $C_{18}$, 30×250 mm column and a 30 minute gradient of 10→100% MeOH/water (with 0.05% TFA) above at a flow rate of 20 mL/minute. The HPLC fractions containing product were diluted with 2 volumes of water, frozen at −80° C. and lyophilized to dryness. Yield=120 mg (46%); MALDI-TOF MS 434.5 observed.

The following reactions describe the synthesis of Z4-PFP, compound 3c.

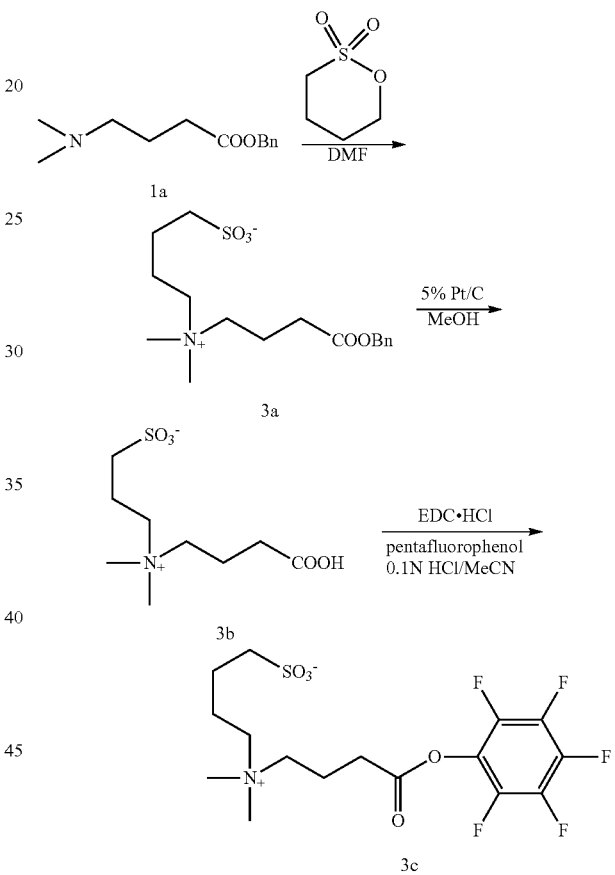

Example 3

Synthesis of Z4-PFP, Compound 3c a) Compound 3a

A mixture of compound 1a (0.15 g, 0.68 mmol) and 1,4-butane sultone (0.185 g, 2 equivalents) in anhydrous DMF (5 mL) was heated at 140–145° C. under a nitrogen atmosphere for 16 hours. The reaction was then cooled to room temperature and the solvent was removed under reduced pressure. The residue was partitioned between water (30 mL) and ethyl acetate (30 mL). The aqueous layer was washed once with ethyl acetate (30 mL). The aqueous solution was then treated with two drops of ammonia and further extracted with ethyl acetate (30 mL). HPLC analysis was performed using a Phenomenex, $C_{18}$, 10×250 mm "PRODIGY" column and a 40 minute gradient of 10→40% MeCN/water (with 0.05% TFA) at a flow rate of 4.0 mL/minute and UV detection at 260 nm. Product was observed eluting as a very sharp peak at Rt=20 minutes with only a trace of starting material at Rt=25 minutes. The aqueous solution was concentrated under reduced pressure to afford a brown, sticky solid. Yield=0.3 g; MALDI-TOF MS 358.2 observed.

b) Compound 3b

Crude compound 3a (0.3 g, 0.84 mmol) was dissolved in methanol (25 mL) and treated with 5% platinum on carbon (0.3 g). The reaction was hydrogenated at room temperature for 3 days at room temperature using a balloon. The reaction was then filtered and the catalyst was rinsed with methanol (10 mL). The methanol solution was concentrated under reduced pressure to afford a sticky solid. Yield=0.245 g (quantitative); MALDI-TOF MS 268.3 observed.

c) Compound 3c

A solution of compound 3b (0.16 g, 0.6 mmol) and pentafluorophenol (0.165 g, 1.5 equivalents) in 1:1, 0.1 N HCl/MeCN (6 mL) was treated with EDC·HCl (0.286 g, 2.5 equivalents). The reaction was stirred at room temperature.

Example 4

Synthesis of ZPB-PFP, Compound 4c a) Compound 4a

A mixture of compound 1a (0.1 g, 0.45 mmol) and n-propylcyclophosphate ester (0.112 g, 1.5 equivalents, synthesized from 1,3,2-dioxaphopholane-2-oxide and n-propanol as described by Peresypkin and Menger in *Org. Lett.* 1999, 9, 1347-1350) in [BMIM][BF$_4$] (1 mL) was heated at 150° C. for 3 hours. The reaction was then cooled to room temperature and a portion (5 µL) was withdrawn, diluted with methanol (0.1 mL) and analyzed by HPLC using a Phenomenex, $C_{18}$, 4.6×250 mm column and a 30 minute gradient of 10→70% MeCN/water (with 0.05% TFA) at a flow rate of 1.0 mL/minute and UV detection at 260 nm.

Product (>50% conversion) was observed eluting at Rt=21 minutes. The reaction mixture was then processed as described in section (b), Example 1. The crude reaction mixture was purified by HPLC using an YMC, $C_{18}$, 30×250 mm column and a 30 minute gradient of 10→100% MeOH/water (with 0.05% TFA) above at a flow rate of 20 mL/minute. The HPLC fractions containing product were concentrated under reduced pressure. Yield=100 mg (57%); MALDI-TOF MS 388.9 observed.

b) Compound 4b

A solution of compound 4a (0.1 g, 0.26 mmol) in methanol (20 mL) was treated with 0.1 g of 5% platinum on carbon and hydrogenated at room temperature using a balloon. After 16 hours, the reaction was filtered and the filtrate was concentrated under reduced pressure. Yield=78 mg (quantitative); MALDI-TOF MS 298.3 observed.

c) Compound 4c

A solution of compound 4b (40 mg, 0.134 mmol) and pentafluorophenol (37 mg, 1.5 equivalents) in 1:1, 0.1 N HCl/MeCN (4 mL) was treated with EDC.HCl (64 mg, 2.5 equivalents). The reaction was stirred at room temperature. After one hour, HPLC analysis was performed using a Phenomenex, $C_{18}$, 4.6×250 mm column and a 30 minute gradient of 10→70% MeCN/water (with 0.05% TFA) at a flow rate of 1.0 mL/minute and UV detection at 260 nm. Product was observed eluting at Rt=26 minutes. The crude reaction mixture was purified by HPLC using an YMC, $C_{18}$, 30×250 mm column and a 30 minute gradient of 10→70% MeCN/water (with 0.05% TFA) above at a flow rate of 20 mL/minute. The HPLC fractions containing product were frozen at −80° C. and lyophilized to dryness. Yield=5.5 mg (9%); MALDI-TOF MS 464.4 observed.

The following reactions describe the synthesis of ZPB-PFP, compound 4c.

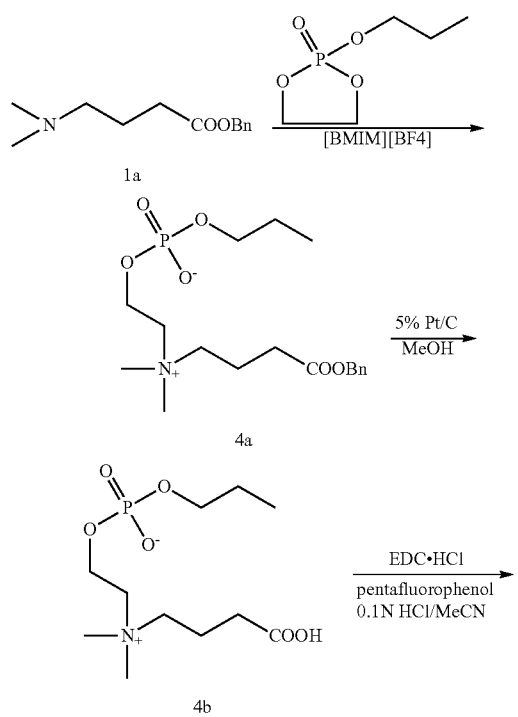

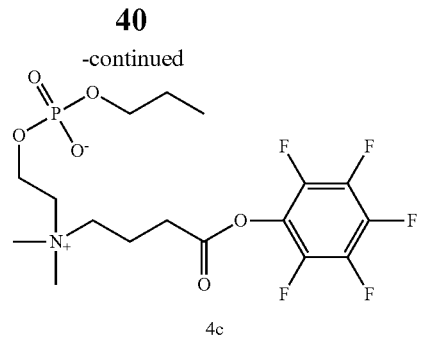

Example 5

Synthesis of Z—$NH_2$, Compound 5c a) Compound 5a

A solution of N,N-dimethylethylenediamine (2.00 g, 21.55 mmoles) dissolved in chloroform (15 ml) was added drop-wise to a stirred solution of N-(benzyloxycarbonyloxy)succinimide (6.30 g, 24.79 mmoles, Aldrich) in chloroform (25 ml) under a nitrogen atmosphere and at 0° C. The reaction mixture was stirred at 0° C. for 1 hour and at room temperature for 1 hour. The resulting reaction mixture was diluted with chloroform (40 ml) and washed with saturated aqueous sodium bicarbonate (3×20 ml). The organic layer was separated and dried over anhydrous sodium sulfate. The filtrate was concentrated to give 5.16 g of a slightly pink oil as the desired product. MALDI-TOF MS 223.5 observed.

b) Compound 5b

Compound 5a (1.00 g, 4.5 mmol) was dissolved in anhydrous ethyl acetate (5 ml) in a sealed tube and 1,3-propanesultone (1.10 g, 9.0 mmol) was added under a nitrogen atmosphere. The sealed tube was heated to 90° C. for 16 hours and then cooled to room temperature. The white precipitates were filtered and washed with anhydrous ethyl acetate (20 ml×3). The resulting white solid was dried under high vacuum to give 1.31 g (85%) of desired product. MALDI-TOF MS 344.9 observed.

c) Compound 5c

Compound 5b (580 mg, 1.7 mmol) was dissolved in methanol/water (95/5, 40 ml) and 10% palladium on activated charcoal (58 mg) was added. The reaction was hydrogenated using a balloon) for 4 hours at room temperature. The reaction mixture was then filtered and the filtrate was concentrated to dryness to give a white solid as the desired product. MALDI-TOF MS 211 observed.

The following reactions describe the synthesis of Z—$NH_2$, compound 5c.

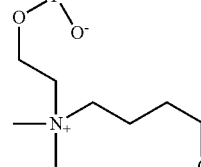

-continued

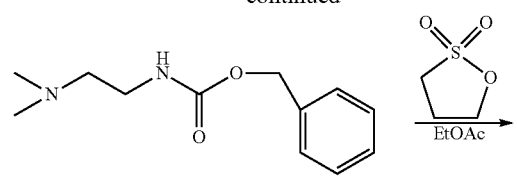

5a

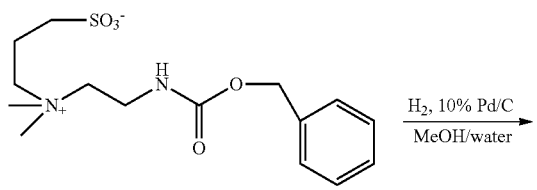

5b

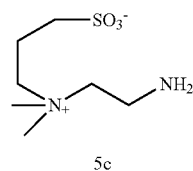

5c

Example 6

Synthesis of Z-Maleimide-1, Compound 6b

A solution of methoxycarbonylmaleimide (0.183 g, 0.0012 mole, Keller and Rudinger *Hel. Chim. Acta.* 1975, 58, 531-541) in anhydrous THF (5 mL) was treated with N,N-dimethylethylenediamine (64 uL, 0.5 equivalents). The reaction was stirred at room temperature and after 1 hour, TLC on silica using MeOH as eluent showed the formation of a polar product 6a (Rf~0.2, streaking). MALDI-TOF mass spectral analysis of the crude reaction mixture showed a strong product ion at 169.5. The reaction mixture was filtered through glass wool and the filtrate was treated with distilled propane sultone (0.288 g, 2 equivalents). The reaction was refluxed under a nitrogen atmosphere for 4 to 5 hours. It was observed that a white precipitate had formed in the reaction. The reaction was diluted with ethyl acetate (10-15 mL) and was cooled in the refrigerator for 36 hours to complete the precipitation. The product was then collected by filtration and rinsed with ethyl acetate (5 mL). The sticky solid was then dissolved in water (10 mL, containing 0.05% TFA). MALDI-TOF mass spectral analysis showed a strong ion at 291.5 indicating product and no starting material. The aqueous solution was frozen at −80° C. and lyophilized to give a white fluffy powder. Yield=53 mg (20%).

The following reactions describe the synthesis of Z-maleimide-1, compound 6b.

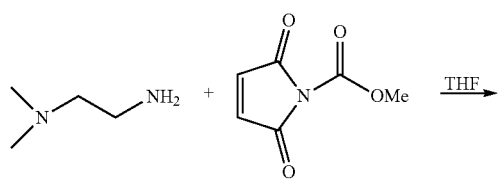

-continued

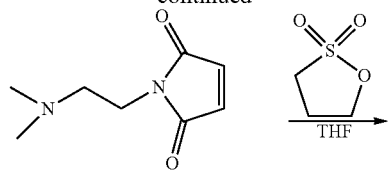

6a

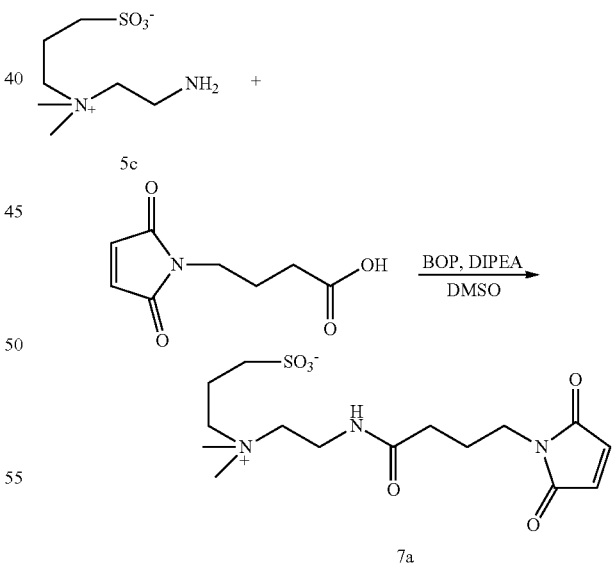

Example 7

Synthesis of Z-Maleimide-2, Compound 7a

To a solution of compound 5c (21.0 mg, 0.1 mmol) and 4-maleimidobutyric acid (18.3 mg, 0.1 mmol) in anhydrous dimethyl sulfoxide (1 ml) was added diisopropylethylamine (35 ul, 0.2 mmol) and BOP reagent (66.2 mg, 0.15 mmol). The reaction was stirred at room temperature for 1 hour. The crude reaction mixture was purified by HPLC using an YMC, $C_{18}$, 30×250 mm column and a 40 minute gradient of 0→40% MeCN/water (with 0.05% TFA) above at a flow rate of 20 mL/minute. The HPLC fractions containing product were frozen at −80° C. and lyophilized to dryness. Yield=43 mg (quantitative); MALDI-TOF MS 376.7 observed.

The following reaction describes the synthesis of Z-maleimide-2, compound 7a.

Example 8

Synthesis of Z-Diamine, Compound 8c and Z-Di-NHS, Compound 8d a) Compound 8a

A solution of N,N-bis(3-aminopropyl)methyl amine (1 g, 6.9 mmoles, TCI) in chloroform (40 mL) was treated with benzyloxycarbonylsuccinimide (3.78 g, 2.2 equivalents). The reaction was stirred at room temperature for 16 hours. TLC analysis on silica of the reaction mixture using 15% methanol in ethyl acetate showed the formation of a polar product in a clean reaction. The reaction mixture was diluted with chloroform (40 mL) and washed with saturated aqueous sodium bicarbonate solution. It was then dried over anhydrous magnesium sulfate, filtered and concentrated under reduced pressure to afford a viscous oil that solidified upon storage to a waxy solid. Yield=3.2 g; MALDI-TOF MS 414.4 observed.

b) Compound 8b

A solution of compound 8a (1.2 g, 2.9 mmoles) in anhydrous DMF (15 mL) was treated with 1,3-propane sultone (0.71 g, 2 equivalents). The reaction was heated at 145° C. under nitrogen for 1 hour. HPLC analysis of a small portion of the reaction mixture was performed using a Phenomenex, $C_{18}$ 4.6 mm×25 cm column and a 30 minute gradient of 10→70% B (A=water with 0.05% TFA, B=MeCN with 0.05% TFA) at a flow rate of 1.0 mL/minute and UV detection at 260 nm. Product was observed eluting at Rt=19.6 minutes (~80% conversion) with starting material eluting at Rt=21.6 minutes. The reaction mixture was concentrated under reduced pressure and the recovered oil was dissolved in methanol (20 mL). TLC analysis on silica using 40% methanol, 60% ethyl acetate indicated clean separation of product (Rf ~0.2) from starting material (Rf ~0.3). The above reaction was repeated on the same scale and the combined reaction mixture was purified by flash chromatography on silica using 40% methanol, 60% ethyl acetate as eluent. Yield=1.55 g (60%); white foam; MALDI-TOF MS 536.4 observed.

c) Compound 8c

Compound 8b (0.8 g, 1.49 mmoles) was stirred in 15 mL of 33% HBr/AcOH at room temperature for 24 hours. Ether (100 mL) was then added and a white, granular solid separated out. The product was allowed to settle and the ether was decanted. This process was repeated twice with ether (2×50 mL). Finally, the product was dried under vacuum. The recovered viscous oil was dissolved in 5 to 6 mL water, frozen at −80° C. and lyophilized to dryness to afford a glassy solid. Yield=0.766 g (quantitative); MALDI-TOF MS 268.2 observed. TLC analysis on silica using 25% ammonia, 75% methanol and ninhydrin for visualization showed a single spot of Rf ~0.2.

d) Compound 8d

A solution of compound 8c (25 mg, 56 μmoles) in DMSO (1 mL) was treated with diisopropylethylamine (39 μL, 4 equivalents) and this solution was added drop-wise to a solution of disuccinimidyl carbonate (96 mg, 0.37 mmol) in DMSO (2 mL). The reaction was stirred at room temperature. After 30 minutes, a portion of the reaction mixture was analyzed by HPLC using a Phenomenex, $C_{18}$ 4.6 mm×25 cm column and a 30 minute gradient of 0→40% B (A=water with 0.05% TFA, B=MeCN with 0.05% TFA) at a flow rate of 1.0 mL/minute and UV detection at 220 nm. Product was observed eluting at Rt=10 minutes. The crude reaction mixture was purified by HPLC using an YMC, $C_{18}$, 30×250 mm column and a 40 minute gradient of 0→40% MeCN/water (with 0.05% TFA) above at a flow rate of 20 mL/minute. The HPLC fractions containing product were frozen at −80° C. and lyophilized to dryness. Yield=15 mg (50%); MALDI-TOF MS 549.8 observed.

The following reactions describe the synthesis of Z-Di-NHS, compound 8d.

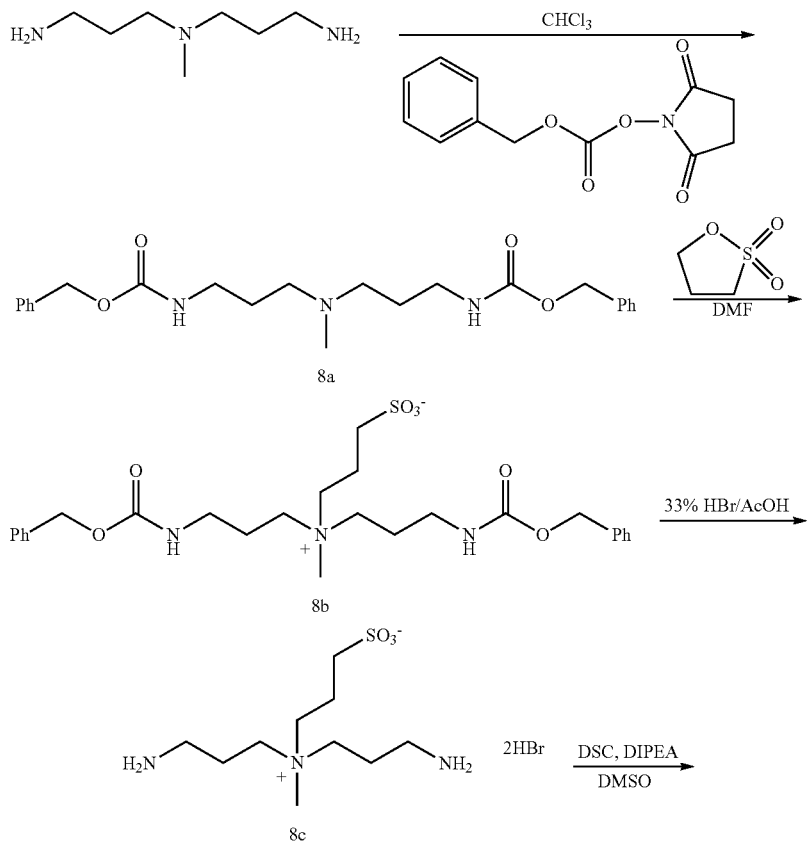

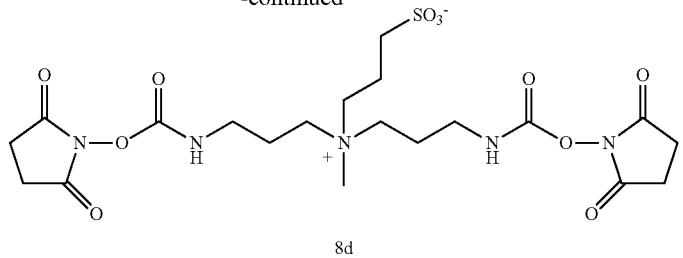

8d

Example 9

Synthesis of Z-maleimide-NHS, Compound 9e a) Compound 9a

A solution of compound 5c (105 mg, 0.5 mmole) in anhydrous DMSO (2 mL) was treated with triethylamine (70 uL, 0.5 mmol) and N-α-t-BOC—N-ε-CBZ-lysine-N-hydroxsuccinimide ester (239 mg, 0.5 mmol, Aldrich). The suspension was stirred at room temperature for 24 hours and then analyzed by HPLC using a YMC, $C_{18}$, 50×4.0 mm, 3 micron column and a 10 minute gradient of 10→90% MeCN/water (with 0.05% TFA) at a flow rate of 1.0 mL/minute and UV detection at 260 nm. Product was observed to elute at Rt=6.2 minutes. The product was purified by preparative HPLC using an YMC, $C_{18}$, 30×250 mm column and a 30 minute gradient of 10→70% MeCN/water (with 0.05% TFA) at a flow rate of 20 mL/minute. The product fraction was collected and frozen at −80° C. and lyophilized. The product was obtained as a white powder. Yield=225 mg (79%); MALDI-TOF MS 572.6 observed.

b) Compound 9b

Compound 9a (200 mg, 0.35 mmol) was added to a mixture of MeOH and $H_2O$ (20 ml, 95/5). Then, 10% Pd/C (20 mg) was added. The resulting suspension was hydrogenated at room temperature using a balloon for 4 hours. The reaction mixture was then filtered. The filtrate was concentrated under reduced pressure at room temperature. The desired product was obtained as a clear oil. Yield=176 mg, (quantitative); MALDI-TOF MS 440.3 observed.

c) Compound 9c

A solution of compound 9b (176 mg, 0.4 mmol) in anhydrous DMSO (4 mL) was treated with 4-maleimidobutyric acid N-hydroxsuccinimide ester (50 mg, 0.178 mmol, Thermo) and triethylamine (54 uL, 0.4 mmol). The reaction was stirred at room temperature. After 1 to 2 hours, HPLC analysis was performed using a Phenomenex, $C_{18}$, 4.6×250 mm column and a 40 minute gradient of 0→40% MeCN/water (with 0.05% TFA) at a flow rate of 1.0 mL/minute and UV detection at 260 nm and 220 nm. Product was observed eluting at Rt=27.5 minutes. The crude reaction mixture was purified by HPLC using an YMC, $C_{18}$, 30×250 mm column and a 40 minute gradient of 0→40% MeCN/water (with 0.05% TFA) at a flow rate of 20 mL/minute. The HPLC fractions containing product were frozen at −80° C. and lyophilized to dryness. Yield=45 mg (40%); MALDI-TOF MS 604.9 observed.

d) Compound 9d

A solution of compound 9c (25 mg, 41 umoles) in trifluoroacetic acid (2 mL) was stirred in an ice-bath for 3 hours. Anhydrous ether (75 mL) was then added to the reaction mixture to precipitate the product which was collected by filtration and rinsed with ether. The product was then dissolved in methanol (15-20 mL) and analyzed by HPLC as described in Example 9, section (c). Product was observed eluting at Rt=13.7 minutes (complete conversion). The methanol solution was diluted with anhydrous toluene (10 mL) and then concentrated under reduced pressure to afford a white sticky solid. Yield=45 mg (quantitative); MALDI-TOF MS 504.4 observed.

e) Compound 9e

A solution of crude compound 9d (24 mg, 38.6 μmoles) and disuccinimidyl glutarate (50 mg, 4 equivalents, Thermo) in anhydrous DMSO (2 mL) was treated with triethylamine (6 μL, 1.1 equivalents). The reaction was stirred at room temperature. After 15 minutes, HPLC analysis was performed as described in Example 9, section (c). Product was observed eluting at Rt=24 minutes. The product was purified by preparative HPLC as described in Example 9, section (c). The HPLC fractions containing product were frozen at −80° C. and lyophilized to dryness. Yield=8 mg (30%); MALDI-TOF MS 717.1 observed.

The following reactions describe the synthesis of compound 9e.

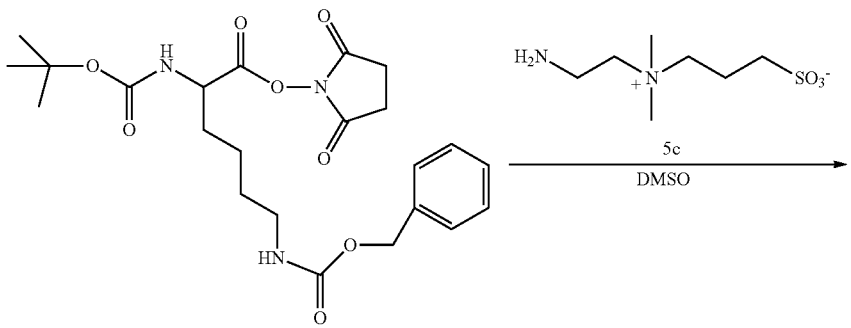

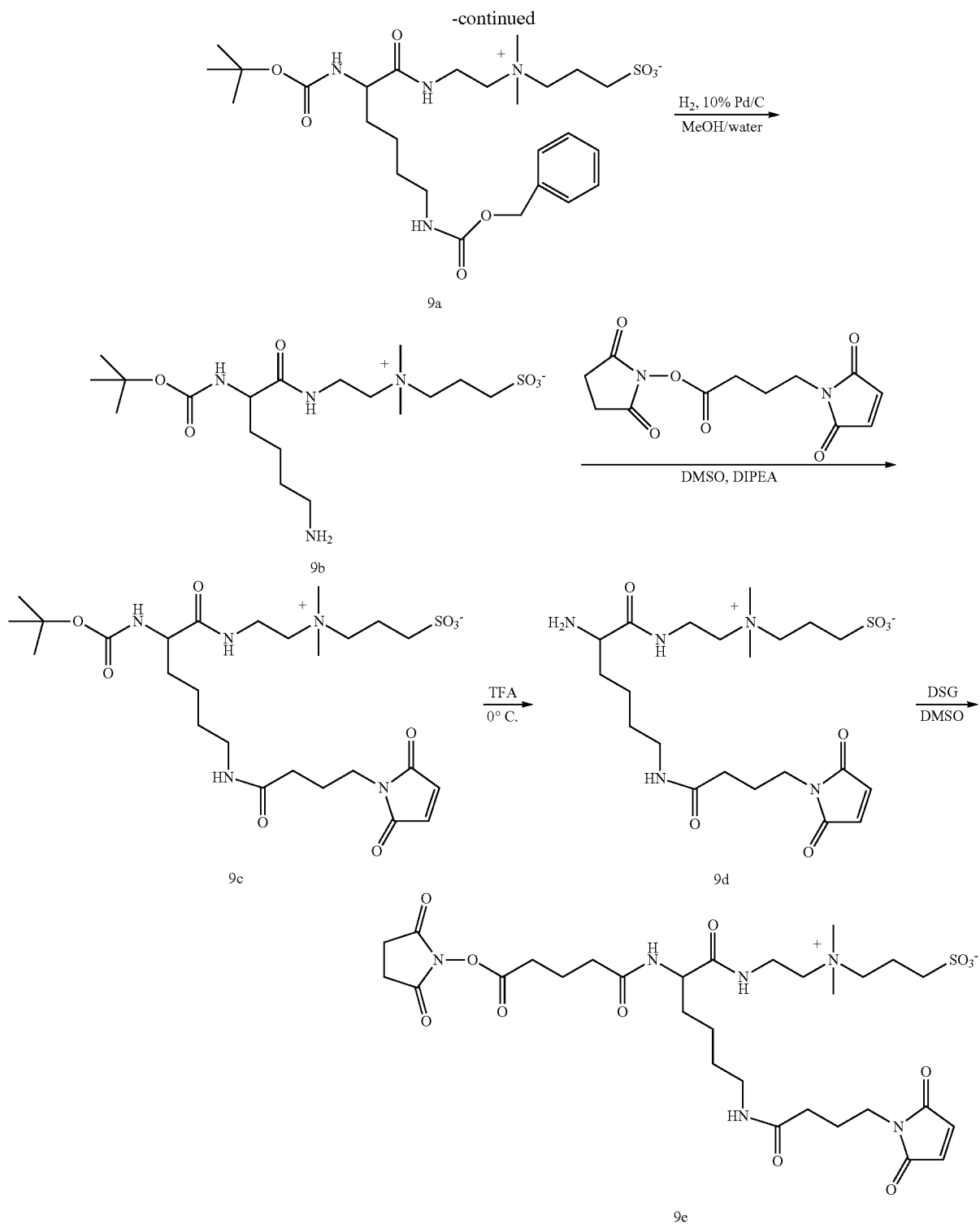

Example 10

Synthesis of Biotin-Z—NH$_2$, Compound 10a and Biotin-Z—NHS, Compound 10b a) Compound 10a A solution of biotin-p-nitrophenyl ester (11 mg, 30 moles) in anhydrous DMF (1.5 mL) was added drop-wise to a stirred solution of compound 8c (40 mg, 89.4 moles, HBr salt) dissolved in a mixture of water (0.8 mL) and 0.1 M sodium carbonate pH 9 (1.0 mL). The reaction was stirred at room temperature. After 30 minutes, HPLC analysis of a small portion of the reaction mixture was performed using a Phenomenex, C$_{18}$ 4.6 mm×25 cm column and a 40 minute gradient of 0→40% B (A=water with 0.05% TFA, B=MeCN with 0.05% TFA) at a flow rate of 1.0 mL/minute and UV detection at 220 nm. Product was observed eluting at Rt=13 minutes. The product was purified by preparative HPLC as described in Example 4, section (c) using the above gradient. The HPLC fractions containing product were concentrated under reduced pressure. Yield=18.2 mg (quantitative); MALDI-TOF MS 494 observed.

b) Compound 10b

A solution of compound 10a (18.2 mg, 37 umoles) in methanol (2 mL) was treated with diisopropylethylamine (32.2 uL, 5 equivalents) and glutaric anhydride (21 mg, 5 equivalents). The reaction was stirred at room temperature. After 30 minutes, HPLC analysis as described in section (d) showed product eluting at Rt=17.5 minutes. The product was purified by preparative HPLC as described in example 4, section (c) using a 40 minute gradient of 0→40% MeCN/water (with 0.05% TFA). The HPLC fractions containing product were concentrated under reduced pressure. Yield=19.7 mg (88%); MALDI-TOF MS 608.5 observed.

c) Compound 10c

A solution of compound 10b (19.7 mg, 32.4 umoles) in anhydrous DMF (1 mL) was treated with diisopropylethylamine (11.3 μL, 2 equivalents) and TSTU (15 mg, 1.5 equivalents). The reaction was stirred at room temperature. After 15 minutes, HPLC analysis as described in Example 10, section (a) showed product eluting at Rt=22 minutes. The product was purified by preparative HPLC as described in Example 4, section (c) using a 40 minute gradient of 0→40% MeCN/water (with 0.05% TFA). The HPLC fractions containing product were frozen at −80° C. and lyophilized to dryness to afford a white fluffy powder. Yield=6.3 mg (28%); MALDI-TOF MS 705 observed.

The following reactions describe the synthesis of biotin-Z—NHS, compound 10c.

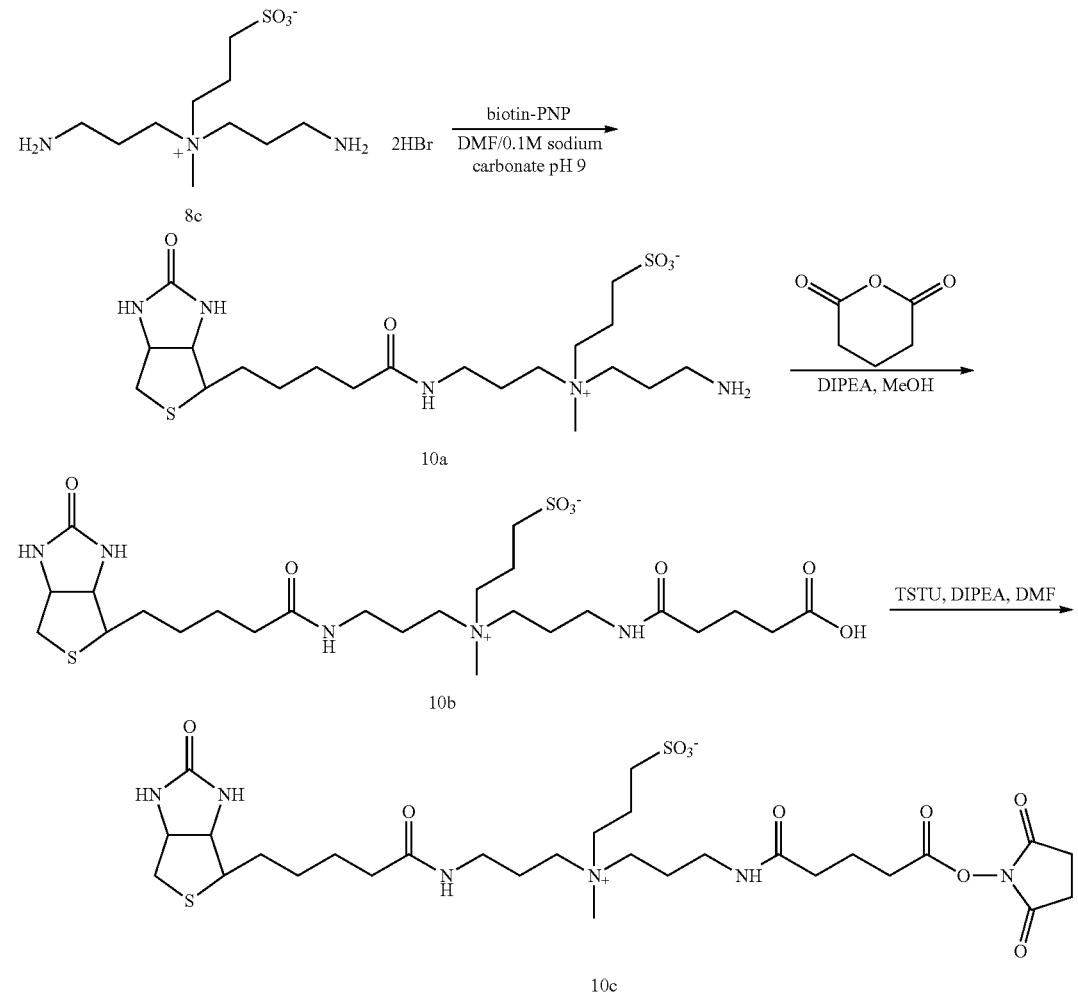

Example 11

Synthesis of Fluorescein-Z—NH2, Compound 11a, Fluorescein-Z—NHS, Compound 11c, Fluorescein-Z-3-CMO-Progesterone, Compound 11d, and Fluorescein-Z-22-CMO-FK506, Compound 11e a) Compound 11a A solution of carboxyfluorescein-NHS ester (5 and 6 isomers, 10 mg, 21.1 μmoles) in DMF (1 mL) was added drop-wise to a stirred solution of compound 8a (28 mg, 62.6 μmoles, HBr salt) dissolved in 1.5 mL of 25% DMF, 75% 0.1 M sodium carbonate pH 9. The reaction was stirred at room temperature. After 30 minutes, HPLC analysis of a small portion of the reaction mixture was performed using a Phenomenex, $C_{18}$ 4.6 mm×25 cm column and a 30 minute gradient of 10→70% B (A=water with 0.05% TFA, B=MeCN with 0.05% TFA) at a flow rate of 1.0 mL/minute and UV detection at 260 nm. Product was observed eluting at Rt=12.5 minutes. The crude reaction mixture was purified by HPLC using an YMC, $C_{18}$, 30×250 mm column and a 30 minute gradient of 10→70% MeCN/water (with 0.05% TFA) above at a flow rate of 20 mL/minute. HPLC fractions containing product were concentrated under reduced pressure. Yield=12.3 mg (93%); MALDI-TOF MS 626.4 observed.

b) Compound 11b

A solution of compound 9a (12.3 mg, 19.6 umoles) in methanol (2 mL) was treated with diisopropylethylamine (17 uL, 5 equivalents) and glutaric anhydride (11 mg, 5 equivalents). The reaction was stirred at room temperature. After 30 minutes, HPLC analysis of a small portion of the reaction mixture was performed using a Phenomenex, $C_{18}$ 4.6 mm×25 cm column and a 30 minute gradient of 10→70% B (A=water with 0.05% TFA, B=MeCN with 0.05% TFA) at a flow rate of 1.0 mL/minute and UV detection at 260 nm. Product was observed eluting at Rt=14.5 minutes along with a byproduct eluting at Rt=17.5 minutes (reaction at the phenol). The reaction mixture was treated with 0.2 mL of 0.5 M aqueous piperidine and stirred for 30 minutes. Subsequent HPLC analysis indicated complete hydrolysis of the phenolic ester and clean formation of product eluting at Rt=14.5 minutes. The crude reaction mixture was purified by HPLC using an YMC, $C_{18}$, 30×250 mm column and a 30 minute gradient of 10→70% MeCN/water (with 0.05% TFA) above at a flow rate of 20 mL/minute. HPLC fractions containing product were concentrated under reduced pressure. Yield=8.1 mg (56%); MALDI-TOF MS 739.8 observed.

c) Compound 11c

A solution of compound 9b (12.3 mg, 16.6 umoles) in anhydrous DMF (2 mL) was treated with N-hydroxysuccinimide (9.6 mg, 5 equivalents) and EDC.HCl (10 mg, 3 equivalents). The reaction was stirred at room temperature and after 30 minutes, HPLC analysis of a small portion of the reaction mixture was performed using a Phenomenex, $C_{18}$ 4.6 mm×25 cm column and a 30 minute gradient of 10→70% B (A=water with 0.05% TFA, B=MeCN with 0.05% TFA) at a flow rate of 1.0 mL/minute and UV detection at 260 nm. Product (~30% conversion) was observed eluting at Rt=16 minutes. Additional EDC.HCl (10 mg, 3 equivalents) was added and the reaction was continued. HPLC analysis after 2 h indicated ~70% conversion. The crude reaction mixture was purified by HPLC using an YMC, $C_{18}$, 30×250 mm column and a 30 minute gradient of 10→70% MeCN/water (with 0.05% TFA) above at a flow rate of 20 mL/minute. HPLC fractions containing product were frozen at −80° C. and lyophilized to dryness. Yield=10 mg (71%); MALDI-TOF MS 836.6 observed.

d) Compound 11d

To an anhydrous DMF (1 mL) solution of progesterone-3-CMO (8.1 mg, 21 moles), compound 11a (13 mg, 21 moles), diisopropylethylamine (7.3 L, 42 moles), and BOP reagent (13.8 mg, 31 moles) were added. The reaction was stirred at room temperature for 24 hours and then analyzed by HPLC using a YMC, $C_{18}$, 50×4.0 mm, 3 micron column and a 10 minute gradient of 10-90% MeCN/water (with 0.05% TFA) at a flow rate of 1.0 mL/minute and UV detection at 260 nm. Product was observed eluting at Rt=7.8 minutes. The product was purified by preparative HPLC using an YMC, $C_{18}$, 30×250 mm column and a 30 minute gradient of 10→90% MeCN/water (with 0.05% TFA) at a flow rate of 20 mL/minute. The product fraction was collected and frozen at −80° C. and lyophilized. A yellow powder was obtained. Yield=14.4 mg (70%); MALDI-TOF MS 995.1 observed.

e) Compound 11e

To anhydrous dimethyl formamide (0.5 mL), FK506-C22-CMO (8.8 mg, 10 moles, WO93/25533), 11a (7.5 mg, 12 moles), diisopropylethylamine (4.4 L, 25 moles) and BOP reagent (8.9 mg, 20 moles) were added. The mixture was stirred at room temperature for 24 hours. The reaction mixture was then analyzed by HPLC using a Phenomenex Luna PFP (2), 150×4.6 mm, 3 micron column using a 20 minutes gradient of 10-90% MeCN/water (with 0.05% TFA) at a flow rate of 1.0 mL/minute and UV detection at 260 nm and 220 nm. The product eluted at 14.8-5.1 minutes and starting material eluted at 17.8 minutes. The reaction mixture was purified using a YMC, $C_{18}$, 30×250 mm column and a 30 minute gradient of 10→90% MeCN/water (with 0.05% TFA) at a flow rate of 20 mL/minute. HPLC fractions containing product were frozen at −80° C. and lyophilized to dryness. A yellow powder (8.2 mg) was obtained as the desired product (MALDI-TOF MS: MH$^+$1484.30, 55% yield).

Figure 2A:
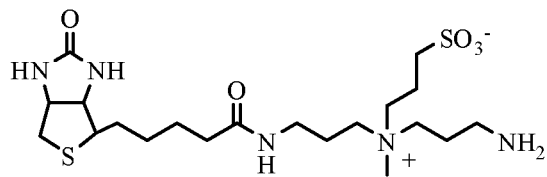
FIG. 2a provides the chemical structures of a plurality of exemplary zwitterion-containing compounds of the present invention for labeling an analyte, analyte analog, or binding partner for an analyte.
Figure 2A:
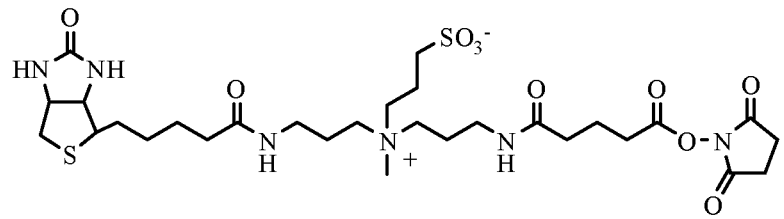
Figure 2A:
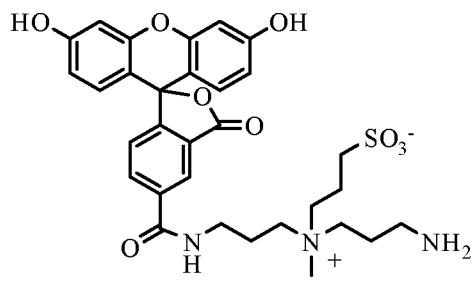
Figure 2A:
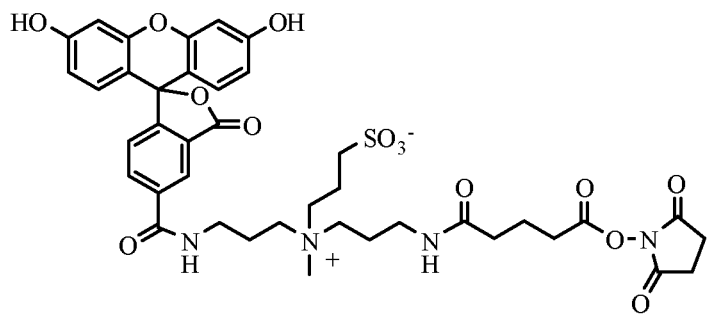
Figure 2B:
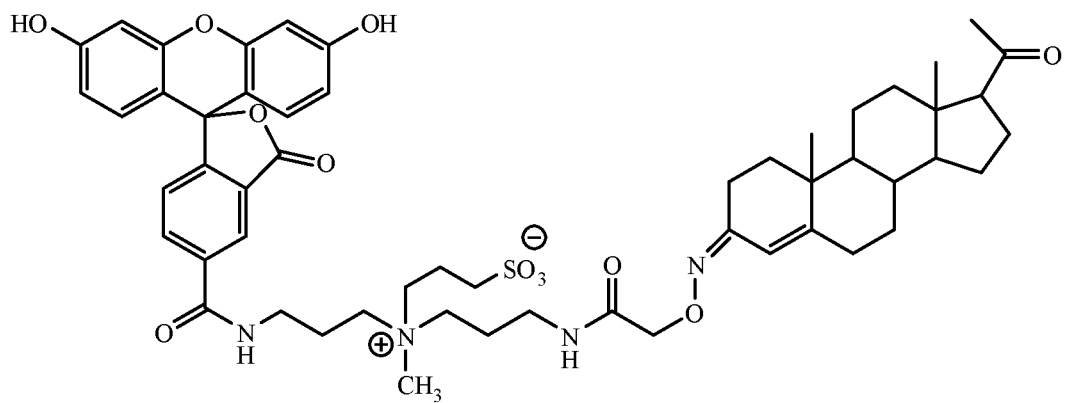
FIG. 2b provides the chemical structures of two exemplary conjugates each having an analyte covalently linked to a zwitterion-containing compound of the present invention.
Figure 2B:
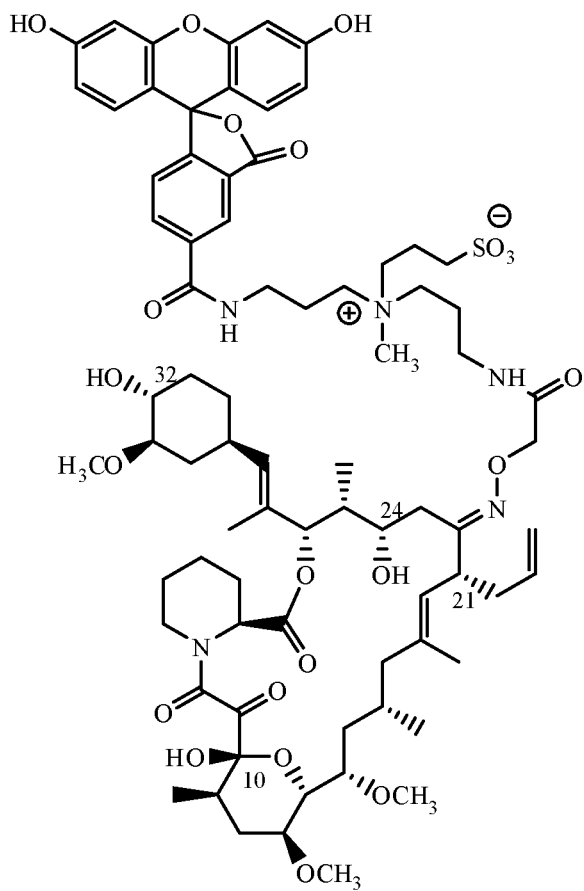

The following reactions describe the synthesis of compounds illustrated in FIGS. 2a and 2b.

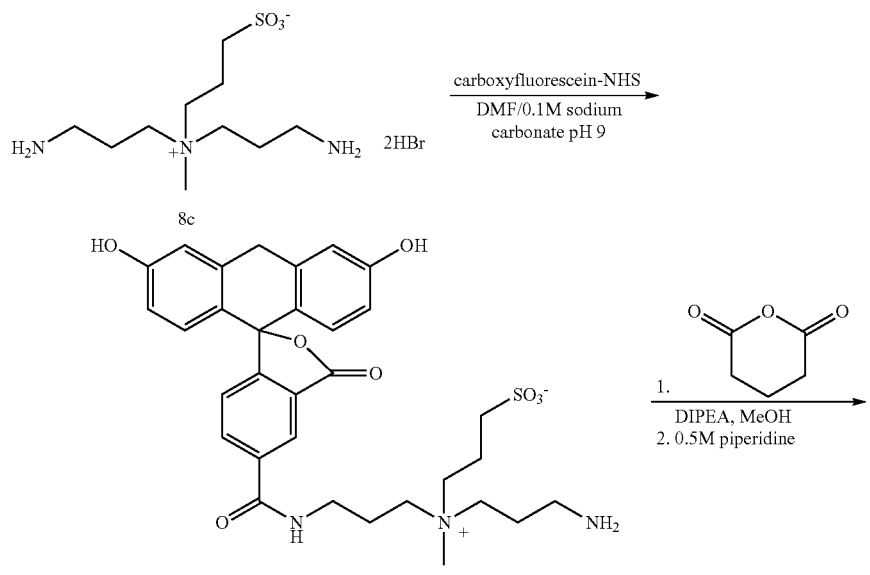

-continued
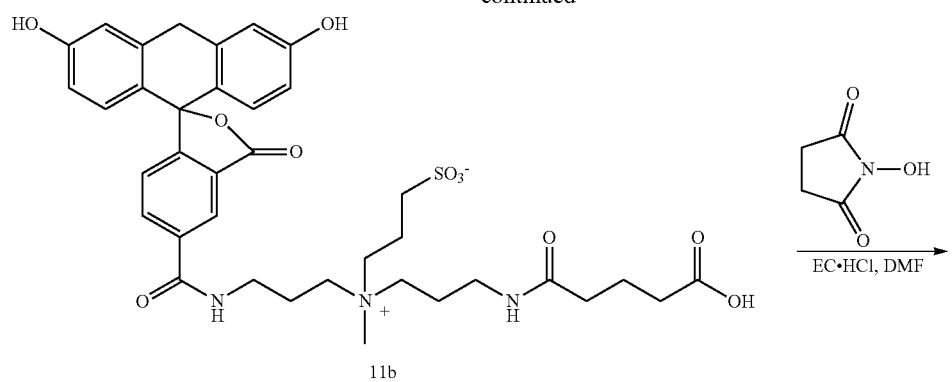
11b
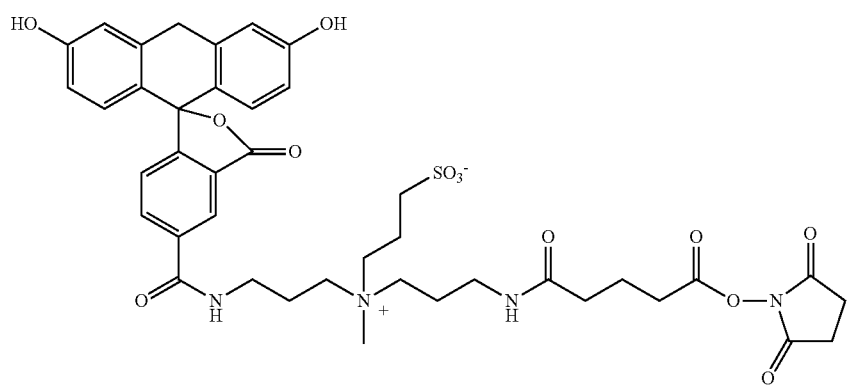
11c
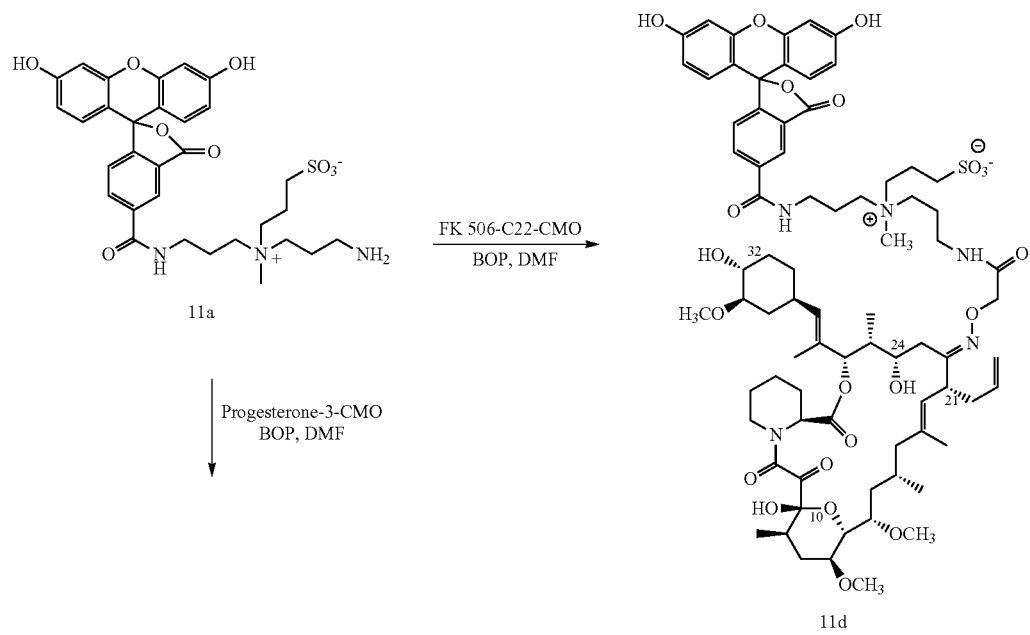

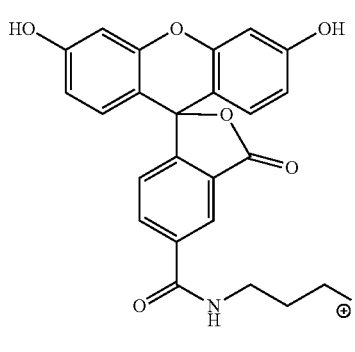
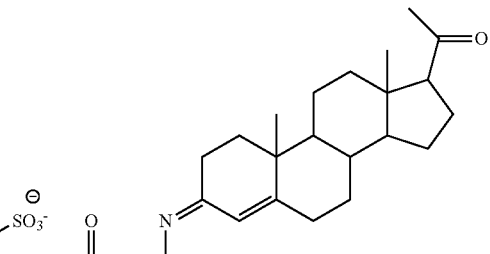

11e

Example 12

Hydrophobic Peptide Labeling with Zwitterion

The following is an illustrative procedure for the labeling of penta(phenylalanine) with Z3-PFP, compound 2c, as shown in FIG. 3b.

A solution of penta(phenylalanine) (2 mg, 2.65 umoles) in dimethyl sulfoxide (0.8 mL) was treated with Z3-PFP, compound 2c, (2 mg, 4.8 umoles) dissolved in 1:1 dimethyl sulfoxide/water (0.1 mL) followed by aqueous sodium carbonate (0.1 mL, 100 mM, pH 9). The reaction was stirred at room temperature for 16 hours. HPLC analysis of a small portion of the reaction mixture was performed using a Phenomenex, $C_{18}$ 4.6 mm×25 cm column and a 30 minute gradient of 10→100% MeCN/water (with 0.05% TFA) at a flow rate of 1.0 mL/minute and UV detection at 220 and 260 nm. The labeled peptide was observed to elute at Rt=18.5 minutes. The crude reaction mixture was purified by HPLC using an YMC, $C_{18}$, 30×250 mm column and a 30 minute gradient of 10→100% MeCN/water (with 0.05% TFA) above at a flow rate of 20 mL/minute. HPLC fractions containing product were frozen at −80° C. and lyophilized to dryness. Yield=2.4 mg (92%); MALDI-TOF MS 988.4 observed.

Example 13

Conjugation of Penta(Phenylalanine) with Phe-Gly-Gly-Phe with Z-Di-NHS, Compound 8d a) Compound 13a A solution of compound 8d, Z-Di-NHS (4.5 mg, 8.3 µmoles) in anhydrous dimethyl sulfoxide (2 mL) was added to penta(phenylalanine) (2 mg, 2.7 µmoles) along with diisopropylethylamine (2 µL, 11.4 umoles). The reaction was stirred at room temperature. After 16 hours, HPLC analysis of the reaction mixture was performed using a Phenomenex, $C_{18}$ 4.6 mm×25 cm column and a 30 minute gradient of 10→100% MeCN/water (with 0.05% TFA) at a flow rate of 1.0 mL/minute and UV detection at 220 nm and 260 nm. Product 13a (~65% conversion) was observed eluting at Rt=17 minutes. The crude reaction mixture was purified by HPLC using an YMC, $C_{18}$, 30×250 mm column and a 30 minute gradient of 10→100% MeCN/water (with 0.05% TFA) above at a flow rate of 20 mL/minute. HPLC fractions containing product were frozen at −80° C. and lyophilized to dryness. Yield=2.0 mg (64%); MALDI-TOF MS 1187.8 observed.

b) Compound 13b

A mixture of compound 13a (2 mg, 1.68 moles), Phe-Gly-Gly-Phe (3.6 mg, 5 equivalents) and diisopropylethylamine (1.5 µL, 5 equivalents) in dimethyl sulfoxide (2.5 mL) was stirred at room temperature. After 1 hour, HPLC analysis was performed as described in Example 13, section (a). Product 13b was observed eluting at Rt=19 minutes. The product was purified as described in section (a). Yield=1.6 mg (63%); MALDI-TOF MS 1500.2 observed.

The following reactions describe the synthesis of a conjugate of penta(phenylalanine) with Phe-Gly-Gly-Phe linked by Z-Di-NHS, compound 13b.

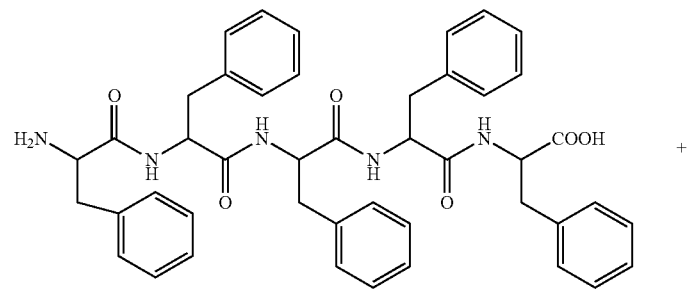

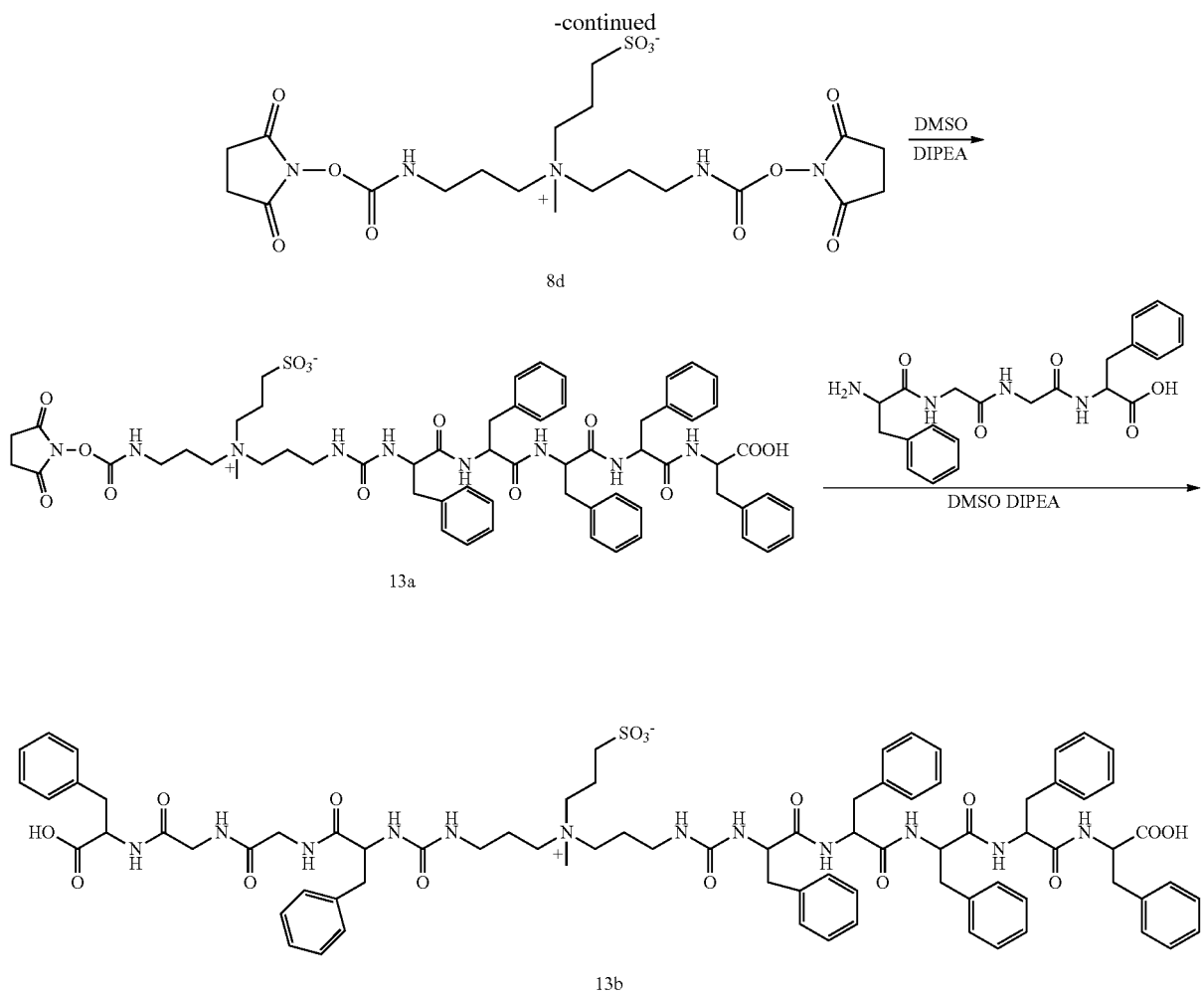

Example 14

Conjugation of Penta(Phenylalanine) with Cys-Gly Using Z-Maleimide-NHS, Compound 9e A solution of penta(phenylalanine) (8 mg, 11.2 μmoles) and compound 9e (4 mg, 5.6 μmoles) in anhydrous DMF (3 mL) was treated with triethylamine (4 μL, 4 equivalents). The reaction was stirred at room temperature for 16 hours and then analyzed by HPLC using a Phenomenex, $C_{18}$ 4.6 mm×25 cm column and a 30 minute gradient of 10→100% MeCN/water (with 0.05% TFA) at a flow rate of 1.0 mL/minute and UV detection at 220 and 260 nm. Product 14a was observed eluting at Rt=18.4 minutes (MALDI-TOF MS 1355.8 observed). Starting material 9e eluting at Rt=10 minutes was completely consumed. To the reaction mixture was added the dipeptide Cys-Gly (2 mg, 11.1 μmoles). The reaction was stirred at room temperature. After 20 minutes, HPLC analysis indicated clean formation of the heptapeptide 14b eluting at Rt=16.5 minutes with no 14a at Rt=18.4 minutes. The heptapeptide was purified by HPLC using an YMC, $C_{18}$, 30×250 mm column and a 30 minute gradient of 10→100% MeCN/water (with 0.05% TFA) above at a flow rate of 20 mL/minute. HPLC fractions containing product were frozen at −80° C. and lyophilized to dryness. Yield=8.8 mg (quantitative) MALDI-TOF MS 1535.3 observed.

The following reactions describe the synthesis of the heptapeptide 14b.

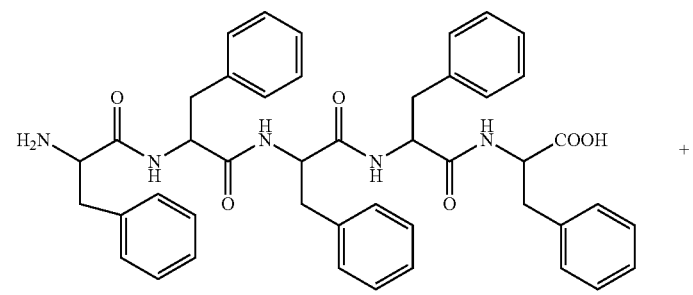

-continued

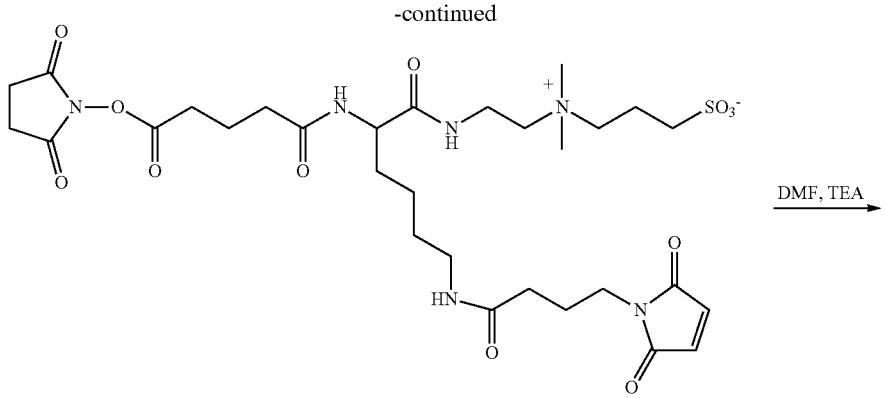

9e

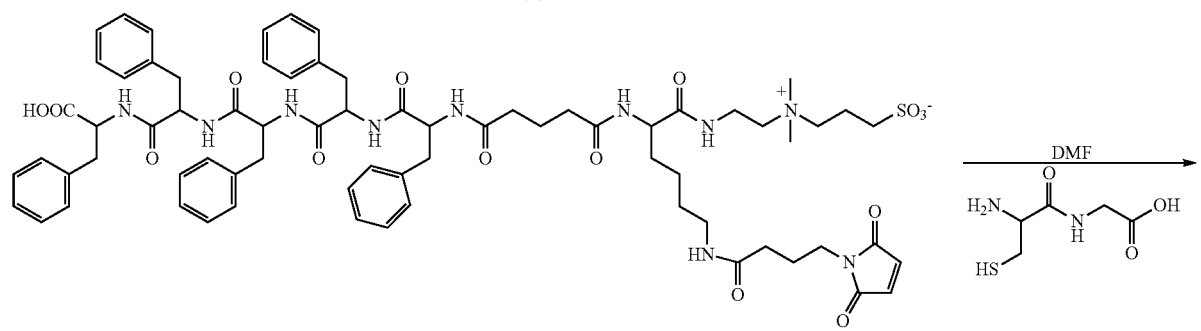

14a

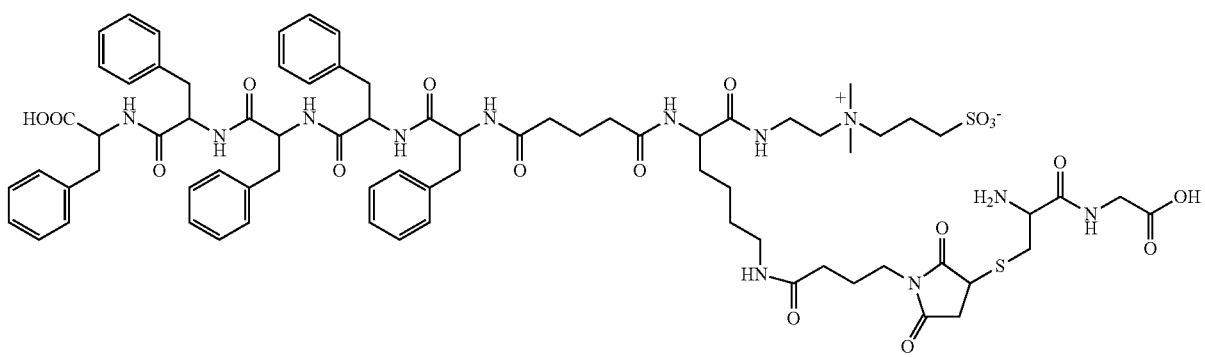

14b

Example 15

General Procedure for the Labeling of BSA with Acidinium Ester and Zwitterion Labels 1d, 2c, 3c and 4c (Table 1)

A solution of BSA (4 mg, 60 nmoles) in 1 mL of 0.1 M sodium bicarbonate was treated with 5 equivalents of 2',6'-Dimethyl-4'-(N-succinimidyloxycarboxnyl)phenyl 10-(3'-Sulfopropyl)-acridinium-9-carboxylate (NSP-DMAE-NHS) added as a solution in DMF (72 µL of a 2 mg/mL solution in DMF). The reaction was stirred at room temperature for 4 hours. The reaction was then transferred to a 4 mL amicon filter (MW 30,000 cutoff) and diluted with 3 mL de-ionized water. The filter was centrifuged at 4000G for 8 minutes to reduce the volume to about 0.25 mL. The final conjugate was diluted to 0.8 mL with de-ionized water to give a 5 mg/mL solution. Acridinium ester label incorporation, measured by MALDI-TOF mass spectroscopy using sinnapinic acid as matrix indicated the incorporation of 1.4 labels.

Further labeling of the acridinium ester-labeled BSA conjugate with the zwitterion labels 1d, 2c, 3c and 4c was carried out as follows. The conjugate (0.5 mg, 7.5 nmoles, 100 µL) was diluted with 100 µL of sodium carbonate, pH 9. To this conjugate, in four separate reactions, was added 10 equivalents of the four zwitterion labels 1d, 2c, 3c and 4c dissolved in DMSO corresponding to 12.8 µL of a 2.5 mg/mL solution of 1d; 16.5 µL of a 2 mg/mL solution of 2c; 16.5 µL of a 2 mg/mL solution of 3c and 14 µL of a 2.5 mg/mL solution of 4c. The reactions were stirred at room temperature for 4 hours and were then processed as described above. Zwitterion label incorporation was measured by MALDI-TOF mass spectroscopy and the results are listed in Table 1.

Example 16

General Procedure for the Labeling of Proteins with Acridinium Ester and Zwitterion Label Z3-PFP. Compound 2c (Table 2)

A solution of 2 mg/mL of egg white avidin (AVD), bovine gamma globulin (BGG) and bovine fibrinogen (FBN) was prepared in 1 mL of 0.1 M sodium carbonate, pH 9. The protein solutions were then treated with 10 equivalents of NSP-DMAE-NHS described by Natrajan et al. in U.S. Pat. No. 5,656,246, which was added in the form a solution in DMSO. Specifically, a 2 mg/mL solution of the acridinium ester in DMSO was prepared and 89 µL, 40 µL and 18 µL of this solution was added to AVD, BGG and FBN respectively. The reactions were stirred at 4° C. for 3 hours. A portion (0.5 mL) of each reaction was further treated with a 25 equivalents of Z3-PFP, compound 2c, which was added in the form a solution in DMSO. Specifically, a 5 mg/mL solution of Z3-PFP in DMSO was prepared and 32 µL, 14 µL and 6 µL of this solution was added to acridinium ester-labeled AVD, BGG and FBN, respectively. The reactions were stirred at 4° C. for 16 hours. All six conjugates were then diluted with 0.5 mL each of 0.1 M phosphate, pH 7.4 and transferred to 4 mL centricon filters. The conjugates were further diluted with 3 mL buffer and centrifuged at 4000G for 7 minutes to reduce the volume to about 0.2 mL. This process was repeated two more times. The final conjugates were diluted to a total volume of 0.5 to 1.0 mL in phosphate buffer and stored at 4° C.

Example 17

Measurement of Non-Specific Binding

The fractional nonspecific bindings (fNSBs) of three proteins avidin, bovine gamma-globulin, and fibrinogen, each labeled with NSP-DMAE and the zwitterion label Z3-PFP, were measured and compared to the non-specific bindings of the three same proteins, labeled only with NSP-DMAE. The conjugates were diluted to equivalent concentrations of 10 nanomolar in a solution consisting of 0.1 molar sodium N-(2-hydroxyethyl) piperazine-N'-2-ethanesulfonate (HEPES), 0.15 molar sodium chloride, 7.7 millimolar sodium azide, 1.0 millimolar tetrasodium ethylenediaminetetraacetate (EDTA), 12 millimolar t-octylphenoxypolyethoxyethanol (Triton X-100), 76 micromolar bovine serum albumin, 7 micromolar mouse immunoglobin, pH 7.7. 100 microliters of these 10 nanomolar protein-acridinium ester solutions were each mixed with 200 microliters of horse serum and 200 microliters of either of three solid phases. The first solid phase was 0.35 grams per liter of Siemens Healthcare Diagnostics paramagnetic microparticles (PMP) covalently covered with sheep antibody. The second solid phase was 0.35 grams per liter of polystyrene tosylactivated beads (Invitrogen Corporation M-280 magnetic latex microparticle (MLP) Dynalbeads) covalently covered with streptavidin. The third solid phase was 0.35 grams per liter of glycidyl ether (epoxy) carboxylic acid beads (Invitrogen Corporation M-270 magnetic latex microparticle (MLP) Dynalbeads) covalently covered with streptavidin. The specific beads used for the second and third solid phases having the following specifications:

| M-280 Magnetic Latex Particle | M-270 Magnetic Latex Particle |
|---|---|
| Based on polystyrene tosylactivated beads | Based on glycidyl ether (epoxy) carboxylic acid beads |
| Diameter: 2.8 µm | Diameter: 2.8 µm |
| Size distribution: CV <3% | Size distribution: CV <3% |
| BSA as blocking protein | No blocking proteins used |
| Isoelectric point: pH 5.0 | Isoelectric point: pH 4.5 |
| Low charge (−10 mV (at pH 7) | Highly charged (−50 mV (at pH 7) |
| Iron content (Ferrites): 12% (17%) | Iron content (Ferrites): 14% (20%) |
| | Low aggregation of beads in high salt solutions |

The solid phases were magnetically collected and washed twice with water after an incubation of 10 minutes to allow interaction between the acridinium ester covalently attached proteins and the solid phases. The chemiluminescence of both the input acridinium ester chemiluminescence and the chemiluminescence of the acridinium ester associated with the particles was measured for 5 seconds under standard conditions on a Berthold Technologies' Autolumat LB953 luminometer with sequential addition of 250 microliters each of Siemens Healthcare Diagnostics Flash Reagent 1 (0.1 M nitric acid and 0.5% hydrogen peroxide) and Siemens Healthcare Diagnostics Flash Reagent 2 (0.25 M sodium hydroxide and 0.05% cetyltrimethylammonium chloride). Fractional nonspecific binding is calculated as the ratio of particle-bound chemiluminescence from acridinium ester bound to the solid phases divided by the total chemiluminescence of acridinium ester input.

What is claimed is:

1. A zwitterion-containing compound for labeling an analyte, analyte analog, or binding partner for an analyte having the structure of formula (II):

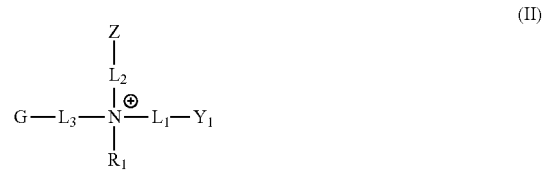

(II)

wherein, $L_1$ and $L_3$, are independently selected at each occurrence from divalent $C_{1-20}$ alkyl, alkenyl, alkynyl, aryl, or aralkyl groups, each optionally substituted with up to 20 heteroatoms;

$L_2$ is a bond or a divalent $C_{1-4}$ alkyl, alkenyl, or alkynyl group, optionally substituted with up to 10 heteroatoms;

Z is an anion-containing group selected from the group consisting of carboxylate (—COO⁻), sulfonate (SO₃⁻), sulfate (—OSO₃⁻), phosphate (—OP(O)(OR)(O⁻), and oxide (—O⁻¹), where R is a $C_{1-12}$ alkyl, alkenyl, alkynyl, aryl, or aralkyl, optionally substituted with up to 20 heteroatoms;

$Y_1$ is a reactive functional group for forming covalent linkages with an analyte, analyte analog, or binding partner for an analyte, said functional group comprising a electrophilic group, nucleophilic group, or a photo-reactive group;

G is a fluorescent label or biotin; and $R_1$ is a $C_{1-20}$ alkyl, alkenyl, alkynyl, aryl, or aralkyl, optionally substituted with up to 20 heteroatoms.

2. The zwitterion-containing compound according to claim 1, wherein $Y_1$ is an amine-reactive group, a thiol-reactive group, a carboxy-reactive group, a maleimidyl-reactive group, a carbohydrate-reactive group, or a photo-reactive-group.

3. The zwitterion-containing compound according to claim 2, wherein $Y_1$ is selected from the group consisting of:

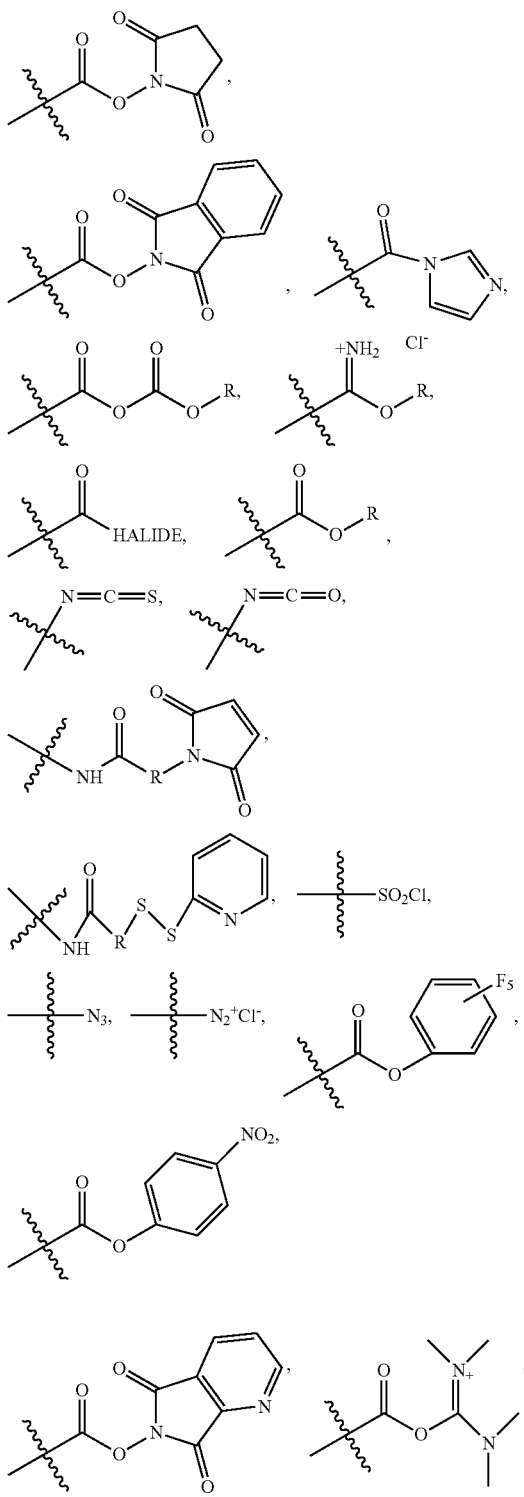

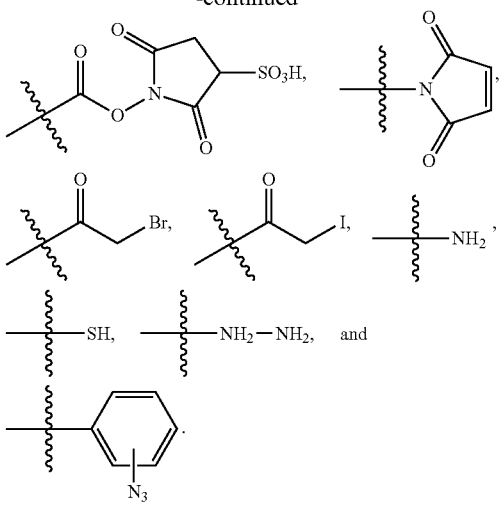

4. The zwitterion-containing compound according to claim 3, wherein $Y_1$ is a pentafluorophenyl (PFP) ester, maleimide, amine, or N-succinimidyloxycarbonyl.

5. The zwitterion-containing compound according to claim 1, wherein, $L_3$ is a group $—X^G—R^G—$, where $X^G$ is attached to G, and $X^G$ is selected from a bond, oxygen, sulfur, amine, amide (—C(O)NR$^N$— or —NR$^N$—C(O)—), ester (—C(O)—O— or —O—C(O)—), carbamate (—NR$^N$—C(O)—O— or —O—C(O)—NR$^N$—) or urea (—NR$^N$—C(O)—NR$^N$—), and R$^N$ is hydrogen or a $C_{1-20}$ alkyl, alkenyl, alkynyl, aryl, or aralkyl, optionally substituted with up to 20 heteroatoms; and $R^G$ is a divalent $C_{1-20}$ alkyl, alkenyl, alkynyl, aryl, or aralkyl group, optionally substituted with up to 20 heteroatoms.

6. The zwitterion-containing compound according to claim 5, wherein, $L_1$ is selected from divalent $C_{1-10}$ alkyl groups, optionally substituted with up to 20 heteroatoms, and $R^G$ is a divalent $C_{1-10}$ alkyl, optionally substituted with up to 20 heteroatoms.

7. The zwitterion-containing compound according to claim 6, wherein $L_1$ is a divalent radical of the form —(CH$_2$)$_n$— where n=1 to 6.

8. The zwitterion-containing compound according to claim 6, wherein $R^G$ is a divalent radical of the form —(CH$_2$)$_g$— where g=1 to 6.

9. The zwitterion-containing compound according to claim 6, wherein $L_2$ is a divalent $C_{1-4}$ alkyl, optionally substituted with up to 10 heteroatoms.

10. The zwitterion-containing compound according to claim 9, wherein $L_2$ is a divalent radical of the form —(CH$_2$)$_m$— where m=1 to 4.

11. The zwitterion-containing compound according to claim 1, wherein Z is sulfonate (—SO$_3^-$).

12. The zwitterion-containing compound according to claim 1, wherein Z is phosphate (—OP(O)(OR)(O$^-$)).

13. The zwitterion-containing compound according to claim 1, wherein Z is carboxylate (—COO$^-$).

14. The zwitterion-containing compound according to claim 11, having the structure:

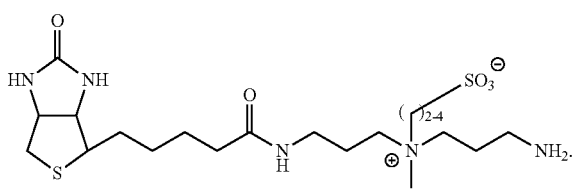

15. The zwitterion-containing compound according to claim 11, having the structure:

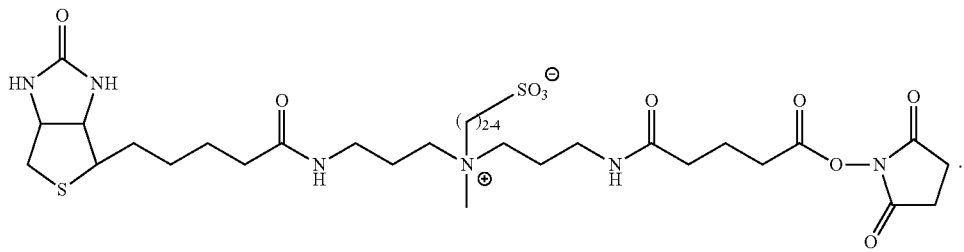

16. The zwitterion-containing compound according to claim 11, having the structure:

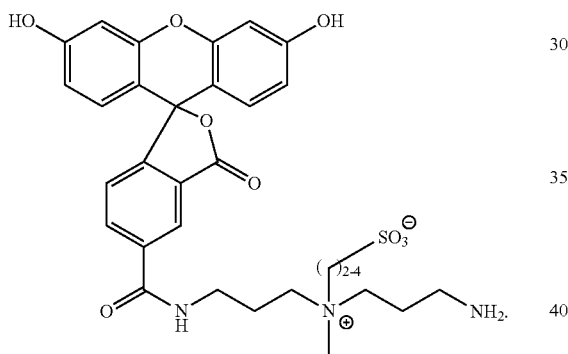

17. The zwitterion-containing compound according to claim 11, having the structure:

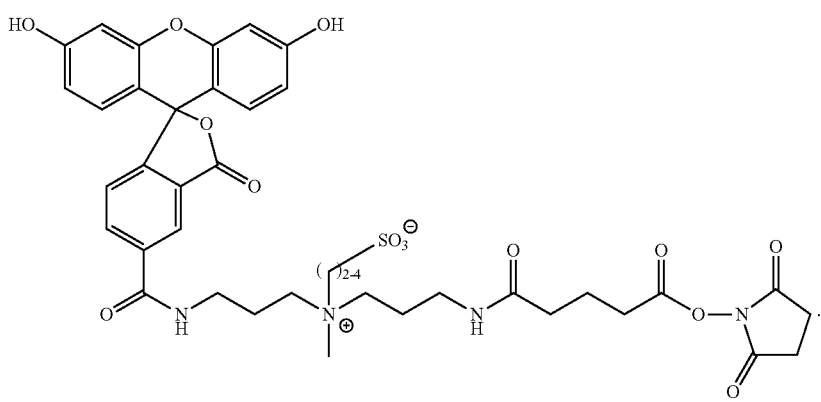

18. A zwitterion-containing compound for cross-linking peptides, proteins, and/or macromolecules having the structure of formula (III):

$$Y_1\text{-}\Omega\text{-}Y_2 \qquad (III)$$

wherein,

Ω is a zwitterion-containing group of the form

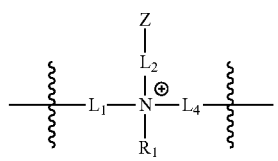

$L_1$ and $L_4$ are independently selected at each occurrence from divalent $C_{1-20}$ alkyl, alkenyl, alkynyl, aryl, or aralkyl groups, each optionally substituted with up to 20 heteroatoms;

$L_2$ is a bond or a divalent $C_{1-4}$ alkyl, alkenyl, alkynyl, aryl, or aralkyl group, optionally substituted with up to 10 heteroatoms;

Z is an anion-containing group selected from the group consisting of carboxylate (—COO⁻), sulfonate (—SO₃⁻), sulfate (—OSO₃⁻), phosphate (—OP(O)(OR)(O⁻), and oxide (—O⁻);

$Y_1$ and $Y_2$ are independently selected from the group consisting of

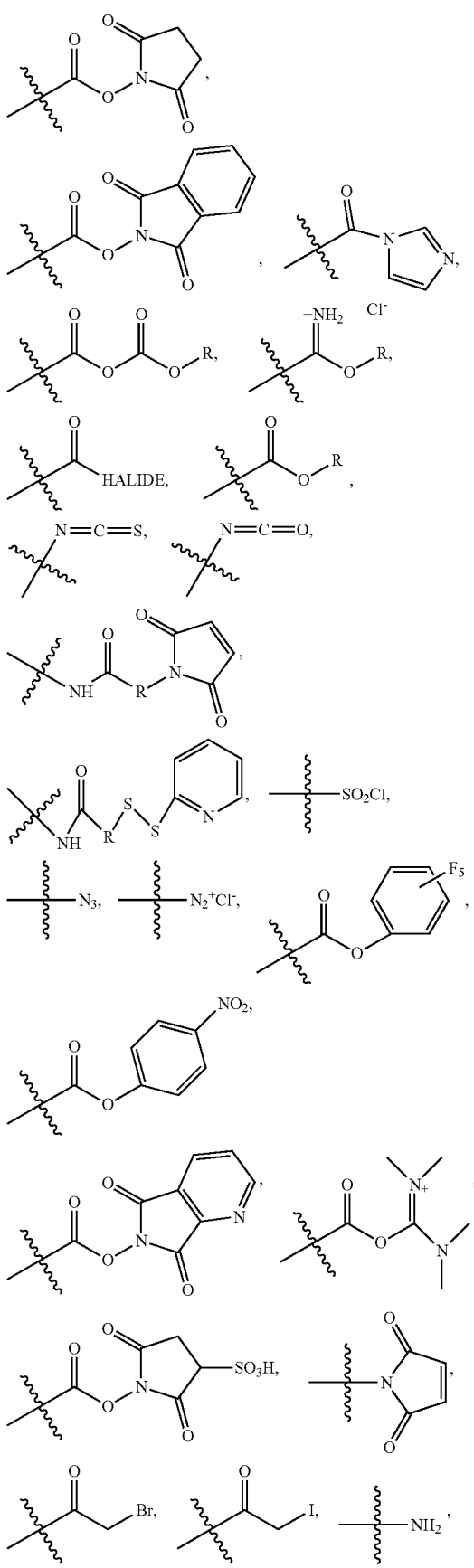

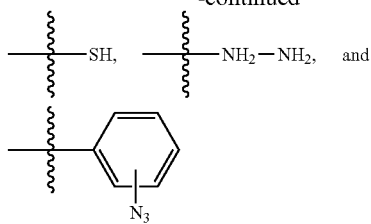

with the proviso that $Y_1$ and $Y_2$ are not each $NH_2$;
$R_1$ is $C_{1-20}$ alkyl, alkenyl, alkynyl, aryl, or aralkyl, each optionally substituted with up to 20 heteroatoms; and
R is independently at each occurrence a $C_{1-12}$ alkyl, alkenyl, alkynyl, aryl, or aralkyl, optionally substituted with up to 20 heteroatoms.

19. The zwitterion-containing compound according to claim 18, wherein $Y_1$ or $Y_2$ is, at one occurrence, a pentafluorophenyl (PFP) ester, maleimide, amine, or N-succinimidyloxycarbonyl.

20. The zwitterion-containing compound according to claim 18, wherein $L_2$ is a divalent $C_{1-4}$ alkyl, optionally substituted with up to 10 heteroatoms.

21. The zwitterion-containing compound according to claim 20, wherein $L_2$ is a divalent radical of the form $-(CH_2)_m-$ where m=1 to 4.

22. The zwitterion-containing compound according to claim 18, wherein $L_2$ is a divalent radical of the form $-(CH_2)_m-$ where m=1 to 4.

23. The zwitterion-containing compound according to claim 18, wherein $L_1$ is a divalent radical of the form $-(CH_2)_n-$ where n=1 to 6.

24. The zwitterion-containing compound according to claim 18, wherein $L_4$ is a divalent radical of the form $-(CH_2)_p-$ where p=1 to 6.

25. The zwitterion-containing compound according to claim 18, wherein Z is sulfonate ($-SO_3^-$).

26. The zwitterion-containing compound according to claim 25, having the structure:

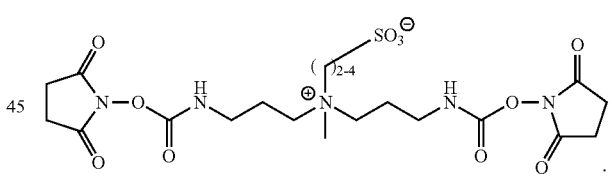

27. A zwitterion-containing compound for cross-linking peptides, proteins, and/or macromolecules having the structure of formula (III):

$$Y_1\text{-}\Omega\text{-}Y_2 \qquad (III)$$

$\Omega$ is a zwitterion-containing group of the form

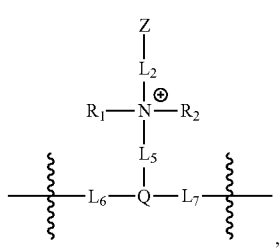

, and

L$_2$ is a bond or a divalent C$_{1-4}$ alkyl, alkenyl, alkynyl, aryl, or aralkyl group, optionally substituted with up to 10 heteroatoms;

L$_5$, L$_6$, and L$_7$ are independently selected at each occurrence from a bond or divalent C$_{1-20}$ alkyl, alkenyl, alkynyl, aryl, or aralkyl groups, each optionally substituted with up to 20 heteroatoms;

Q is selected from CH or a nitrogen atom, and with the proviso that when Q is nitrogen, L$_5$, L$_6$, and L$_7$ are each not a bond;

Z is an anion-containing group selected from the group consisting of carboxylate (—COO$^-$), sulfonate (—SO$_3^-$), sulfate (—OSO$_3^-$), phosphate (—OP(O)(OR)(O$^-$)), and oxide (—O$^-$), where R is a C$_{1-12}$ alkyl, alkenyl, alkynyl, aryl, or aralkyl, optionally substituted with up to 20 heteroatoms;

Y$_1$ and Y$_2$ are independently selected at each occurrence from a reactive functional group for forming covalent linkages with a peptide, a protein, or a macromolecule comprising a electrophilic group, a nucleophilic group, or a photoreactive group; and R$_1$ and R$_2$ are independently selected at each occurrence from C$_{1-20}$ alkyl, alkenyl, alkynyl, aryl, or aralkyl, each optionally substituted with up to 20 heteroatoms.

28. The zwitterion-containing compound according to claim 27, wherein L$_2$ is a divalent radical of the form —(CH$_2$)$_m$— where m=1 to 4.

29. The zwitterion-containing compound according to claim 27, wherein L$_5$, L$_6$ and L$_7$ are each a group —X$^a$—R$^a$—, where X$^a$ is attached to Q and is independently selected at each occurrence from a bond, oxygen, sulfur, amine, amide (—C(O)NR$^N$— or —NR$^N$—C(O)—), ester (—C(O)—O— or —O—C(O)—), carbamate (—NR$^N$—C(O)—O— or —O—C(O)—NR$^N$—) or urea (—NR$^N$—C(O)—NR$^N$—), and R$^N$ is independently selected at each occurrence from hydrogen or C$_{1-20}$ alkyl, alkenyl, alkynyl, aryl, or aralkyl groups, optionally substituted with up to 20 heteroatoms; and R$^a$ is independently selected at each occurrence from a divalent radical of the form —(CH$_2$)$_q$— where q=1 to 6.

30. The zwitterion-containing compound according to claim 29, wherein X$^a$ is, at one occurrence, an amine or amide (—C(O)NR$^N$— or —NR$^N$—C(O)—) and Q is carbon.

31. The zwitterion-containing compound according to claim 27, wherein Z is sulfonate (—SO$_3^-$).

32. The zwitterion-containing compound according to claim 31, having the structure:

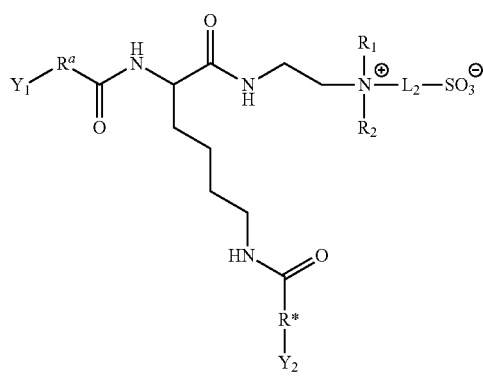

wherein

L$_2$ is a divalent radical of the form —(CH$_2$)$_m$— where m=1 to 4; and

R$^a$ and R* are independently selected at each occurrence from a bond or divalent C$_{1-20}$ alkyl, alkenyl, alkynyl, aryl, or aralkyl groups, each optionally substituted with up to 20 heteroatoms.

33. The zwitterion-containing compound according to claim 32, having the structure:

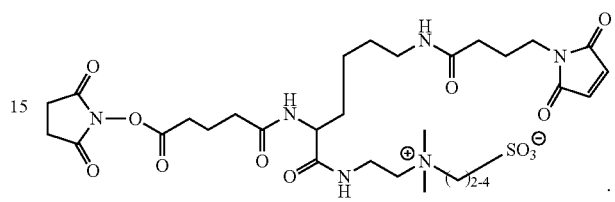

34. A method of labeling an analyte, analyte analog, or binding partner for an analyte in a biologic binding assay comprising covalently attaching the zwitterion-containing compound according to claim 1 to said analyte, analyte analog, or binding partner for an analyte.

35. A method for preparing a conjugate of two molecules and/or macromolecules comprising covalently attaching the zwitterion-containing compound according to claim 18 to a first molecule or macromolecule and a second molecule or macromolecule.

36. A zwitterion-containing compound for cross-linking peptides, proteins, and/or macromolecules having the structure of formula (III):

$$Y_1\text{-}\Omega\text{-}Y_2 \qquad (III)$$

wherein,

Ω is a zwitterion-containing group of the form

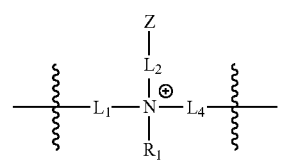

L$_1$ and L$_4$ are independently selected at each occurrence from divalent C$_{1-20}$ alkyl, alkenyl, alkynyl, aryl, or aralkyl groups, each optionally substituted with up to 20 heteroatoms;

L$_2$ is a bond or a divalent C$_{1-4}$ alkyl, alkenyl, alkynyl, aryl, or aralkyl group, optionally substituted with up to 10 heteroatoms;

Z is an anion-containing group selected from the group consisting of carboxylate (—COO$^-$), sulfonate (—SO$_3^-$), sulfate (—OSO$_3^-$), phosphate (—OP(O)(OR)(O$^-$)), and oxide (—O$^-$);

Y$_1$ and Y$_2$ are independently selected from the group consisting of

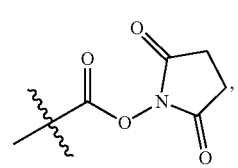

-continued
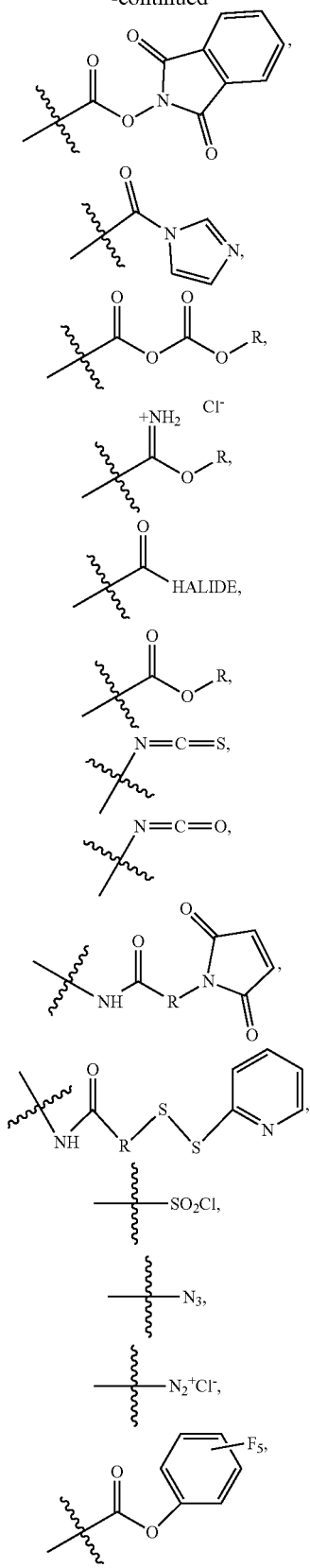
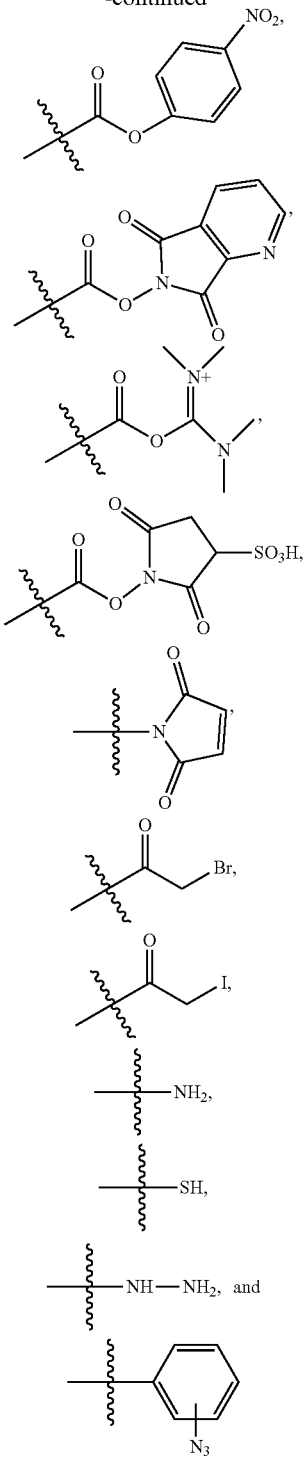
with the proviso that $Y_1$ and $Y_2$ are not each $NH_2$;
$R_1$ is $C_{1-20}$ alkyl, alkenyl, alkynyl, aryl, or aralkyl, each optionally substituted with up to 20 heteroatoms; and
R is independently at each occurrence a $C_{1-5}$ alkyl, $C_{1-5}$ alkenyl, $C_{1-12}$ alkynyl, $C_{1-12}$ aryl, or $C_{1-12}$ aralkyl, optionally substituted with up to 20 heteroatoms.
* * * * *